(12) United States Patent
Fillatti et al.

(10) Patent No.: US 7,601,888 B2
(45) Date of Patent: *Oct. 13, 2009

(54) NUCLEIC ACID CONSTRUCTS AND METHODS FOR PRODUCING ALTERED SEED OIL COMPOSITIONS

(75) Inventors: Joanne J. Fillatti, Davis, CA (US); Neal A. Bringe, St. Charles, MO (US); Katayoon Dehesh, Vacaville, CA (US)

(73) Assignee: Monsanto Technology L.L.C., St. Louis, MO (US)

( * ) Notice: Subject to any disclaimer, the term of this patent is extended or adjusted under 35 U.S.C. 154(b) by 357 days.

This patent is subject to a terminal disclaimer.

(21) Appl. No.: 10/393,347

(22) Filed: Mar. 21, 2003

(65) Prior Publication Data

US 2004/0006792 A1   Jan. 8, 2004
US 2005/0034190 A9   Feb. 10, 2005

Related U.S. Application Data

(60) Provisional application No. 60/365,794, filed on Mar. 21, 2002, provisional application No. 60/390,185, filed on Jun. 21, 2002.

(51) Int. Cl.
*A01H 1/00* (2006.01)
*A01H 5/00* (2006.01)
*C12N 15/82* (2006.01)

(52) U.S. Cl. .................. 800/281; 800/285; 800/278

(58) Field of Classification Search .................. None
See application file for complete search history.

(56) References Cited

U.S. PATENT DOCUMENTS

| | | | |
|---|---|---|---|
| 4,557,734 A | 12/1985 | Schwab et al. | |
| 5,454,842 A | 10/1995 | Poirier et al. | |
| 5,475,099 A | 12/1995 | Knauf et al. | |
| 5,500,361 A | 3/1996 | Kinney | |
| 5,627,061 A | 5/1997 | Barry et al. | |
| 5,633,435 A | 5/1997 | Barry et al. | |
| 5,714,670 A | 2/1998 | Fehr et al. | 800/200 |
| 5,723,595 A | 3/1998 | Thompson et al. | |
| 5,723,761 A | 3/1998 | Voelker et al. | |
| 5,850,026 A | 12/1998 | Debonte et al. | |
| 5,888,947 A | 3/1999 | Lambert et al. | |
| 5,891,203 A | 4/1999 | Ball et al. | |
| 5,955,329 A | 9/1999 | Yuan et al. | |
| 5,955,650 A | 9/1999 | Hitz | |
| 6,013,114 A | 1/2000 | Hille et al. | |
| 6,150,512 A | 11/2000 | Yuan | |
| 6,331,664 B1 | 12/2001 | Rubin-Wilson et al. | |
| 6,369,296 B1 | 4/2002 | Ratcliff et al. | |
| 6,372,965 B1* | 4/2002 | Lightner et al. | 800/298 |
| 6,380,462 B1 | 4/2002 | Kridl | |
| 6,506,559 B1 | 1/2003 | Fire et al. | |
| 6,573,099 B2 | 6/2003 | Graham | |
| 2002/0034814 A1 | 3/2002 | Atabekov et al. | |
| 2003/0049835 A1 | 3/2003 | Helliwell et al. | |
| 2003/0135882 A1 | 7/2003 | Metzlaff et al. | |
| 2003/0172399 A1 | 9/2003 | Fillatti | |
| 2004/0107460 A1 | 6/2004 | Fillatti et al. | |
| 2004/0126845 A1 | 7/2004 | Eenannaam et al. | |
| 2005/0034190 A9 | 2/2005 | Fillatti et al. | |

FOREIGN PATENT DOCUMENTS

| | | |
|---|---|---|
| EP | 0 959 133 A1 | 11/1999 |
| WO | 94/10189 | 5/1994 |
| WO | WO 94/10189 A1 | 5/1994 |
| WO | WO 94/11516 A1 | 5/1994 |
| WO | WO 96/06936 * | 3/1996 |
| WO | WO 93/11245 A1 | 6/1996 |
| WO | WO 98/05770 A2 | 2/1998 |
| WO | WO 98/30083 A1 | 7/1998 |
| WO | 98/46776 | 10/1998 |
| WO | 98/53083 | 11/1998 |
| WO | WO 99/15682 A2 | 4/1999 |
| WO | WO 99/32619 A1 | 7/1999 |
| WO | WO 99/49029 A1 | 9/1999 |
| WO | 99/53050 A1 | 10/1999 |
| WO | WO 99/61631 A1 | 12/1999 |
| WO | WO 99/64579 A2 | 12/1999 |
| WO | WO 00/07432 A1 | 2/2000 |
| WO | WO 00/18880 | 4/2000 |

(Continued)

OTHER PUBLICATIONS

Buhr et al. 2002, The Plant Journal 30:155-163.*

(Continued)

*Primary Examiner*—Elizabeth F McElwain
*Assistant Examiner*—Li Zheng
(74) *Attorney, Agent, or Firm*—Chunping Li; Arnold & Porter LLP

(57) ABSTRACT

The present invention is in the field of plant genetics and provides recombinant nucleic acid molecules, constructs, and other agents associated with the coordinate manipulation of multiple genes in the fatty acid synthesis pathway. In particular, the agents of the present invention are associated with the simultaneous enhanced expression of certain genes in the fatty acid synthesis pathway and suppressed expression of certain other genes in the same pathway. Also provided are plants incorporating such agents, and in particular plants incorporating such constructs where the plants exhibit altered seed oil compositions.

12 Claims, 17 Drawing Sheets

FOREIGN PATENT DOCUMENTS

| | | |
|---|---|---|
| WO | WO 00/44895 A1 | 8/2000 |
| WO | WO 00/44914 A1 | 8/2000 |
| WO | WO 00/68374 A1 | 11/2000 |
| WO | WO 01/11061 | 2/2001 |
| WO | 01/14538 A3 | 3/2001 |
| WO | WO 01/34822 A2 | 5/2001 |
| WO | WO 01/35726 A1 | 5/2001 |
| WO | WO 01/36598 A1 | 5/2001 |
| WO | 02/04581 | 6/2001 |
| WO | WO 01/70949 A1 | 9/2001 |
| WO | WO 01/79499 A1 | 10/2001 |
| WO | WO 02/15675 A1 | 2/2002 |
| WO | WO 02/059336 A2 | 8/2002 |
| WO | WO 02/081711 A1 | 10/2002 |
| WO | WO 02/088301 A2 | 11/2002 |
| WO | 2003/080802 A3 | 10/2003 |

OTHER PUBLICATIONS

Bosher et al. 1999 Genetics 153:1245-1256.*
Padgette et al. 1995, Crop Sci. 35:1451-1461.*
Sweetlove et al. 1996, Biochem. J. 320:493-498.*
Singh et al. 2005, Current Opinion in Plant Biology 8:197-203.*
Colliver et al 1997, Plant Mol. Biol. 35:509-522.*
Stam et al. 1997, Annals of Botany 79:3-12.*
Thomas et al. 2001, The Plant Journal 25(4):417-425.*
Bouchon et al, "Oil Distribution in Fried Potatoes Monitored by Infrared Microspectroscopy", *Journal of Food Science*, 66(7):918-923 (2001).
Duffield et al., "U.S. Biodiesel Development: New Markets for Conventional and Genetically Modified Agricultural Products", *Economic Research Service USDA*, pp. 1-31 (1998).
Dunn etal., "Recent Advances in the Development of Alternative Diesel Fuel from Vegetable Oils and Animals Fats", *Recent Research, Development in Oil Chemical.*, 1:31-56 (1997).
Erhan et al.,"Lubricant Basestocks from Vegetable Oils", *Industrial Crops and Products*, 11:277-282 (2000).
Halpin et al., "Enabling Technologies for Manipulating Multiple Genes on Complex Pathways", *Plant Molecular Biology*, 47:295-310(2001).
Mensink et al.,"Effect of Dietary Fatty Acids on Serum Lipids and Lipoproteins: A Meta-Analysis of 27 Trials", *Arteriosclerosis and Thrombosis*, 12(8):911-919 (1992).
Napoli et al., "Introduction of a *Chimeric* Chalcone Synthase Gene into Petunia Results in Reversible Co- Suppression of Homologous Genes in trans", *The Plant Cell*, 2:279:289 (1990).
Neff et al., "Odor Significance of Undersirable Degradation Compounds in Heated Triolein and Trilinolein", *JAOCS*, 77(12):1303-1313 (2000).
Timmons et at, "Relationships Among Dietary Roasted Soybeans, Milk Components, and Spontaneous Oxidized Flavor of Milk[1]", *Journal of Diary Science*, 84(11);2440-2449 (2001).
Toborek etal., "Unsaturated Fatty Acids Selectively Induce an Inflammatory Environment in Human Endothelial Cells[1-3]", *American Journal of Clinical Nutrition*, 75:119-125 (2002).
van der Krol etal., "Flavonoid Genes in Petunia: Addition of a Limited Number of Gene Copies May Lead to a Suppression of Gene Expression", *The Plant Cell*, 2:291-299 (1990).
Warner et al., "Effect of Oleic and Linoleic Acids on the Production of Deep-Fried Odor in Heated Triolein and Trilinolein", *Journal of Agricultural Food Chemical*, 49:899-905 (2001).
International Search Report, PCT/US03/08610, Nov. 13, 2003.
International Search Report dated Jul. 12, 2005, issued in PCT/USO4/31605.
Buhr, T. et al., "Ribozyme Termination of RNA Transcripts Down-Regulate Seed Fatty Acid Genes in Transgenic Soybean", *The Plant Journal*, 30(2):155-163 (2002).
Cartea, M.E. et al., "Comparison of Sense and Antisense Methodologies for Modifying the Fatty Acid Composition of *Arabidopsis Thaliana* Oilseed", *Plant Science*, 136:181-194 (1998).
Cogoni, C. et al., "Post-Transcriptional Gene Silencing Across Kingdoms", *Curr. Opin. Gen. & Devel.*, 10(6):638-643 (2000).
Crossway, A. et al., "Integration of Foreign DNA Following Microinjection of Tobacco Mesophyll Protoplasts", *Mol. Gen. Genet.*, 202(2):179-185 (1986).
Dörmann, P. et al, "Accumulation of Palmitate in Arabidopsis Mediated by the Acyl-Acyl Carrier Protein Thioesterase FATB I", *Plant Physiology*, 123:637-643 (2000).
Fire, A. et al., "Potent and Specific Genetic Interference by Double-Stranded RNA in *Caenorhabditis elegans*", *Nature*, 391:806-811(1998).
Hamada, T. et al., "Modification of Fatty Acid Composition by Over- and Antisense-Expression of a Microsomal ω-3 Fatty Acid Desaturase Gene in Transgenic Tobacco", *Transgenic Research*, 5(2):115-121 (1996).
Matzke, M.A. et al., "RNA-Based Silencing Strategies in Plants", *Curr. Opin. Gen. & Devel.*,11(2):21-227 (2001).
Montgomery, M.K. et al., "RNA as a Target of Double-Stranded RNA-Mediated Genetic Interference in *Caenorhabditis elegans*", *Proc. Natl. Acad. Sci. USA*, 95:15502-15507 (1998).
Sharp, P.A., "RNAi and Double-Strand RNA", *Genes & Development*, 13:139-141 (1999).
Sharp, P.A., "RNA Interference -2001", *Genes & Development*, 15:485-490 (2001).
Supplemental European Search Report in European Application No. 03711656.3 completed Jun. 29, 2005.
Waterhouse, P.M., et al., "Virus Resistance and Gene Silencing in Plants Can Be Induced by Simultaneous Expression of Sense and Antisense RNA", *Proc. Natl. Acad. Sci. USA*, 95:13959-13964 (1998).
Wesley, S.V. et al., "Construct Design for Efficient, Effective and High-Throughput Gene Silencing in Plants", *The Plant Journal*, 27(6):581-590 (2001).
Clark-Walker, G.D., et al., "Location of Transcriptional Control Signals and Transfer RNA Sequences in *Torulopsis glabrata* Mitochondrial DNA", *Embo (European Molecular Biology Organization)journal*, 4(2):465-473 (1985).
Database EM_GSS 'Online! EMBL Heidelberg, Germany; AC AL071390, May 29, 1999, GENOSCOPE: "Drosophila melanogaster genome surface sequence TET3 end of BAC: BACR32M05", XP002163063, abstract.
DATABASE EMPLN 'Online! EMBL Heidelberg, Germany; AC/ID AC004705, May 21, 1998, Lin X et al.: "Sequence and analysis of chromosome 2 of the plant *Arabidopsis thaliana*" XP002163064, abstract.
DATABASE EM_ GSS 'Online! EMBL Heidelberg, Germany; AC AL105179, Jul. 26, 1999, GENOSCOPE: "Drosophila melanogaster genome survey sequence T7 end of BAC: BACN 13A12" XP002163065, abstract.
DATABASE EM-NEW 'Online! EMBL Heidelberg, Germany; AC/ID AB022220, Jan. 15, 1999, Sato S. et al.: "Arabidopsis thaliana genomic DNA, chromosome 3, P1 clone: MLN2 1" XP002163066, abstract.
DATABASE EM_GSS 'Online! EMBL Heidelberg, Germany; AC AL069706, May 29, 1999, GENOSCOPE: "Drosophila melanogaster genome survey sequence T7 end of BAC: BACR29B23" XP002163067, abstract.
DATABASE EM_GSS 'Online! EMBL Heidelberg, Germany; AC AL063932, May 29, 1999, GENOSCOPE; "Drosophila melanogaster genome survey sequence TET3 end of BAC: BACR8010" XP002163068, abstract.
DATABASE EM_GSS 'Online! EMBL Heidelberg, Germany; AC AL108811, Jul. 26, 1999, GENOSCOPE: "Drosophila melanogaster genome survey sequence SP6 end of BAC BACN37D10" XP002163069, abstract.
DATABASE EM_NEW 'Online! EMBL Heidelberg, Germany; AC/ID AB026636, May 7, 1999, Sato S. et al.: "Arabidopsis thaliana genomic DNA, chromosome 3, TAC clone: K14A17", XP002163070, abstract.
DATABASE EMEST_PLN 'Online! EMBL Heidelberg, Germany; AC/ID AW297948, Feb. 8, 2000, Shoemaker R. et al.: "Public soybean EST project", XP002163071, abstract.

DATABASE EMPLN 'Online! EMBL Heidelberg, Germany; AC AL161581, Mar. 15, 2000, Weichselgartner M. et al.: "Arabidopsis thaliana chromosome 4, contig fragment No. 77", XP002163072, abstract.

International Search Report mailed Apr. 9, 2004, issued in PCT/US03/19445.

International Search Report mailed Apr. 26, 2001, issued in PCT/US00/22613.

Lee, Y., et al., "Antisense Expression of the CK2 α-Subunit Gene in Arabidopsis. Effects on Light-Regulated Gene Expression and Plant Growth", *Plant Physiology*, 119:989-1000 (1999).

Lewin, B., "How Did Interrupted Genes Evolve?", *Genes*, 2$^{nd}$ Edition, pp. 333-337.

Okuley, J., et al., "Arabidopsis FAD2 Gene Encodes the Enzyme that is Essential for Polyunsaturated Lipid Synthesis", *The Plant Cell*, 6:147-158 (1994).

Qing, L., Thesis, "The Isolation and Characterisation of Fatty Acid Desaturase Genes in Cotton", University of Sydney, Australia, pp. ii-iv, 24-26, 121-123, 142, 167-168, 172-174, 179-181 (1998).

Levin et al., "Methods of double-standed RNA-mediated gene inactivation in *Arabidopsis* and their use to define an essential gene in methionine biosynthesis," *Plant Molecular Biology*, 44(6):759-775 (2000).

Peele et al., "Silencing of a meristematic gene using geminivirus-derived vectors," *The Plant Journal*, 2(4):357-366 (2001).

Supplementary European Search Report, European Application No. 04 78 5109 (Nov. 7, 2006).

Bouchon et al., "Oil Distribution in Fried Potatoes Monitored by Infrared Microspectroscopy", *Journal of Food Science*, 66(7):918-923 (2001).

Chuang et.al, "Specific and Heritable Genetic Interference by Double-Stranded RNA in *Arabidopsis Thaliana*", *PNAS*, 97(9):4985-4990 (2000).

Colliver et al., "Differential modification of flavonoid and isoflavonoid biosynthesis with an antisense chalcone synthase construct in transgenic *Lotus corniculatus*", *Plant Mol. Biol.*, 35:509-522 (1997).

DeLuca, "Molecular characterization of secondary metabolic pathways", *AgBiotech News and Information*, 5(6):225N-229N (1993).

Hamilton et al., "A Transgene with Repeated DNA Causes High Frequency, Post-Transcriptional Suppression of ACC-Oxidase Gene Expression in Tomato", *The Plant Journal*, 15(6):737-746 (1998).

International Search Report of International Application No. PCT/US2003/019437 dated Jun. 21, 2004.

Jaworski et al., "Industrial oils from transgenic plants", *Current Opinion in Plant Biology*, 6:178-184 (2003).

Singh et al., "Metabolic engineering of new fatty acids in plants", *Current Opinion in Plant Biology*, 8:197-203 (2005).

Smith et al., "Total silencing by intron-spliced hairpin RNAs", *Nature*, 407:319-320 (2000).

Stam et al., "Post-transcriptional silencing of chalcone synthase in *Petunia* by inverted transgene repeats", *The Plant Journal* 12(1):63-82 (1997).

Stoutjeskijk et al., "hpRNA-Mediated Targeting of the Arabidopsis *FAD* 2 Gene Gives Highly Efficient and Stable Silencing", *Plant Physiology*, 129:1723-1731 (2002).

Supplementary Partial European Search Report in Application No. 03 76 1158 dated Jan. 8, 2007.

* cited by examiner

Figure 14

SEQUENCE LISTING

<160> NUMBER OF SEQ ID NOS: 41

<210> SEQ ID NO 1
<211> LENGTH: 420
<212> TYPE: DNA
<213> ORGANISM: Glycine max
<220> FEATURE:
<223> OTHER INFORMATION: FAD2-1A intron 1

<400> SEQUENCE: 1

```
gtaaattaaa ttgtgcctgc acctcgggat atttcatgtg gggttcatca tatttgttga      60
ggaaaagaaa ctcccgaaat tgaattatgc atttatatat ccttttttcat ttctagattt    120 cctgaaggct taggtgtagg cacctagcta gtagctacaa tatcagcact tctctctatt    180
gataaacaat tggctgtaat gccgcagtag aggacgatca caacatttcg tgctggttac    240
tttttgtttt atggtcatga tttcactctc tctaatctct ccattcattt tgtagttgtc    300
attatcttta gattttttcac tacctggttt aaaattgagg gattgtagtt ctgttggtac    360
atattacaca ttcagcaaaa caactgaaac tcaactgaac ttgtttatac tttgacacag    420
```

<210> SEQ ID NO 2
<211> LENGTH: 405
<212> TYPE: DNA
<213> ORGANISM: Glycine max
<220> FEATURE:

```
<223> OTHER INFORMATION: FAD2-1B intron 1

<400> SEQUENCE: 2
gtatgatgct aaattaaatt gtgcctgcac cccaggatat ttcatgtggg attcatcatt      60
tattgaggaa aactctccaa attgaatcgt gcatttatat ttttttttcca tttctagatt    120
tcttgaaggc ttatggtata ggcacctaca attatcagca cttctctcta ttgataaaca    180
attggctgta ataccacagt agagaacgat cacaacattt tgtgctggtt accttttgtt    240
ttatggtcat gatttcactc tctctaatct gtcacttccc tccattcatt ttgtacttct    300
catattttc  acttcctggt tgaaaattgt agttctcttg gtacatacta gtattagaca    360
ttcagcaaca acaactgaac tgaacttctt tatactttga cacag                    405

<210> SEQ ID NO 3
<211> LENGTH: 1704
<212> TYPE: DNA
<213> ORGANISM: Glycine max
<220> FEATURE:
<223> OTHER INFORMATION: FAD2-1B promoter

<400> SEQUENCE: 3
actatagggc acgcgtggtc gacggcccgg gctggtcctc ggtgtgactc agccccaagt      60
gacgccaacc aaacgcgtcc taactaaggt gtagaagaaa cagatagtat ataagtatac    120
catataagag gagagtgagt ggagaagcac ttctcctttt tttttctctg ttgaaattga    180
aagtgttttc cgggaaataa ataaaataaa ttaaaatctt acacactcta ggtaggtact    240
tctaatttaa tccacacttt gactctatat atgttttaaa ataattata atgcgtactt    300
acttcctcat tatactaaat ttaacatcga tgattttatt ttctgtttct cttcttttcca   360
cctacataca tcccaaaatt tagggtgcaa ttttaagttt attaacacat gttttttagct  420
gcatgctgcc tttgtgtgtg ctcaccaaat tgcattcttc tctttatatg ttgtatttga   480
attttcacac catatgtaaa caagattacg tacgtgtcca tgatcaaata caaatgctgt   540
cttatactgg caatttgata aacagccgtc catttttttct ttttctcttt aactatatat 600
gctctagaat ctctgaagat tcctctgcca tcgaattct ttcttggtaa caacgtcgtc    660
gttatgttat tattttattc tattttttat ttatcatata tatttcttat tttgttcgaa    720
gtatgtcata ttttgatcgt gacaattaga ttgtcatgta ggagtaggaa tatcacttta    780
aaacattgat tagtctgtag gcaatattgt cttcttttttc ctcctttatt aatatatttt    840
gtcgaagttt taccacaagg ttgattcgct ttttttgtcc cttctcttg ttcttttttac    900
ctcaggtatt ttagtctttc atggattata agatcactga aagtgtatg catgtaatac    960
taagcaccat agctgttctg cttgaattta tttgtgtgta aattgtaatg tttcagcgtt   1020
ggctttccct gtagctgcta caatggtact gtatatctat ttttttgcatt gttttcattt   1080
tttctttttac ttaatcttca ttgctttgaa attaataaaa caatataata tagttttgaac 1140
tttgaactat tgcctattca tgtaattaac ttattcactg actcttattg tttttctggt   1200
agaattcatt ttaaattgaa ggataaatta agaggcaata cttgtaaatt gacctgtcat   1260
aattacacag gaccctgttt tgtgcctttt tgtctctgtc tttggttttg catgttagcc   1320
tcacacagat atttagtagt tgttctgcat acaagcctca cacgtatact aaaccagtgg   1380
acctcaaagt catggcctta cacctattgc atgcgagtct gtgacacaac ccctggtttc   1440
catattgcaa tgtgctacgc cgtcgtcctt gtttgtttcc atatgtatat tgataccatc   1500
aaattattat atcatttata tggtctggac cattacgtgt actctttatg acatgtaatt   1560
```

```
gagtttttta attaaaaaaa tcaatgaaat ttaactacgt agcatcatat agagataatt    1620
gactagaaat tgatgactt  attctttcct aatcatattt tcttgtattg atagccccgc    1680
tgtccctttt aaactcccga gaga                                           1704
```

<210> SEQ ID NO 4
<211> LENGTH: 4497
<212> TYPE: DNA
<213> ORGANISM: Glycine max
<220> FEATURE:
<223> OTHER INFORMATION: FAD2-1A genomic clone

<400> SEQUENCE: 4

```
cttgcttggt aacaacgtcg tcaagttatt attttgttct tttttttttt atcatatttc      60
ttattttgtt ccaagtatgt catattttga tccatcttga caagtagatt gtcatgtagg     120
aataggaata tcactttaaa ttttaaagca ttgattagtc tgtaggcaat attgtcttct     180
tcttcctcct tattaatatt ttttattctg ccttcaatca ccagttatgg gagatggatg     240
taatactaaa taccatagtt gttctgcttg aagtttagtt gtatagttgt tctgcttgaa     300
gtttagttgt gtgtaatgtt tcagcgttgg cttcccctgt aactgctaca atggtactga     360
atatatattt tttgcattgt tcatttttt cttttactta atcttcattg ctttgaaatt      420
aataaaacaa aagaaggac cgaatagttt gaagtttgaa ctattgccta ttcatgtaac      480
ttattcaccc aatcttatat agttttctg gtagagatca ttttaaattg aaggatataa      540
attaagagga aatacttgta tgtgatgtgt ggcaatttgg aagatcatgc gtagagagtt     600
taatggcagg ttttgcaaat tgacctgtag tcataattac actgggccct ctcggagttt     660
tgtgcctttt tgttgtcgct gtgttggtt ctgcatgtta gcctcacaca gatatttagt      720
agttgttgtt ctgcatataa gcctcacacg tatactaaac gagtgaacct caaaatcatg     780
gccttacacc tattgagtga aattaatgaa cagtgcatgt gagtatgtga ctgtgacaca     840 accccggtt  ttcatattgc aatgtgctac tgtggtgatt aaccttgcta cactgtcgtc     900
cttgtttgtt tccttatgta tattgatacc ataaattatt actagtatat cattttatat     960
tgtccatacc attacgtgtt tatagtctct ttatgacatg taattgaatt ttttaattat    1020
aaaaaataat aaaacttaat tacgtactat aaagagatgc tcttgactag aattgtgatc    1080
tcctagtttc ctaaccatat actaatattt gcttgtattg atagcccctc cgttcccaag    1140
agtataaaac tgcatcgaat aatacaagcc actaggcatg gtaaattaaa ttgtgcctgc    1200
acctcgggat atttcatgtg gggttcatca tatttgttga ggaaagaaa  ctcccgaaat    1260 tgaattatgc atttatatat cctttttcat ttctagattt cctgaaggct taggtgtagg    1320
cacctagcta gtagctacaa tatcagcact ctctctatt  gataaacaat tggctgtaat    1380
gccgcagtag aggacgatca caacatttcg tgctggttac tttttgtttt atggtcatga    1440
tttcactctc tctaatctct ccattcattt tgtagttgtc attatcttta gatttttcac    1500
tacctggttt aaaattgagg gattgtagtt ctgttggtac atattacaca ttcagcaaaa    1560
caactgaaac tcaactgaac ttgtttatac tttgacacag ggtctagcaa aggaaacaac    1620
aatgggaggt agaggtcgtg tggcaaagtg gaagttcaag ggaagaagcc tctctcaagg    1680
gttccaaaca caaagccacc attcactgtt ggccaactca agaaagcaat tccaccacac    1740
tgctttcagc gctcccctcct cacttcattc tcctatgttg tttatgacct ttcatttgcc    1800
ttcatttctc acattgccac cacctacttc cacctccttc ctcaaccctt ttccctcatt    1860
```

```
gcatggccaa tctattgggt tctccaaggt tgccttctca ctggtgtgtg ggtgattgct    1920
cacgagtgtg gtcaccatgc cttcagcaag taccaatggg ttgatgatgt tgtgggtttg    1980
acccttcact caacactttt agtcccttat ttctcatgga aaataagcca tcgccgccat    2040
cactccaaca caggttccct tgaccgtgat gaagtgtttg tcccaaaacc aaaatccaaa    2100
gttgcatggt tttccaagta cttaaacaac cctctaggaa gggctgtttc tcttctcgtc    2160
acactcacaa tagggtggcc tatgtattta gccttcaatg tctctggtag acccatatgat   2220
agttttgcaa gccactacca cccttatgct cccatatatt ctaaccgtga gaggcttctg    2280
atctatgtct ctgatgttgc tttgtttttct gtgacttact ctctctaccg tgttgcaacc   2340
ctgaaagggt tggtttggct gctatgtgtt tatggggtgc ctttgctcat tgtgaacggt    2400
tttcttgtga ctatcacata tttgcagcac acacactttg ccttgcctca ttacgattca    2460
tcagaatggg actggctgaa gggagctttg gcaactatgg acagagatta tgggattctg    2520
aacaaggtgt ttcatcacat aactgatact catgtggctc accatctctt ctctacaatg    2580
ccacattacc atgcaatgga ggcaaccaat gcaatcaagc caatattggg tgagtactac    2640
caatttgatg acacaccatt ttacaaggca ctgtggagag aagcgagaga gtgcctctat    2700
gtggagccag atgaaggaac atccgagaag ggcgtgtatt ggtacaggaa caagtattga    2760
tggagcaacc aatgggccat agtgggagtt atggaagttt tgtcatgtat tagtacataa    2820
ttagtagaat gttataaata agtggatttg ccgcgtaatg actttgtgtg tattgtgaaa    2880
cagcttgttg cgatcatggt tataatgtaa aaataattct ggtattaatt acatgtggaa    2940
agtgttctgc ttatagcttt ctgcctaaaa tgcacgctgc acgggacaat atcattggta    3000
attttttttaa aatctgaatt gaggctactc ataatactat ccataggaca tcaaagacat    3060
gttgcattga ctttaagcag aggttcatct agaggattac tgcataggct tgaactacaa    3120
gtaatttaag ggacgagagc aactttagct ctaccacgtc gttttacaag gttattaaaa    3180
tcaaattgat cttattaaaa ctgaaaattt gtaataaaat gctattgaaa aattaaaata    3240
tagcaaacac ctaaattgga ctgattttta gattcaaatt taataattaa tctaaattaa    3300
acttaaattt tataatatat gtcttgtaat atatcaagtt tttttttttta ttattgagtt    3360
tggaaacata taataaggaa cattagttaa tattgataat ccactaagat cgacttagta    3420
ttacagtatt tggatgattt gtatgagata ttcaaacttc actcttatca aatagagac    3480
aaaagttaat actgatggtg gagaaaaaaa aatgttattg ggagcatatg gtaagataag    3540
acggataaaa atatgctgca gcctggagag ctaatgtatt ttttggtgaa gttttcaagt    3600
gacaactatt catgatgaga acacaataat attttctact tacctatccc acataaaata    3660
ctgattttaa taatgatgat aaataatgat taaaatattt gattctttgt taagagaaat    3720
aaggaaaaca taaatattct catggaaaaa tcagcttgta ggagtagaaa ctttctgatt    3780
ataattttaa tcaagtttaa ttcattcttt taattttatt attagtacaa aatcattctc    3840
ttgaatttag agatgtatgt tgtagcttaa tagtaatttt ttatttttat aataaaattc    3900
aagcagtcaa atttcatcca aataatcgtg ttcgtgggtg taagtcagtt attccttctt    3960
atcttaatat acacgcaaag gaaaaaataa aaataaaatt cgaggaagcg cagcagcagc    4020
tgataccacg ttggttgacg aaactgataa aaagcgctgt cattgtgtct ttgtttgatc    4080
atcttcacaa tcacatctcc agaacacaaa gaagagtgac ccttcttctt gttattccac    4140
ttgcgttagg tttctacttt cttctctctc tctctctctc tcttcattcc tcattttttcc   4200
ctcaaacaat caatcaattt tcattcagat tcgtaaattt ctcgattaga tcacggggtt    4260
```

```
aggtctccca ctttatcttt tcccaagcct ttctctttcc ccctttccct gtctgcccca    4320
taaaattcag gatcggaaac gaactgggtt cttgaatttc actctagatt ttgacaaatt    4380
cgaagtgtgc atgcactgat gcgacccact cccccttttt tgcattaaac aattatgaat    4440
tgaggttttt cttgcgatca tcattgcttg aattgaatca tattaggttt agattct       4497

<210> SEQ ID NO 5
<211> LENGTH: 206
<212> TYPE: DNA
<213> ORGANISM: Glycine max
<220> FEATURE:
<223> OTHER INFORMATION: FAD2-1A 3'UTR

<400> SEQUENCE: 5
tggagcaacc aatgggccat agtgggagtt atggaagttt tgtcatgtat agtacataa     60 ttagtagaat gttataaata agtggatttg ccgcgtaatg actttgtgtg tattgtgaaa    120
cagcttgttg cgatcatggt tataatgtaa aaataattct ggtattaatt acatgtggaa    180
agtgttctgc ttatagcttt ctgcct                                         206

<210> SEQ ID NO 6
<211> LENGTH: 125
<212> TYPE: DNA
<213> ORGANISM: Glycine max
<220> FEATURE:
<223> OTHER INFORMATION: FAD2-1A 5'UTR

<400> SEQUENCE: 6
ccatatacta atatttgctt gtattgatag cccctccgtt cccaagagta taaaactgca    60
tcgaataata caagccacta ggcatgggtc tagcaaagga acaacaatg ggaggtagag     120 gtcgt                                                                125

<210> SEQ ID NO 7
<211> LENGTH: 191
<212> TYPE: DNA
<213> ORGANISM: Glycine max
<220> FEATURE:
<223> OTHER INFORMATION: FAD3-1A intron 1

<400> SEQUENCE: 7
gtaataattt ttgtgtttct tactcttttt ttttttttt tgtttatgat atgaatctca     60
cacattgttc tgttatgtca tttcttcttc atttggcttt agacaactta aatttgagat    120
ctttattatg ttttttgctta tatggtaaag tgattcttca ttatttcatt cttcattgat   180
tgaattgaac a                                                         191

<210> SEQ ID NO 8
<211> LENGTH: 346
<212> TYPE: DNA
<213> ORGANISM: Glycine max
<220> FEATURE:
<223> OTHER INFORMATION: FAD3-1A intron 2

<400> SEQUENCE: 8
ttagttcata ctggcttttt tgtttgttca tttgtcattg aaaaaaaatc ttttgttgat    60
tcaattattt ttatagtgtg tttggaagcc cgtttgagaa aataagaaat cgcatctgga   120
atgtgaaagt tataactatt tagcttcatc tgtcgttgca agttctttta ttggttaaat   180
ttttatagcg tgctaggaaa cccattcgag aaaataagaa atcacatctg gaatgtgaaa   240
```

```
gttataactg ttagcttctg agtaaacgtg gaaaaaccac attttggatt tggaaccaaa      300
ttttatttga taaatgacaa ccaaattgat tttgatggat tttgca                    346
```

<210> SEQ ID NO 9
<211> LENGTH: 142
<212> TYPE: DNA
<213> ORGANISM: Glycine max
<220> FEATURE:
<223> OTHER INFORMATION: FAD3-1A intron 3A

<400> SEQUENCE: 9

```
gtatgtgatt aattgcttct cctatagttg ttcttgattc aattacattt tatttatttg      60
gtaggtccaa gaaaaaaggg aatctttatg cttcctgagg ctgttcttga acatggctct     120
tttttatgtg tcattatctt ag                                              142
```

<210> SEQ ID NO 10
<211> LENGTH: 1228
<212> TYPE: DNA
<213> ORGANISM: Glycine max
<220> FEATURE:
<223> OTHER INFORMATION: FAD3-1A intron 4

<400> SEQUENCE: 10

```
taacaaaaat aaatagaaaa tagtgggtga acacttaaat gcgagatagt aatacctaaa      60
aaagaaaaaa aatataggta taataaataa tataactttc aaaataaaaa gaaatcatag     120
agtctagcgt agtgtttgga gtgaaatgat gttcacctac cattactcaa agattttgtt     180
gtgtccctta gttcattctt attattttac atatcttact tgaaaagact ttttaattat     240
tcattgagat cttaaagtga ctgttaaatt aaaataaaaa acaagtttgt taaaacttca     300
aataaataag agtgaaggga gtgtcatttg tcttctttct tttattgcgt tattaatcac     360
gtttctcttc tcttttttt ttttcttctc tgctttccac ccattatcaa gttcatgtga     420
agcagtggcg gatctatgta aatgagtggg gggcaattgc acccacaaga ttttattttt     480
tatttgtaca ggaataataa aataaaactt gcccccata aaaataaat atttttctt      540 aaaataatgc aaaataaata taagaaataa aaagagaata aattattatt aattttatta     600
ttttgtactt tttatttagt ttttttagcg gttagatttt tttttcatga cattatgtaa     660
tcttttaaaa gcatgtaata tttttatttt gtgaaaataa atataaatga tcatattagt     720
ctcagaatgt ataaactaat aataatttta tcactaaaag aaattctaat ttagtccata     780
aataagtaaa acaagtgaca attatatttt atatttactt aatgtgaaat aatacttgaa     840
cattataata aaacttaatg acaggagata ttacatagtg ccataaagat attttaaaaa     900
ataaaatcat taatacactg tactactata taatattcga tatatatttt taacatgatt     960
ctcaatagaa aaattgtatt gattatattt tattagacat gaatttacaa gccccgtttt    1020
tcatttatag ctcttacctg tgatctattg ttttgcttcg ctgtttttgt tggtcaaggg    1080
acttagatgt cacaatatta atactagaag taaatattta tgaaaacatg taccttacct    1140
caacaaagaa agtgtggtaa gtggcaacac acgtgttgca tttttggccc agcaataaca    1200 cgtgttttg tggtgtacta aaatggac                                       1228
```

<210> SEQ ID NO 11
<211> LENGTH: 625
<212> TYPE: DNA
<213> ORGANISM: Glycine max
<220> FEATURE:
<223> OTHER INFORMATION: FAD3-1A intron 5

-continued

<400> SEQUENCE: 11

```
gtacattttta ttgcttattc acctaaaaac aatacaatta gtacatttgt tttatctctt      60
ggaagttagt cattttcagt tgcatgattc taatgctctc tccattctta aatcatgttt     120
tcacacccac ttcatttaaa ataagaacgt gggtgttatt ttaatttcta ttcactaaca     180
tgagaaatta acttatttca agtaataatt ttaaaatatt tttatgctat tattttatta     240
caaataatta tgtatattaa gtttattgat tttataataa ttatattaaa attatatcga     300
tattaatttt tgattcactg atagtgtttt atattgttag tactgtgcat ttattttaaa     360
attggcataa ataatatatg taaccagctc actatactat actgggagct tggtggtgaa     420
aggggttccc aaccctcctt tctaggtgta catgctttga tacttctggt accttcttat     480
atcaatataa attatatttt gctgataaaa aaacatggtt aaccattaaa ttctttttt      540
aaaaaaaaaa ctgtatctaa actttgtatt attaaaaga agtctgagat taacaataaa      600
ctaacactca tttggattca ctgca                                           625
```

<210> SEQ ID NO 12
<211> LENGTH: 98
<212> TYPE: DNA
<213> ORGANISM: Glycine max
<220> FEATURE:
<223> OTHER INFORMATION: FAD3-1A intron 3B

<400> SEQUENCE: 12

```
ggtgagtgat ttttgactt ggaagacaac aacacattat tattataata tggttcaaaa      60
caatgacttt ttctttatga tgtgaactcc atttttta                              98
```

<210> SEQ ID NO 13
<211> LENGTH: 115
<212> TYPE: DNA
<213> ORGANISM: Glycine max
<220> FEATURE:
<223> OTHER INFORMATION: FAD3-1A intron 3C

<400> SEQUENCE: 13

```
ggtaactaaa ttactcctac attgttactt tttcctcctt tttttttatta tttcaattct     60
ccaattggaa atttgaaata gttaccataa ttatgtaatt gtttgatcat gtgca          115
```

<210> SEQ ID NO 14
<211> LENGTH: 1037
<212> TYPE: DNA
<213> ORGANISM: Glycine max
<220> FEATURE:
<223> OTHER INFORMATION: Fad3-1C intron 4

<400> SEQUENCE: 14

```
gtaacaaaaa taaatagaaa aatagtgagtg aacacttaaa tgttagatac taccttcttc     60
ttcttttttt tttttttttt gaggttaatg ctagataata gctagaaaga gaaagaaaga    120
caaatatagg taaaaataaa taatataacc tgggaagaag aaaacataaa aaagaaata    180
atagagtcta cgtaatgttt ggattttga gtgaaatggt gttcacctac cattactcaa    240
agattctgtt gtctacgtag tgtttggact tggagtgaa atggtgttca cctaccatta    300
ctcagattct gttgtgtccc ttagttactg tcttatattc ttagggtata ttctttattt    360
tacatccttt tcacatctta cttgaaaaga ttttaattat tcattgaaat attaacgtga    420
cagttaaatt aaaataataa aaaattcgtt aaaacttcaa ataaataaga gtgaaaggat    480
```

-continued

| | |
|---|---|
| catcattttt cttctttctt ttattgcgtt attaatcatg cttctcttct ttttttttctt | 540 |
| cgctttccac ccatatcaaa ttcatgtgaa gtatgagaaa atcacgattc aatggaaagc | 600 |
| tacaggaacy tttttttgttt tgttttttata atcggaatta atttatactc catttttttca | 660 |
| caataaatgt tacttagtgc cttaaagata atatttgaaa aattaaaaaa attattaata | 720 |
| cactgtacta ctatataata tttgacatat atttaacatg attttctatt gaaaatttgt | 780 |
| atttattatt ttttaatcaa aacccataag gcattaattt acaagaccca ttttttcattt | 840 |
| atagctttac ctgtgatcat ttatagcttt aagggactta gatgttacaa tcttaattac | 900 |
| aagtaaatat ttatgaaaaa catgtgtctt acccccttaac cttacctcaa caaagaaagt | 960 |
| gtgataagtg gcaacacacg tgttgctttt ttggcccagc aataacacgt gttttttgtgg | 1020 |
| tgtacaaaaa tggacag | 1037 |

<210> SEQ ID NO 15
<211> LENGTH: 4010
<212> TYPE: DNA
<213> ORGANISM: Glycine max
<220> FEATURE:
<223> OTHER INFORMATION: partial FAD3-1A genomic clone

<400> SEQUENCE: 15

| | |
|---|---|
| acaaagcctt tagcctatgc tgccaataat ggataccaac aaaagggttc ttcttttgat | 60 |
| tttgatccta gcgctcctcc accgtttaag attgcagaaa tcagagcttc aataccaaaa | 120 |
| cattgctggg tcaagaatcc atggagatcc ctcagttatg ttctcaggga tgtgcttgta | 180 |
| attgctgcat tggtggctgc agcaattcac ttcgacaact ggcttctctg gctaatctat | 240 |
| tgccccattc aaggcacaat gttctgggct ctctttgttc ttggacatga ttggtaataa | 300 |
| ttttttgtgtt tcttactctt tttttttttt ttttgtttat gatatgaatc tcacacattg | 360 |
| ttctgttatg tcatttcttc ttcatttggc tttagacaac ttaaatttga gatctttatt | 420 |
| atgttttttgc ttatatggta aagtgattct tcattatttc attcttcatt gattgaattg | 480 |
| aacagtggcc atgaaagctt ttcagatagc cctttgctga atagcctggt gggacacatc | 540 |
| ttgcattcct caattcttgt gccataccat ggatggtag ttcatactgg cttttttgtt | 600 |
| tgttcatttg tcattgaaaa aaaatctttt gttgattcaa ttatttttat agtgtgtttg | 660 |
| gaagcccgtt tgagaaaata agaaatcgca tctggaatgt gaaagttata actatttagc | 720 |
| ttcatctgtc gttgcaagtt ctttttattgg ttaaattttt atagcgtgct aggaaaccca | 780 |
| ttcgagaaaa taagaaatca catctggaat gtgaaagtta taactgttag cttctgagta | 840 |
| aacgtggaaa aaccacattt tggatttgga accaaatttt atttgataaa tgacaaccaa | 900 |
| attgattttg atggattttg caggagaatt agccacagaa ctcaccatga aaccatgga | 960 |
| cacattgaga aggatgagtc atgggttcca gtatgtgatt aattgcttct cctatagttg | 1020 |
| ttcttgattc aattacattt tatttatttg gtaggtccaa gaaaaaggg aatctttatg | 1080 |
| cttcctgagg ctgttcttga acatggctct tttttatgtg tcattatctt agttaacaga | 1140 |
| gaagatttac aagaatctag acagcatgac aagactcatt agattcactg tgccatttcc | 1200 |
| atgtttgtgt atccaattta tttggtgagt gattttttga cttggaagac aacaacacat | 1260 |
| tattattata atatggttca aaacaatgac ttttctctta tgatgtgaac tccattttt | 1320 |
| agttttcaag aagccccgga aggaaggct ctcacttcaa tccctacagc aatctgtttc | 1380 |
| cacccagtga gagaaaagga atagcaatat caacactgtg ttgggctacc atgttttctc | 1440 |
| tgcttatcta tctctcattc attaactagt ccacttctag tgctcaagct ctatggaatt | 1500 |

```
ccatattggg taactaaatt actcctacat tgttactttt tcctccttt ttttattatt      1560
tcaattctcc aattggaaat ttgaaatagt taccataatt atgtaattgt ttgatcatgt      1620
gcagatgttt gttatgtggc tggactttgt cacatacttg catcaccatg gtcaccacca      1680
gaaactgcct tggtaccgcg gcaaggtaac aaaaataaat agaaatagt gggtgaacac       1740
ttaaatgcga gatagtaata cctaaaaaaa gaaaaaaata taggtataat aaataatata      1800
actttcaaaa taaaagaaa tcatagagtc tagcgtagtg tttggagtga atgatgttc        1860
acctaccatt actcaaagat tttgttgtgt cccttagttc attcttatta ttttacatat      1920
cttacttgaa aagactttt aattattcat tgagatctta aagtgactgt taaattaaaa       1980
taaaaaacaa gtttgttaaa acttcaaata aataagagtg aagggagtgt catttgtctt      2040
cttctttta ttgcgttatt aatcacgttt ctcttctctt tttttttt cttctctgct         2100
ttccacccat tatcaagttc atgtgaagca gtggcggatc tatgtaaatg agtgggggc      2160
aattgcaccc acaagatttt attttttatt tgtacaggaa taataaaata aactttgcc      2220
cccataaaaa ataaatattt tttcttaaaa taatgcaaaa taaatataag aaataaaaag     2280
agaataaatt attattaatt ttattatttt gtactttta tttagttttt ttagcggtta     2340
gatttttttt tcatgacatt atgtaatctt ttaaaagcat gtaatatttt tattttgtga    2400
aaataaatat aaatgatcat attagtctca gaatgtataa actaataata attttatcac   2460
taaaagaaat tctaatttag tccataaata agtaaaacaa gtgacaatta tattttatat    2520
ttacttaatg tgaaataata cttgaacatt ataataaaac ttaatgacag gagatattac    2580
atagtgccat aaagatattt taaaaaataa aatcattaat acactgtact actatataat    2640
attcgatata tattttaac atgattctca atagaaaaat tgtattgatt atattttatt     2700
agacatgaat ttacaagccc cgtttttcat ttatagctct tacctgtgat ctattgtttt    2760
gcttcgctgt ttttgttggt caagggactt agatgtcaca atattaatac tagaagtaaa    2820
tatttatgaa aacatgtacc ttacctcaac aaagaaagtg tggtaagtgg caacacacgt    2880
gttgcatttt tggcccagca ataacacgtg tttttgtggt gtactaaaat ggacaggaat    2940
ggagttattt aagaggtggc ctcaccactg tggatcgtga ctatggttgg atcaataaca   3000
ttcaccatga cattggcacc catgttatcc accatctttt cccccaaatt cctcattatc    3060
acctcgttga agcggtacat tttattgctt attcacctaa aaacaataca attagtacat    3120
ttgttttatc tcttggaagt tagtcatttt cagttgcatg attctaatgc tctctccatt    3180
cttaaatcat gttttcacac ccacttcatt taaaataaga acgtgggtgt tattttaatt    3240
tctattcact aacatgagaa attaacttat ttcaagtaat aattttaaaa tattttatg     3300
ctattatttt attacaaata attatgtata ttaagtttat tgattttata ataattatat    3360
taaaattata tcgatattaa ttttgattc actgatagtg ttttatattg ttagtactgt     3420
gcatttattt taaaattggc ataaataata tatgtaacca gctcactata ctatactggg    3480
agcttggtgg tgaagggggt tcccaaccct ccttctagg tgtacatgct ttgatacttc     3540
tggtaccttc ttatatcaat ataaattata ttttgctgat aaaaaaacat ggttaaccat    3600
taaattctt ttttaaaaaa aaaactgtat ctaaactttg tattattaaa aagaagtctg     3660
agattaacaa taaactaaca ctcatttgga ttcactgcag acacaagcag caaaaccagt   3720
tcttggagat tactaccgtg agccagaaag atctgcgcca ttaccatttc atctaataaa    3780
gtatttaatt cagagtatga gacaagacca cttcgtaagt gacactggag atgttgttta    3840
```

-continued

```
ttatcagact gattctctgc tcctccactc gcaacgagac tgagtttcaa acttttgggg    3900
ttattattta ttgattctag ctactcaaat tacttttttt ttaatgttat gttttttgga    3960
gtttaacgtt ttctgaacaa cttgcaaatt acttgcatag agagacatgg               4010
```

<210> SEQ ID NO 16
<211> LENGTH: 184
<212> TYPE: DNA
<213> ORGANISM: Glycine max
<220> FEATURE:
<223> OTHER INFORMATION: FAD3-1A 3'UTR

<400> SEQUENCE: 16

```
gtttcaaact ttttgggtta ttatttattg gattctagct actcaaatta cttttttttt     60
aatgttatgt ttttggagt ttaacgtttt ctgaacaact tgcaaattac ttgcatagag     120
agacatggaa tatttatttg aaattagtaa ggtagtaata ataaattttg aattgtcagt    180
ttca                                                                  184
```

<210> SEQ ID NO 17
<211> LENGTH: 143
<212> TYPE: DNA
<213> ORGANISM: Glycine max
<220> FEATURE:
<223> OTHER INFORMATION: FAD3-1A 5'UTR

<400> SEQUENCE: 17

```
tgcggttata taaatgcact atcccataag agtattttc gaagatttcc ttcttcctat      60
tctaggtttt tacgcaccac gtatccctga gaaaagagag gaaccacact ctctaagcca    120
aagcaaaagc agcagcagca gca                                             143
```

<210> SEQ ID NO 18
<211> LENGTH: 2683
<212> TYPE: DNA
<213> ORGANISM: Glycine max
<220> FEATURE:
<223> OTHER INFORMATION: partial FAD3-1B genomic clone

<400> SEQUENCE: 18

```
gttcaagcac agcctctaca acatgttggt aatggtgcag ggaaagaaga tcaagcttat      60
tttgatccaa gtgctccacc acccttcaag attgcaaata tcagagcagc aattccaaaa    120
cattgctggg agaagaacac attgagatct ctgagttatg ttctgaggga tgtgttggta    180
gtgactgcat tggtagctgc agcaatcggc ttcaatagct ggttcttctg gccactctat    240
tggcctgcac aaggcacaat gttttgggca cttttgttc ttggacatga ttggtaacta    300
attattatta caaattgtta tgttatgtta tgttatgttg ttgtgccttt ttctcagtga    360
tgctttagtc atttcatttc acttggttat gcatgattgt tcgttcatat gttctgtcat    420
ggtgagttct aatttgattg atgcatggaa cagtggtcat ggaagttttt caaacagtcc    480
tttgttgaac agcattgtgg gccacatctt gcactcttca attcttgtac cataccatgg    540
atggtcggtt cctttagca acttttcatg ttcactttgt ccttaaattt ttttttatgt    600
ttgttaaaaa atctttggtc tgatttaaca acctaaccat ttttacaact catggatttt    660
ttgcaggaga attagccaca ggactcacca tcagaaccat ggccatgttg agaaggatga    720
atcatgggtt ccggtattac tatgagtttg cttgattaat ttccacattt tttctttctt    780 cttaattttta atcagtggtt agatttggtt gtgttccgat agaagaaaag gggtatctaa    840
gagagatgtg aatttcatga agtggttcat gattatgtgt cttatgcct ttatgtcagc    900
```

```
ttacagagaa agtttacaag aatctagaca acatgacaag aatgatgaga ttcactcttc      960
ctttccccat ctttgcatac ccctttttatt tggtgagacc ctcttttcc agaatgacag     1020
cattatttta ctatatagta cctcaatttt tatatttcta aaattttgaa ttcttgaaat     1080
tgaaaggaaa ggactttatt gggtctagca tctcactctc tctttgtgat atgaaccata     1140
tatttcagtg gagcagaagc cctggaaaag aaggctctca tttcaaccct tacagcaact     1200
tgttctctcc tggtgagaga agagatgtgc taacttcaac tctatgttgg ggcatcatgc     1260
tttctgtgct tctctatctt tccctcacaa tgggtccact ttttatgctc aagctctatg     1320
gggttcccta tttggtaatc tcactctcac actttcttta tacatcgcac gccagtgtgg     1380
gttatttgca acctacaccg aagtaatgcc ctataattaa tgaggttaac acatgtccaa     1440
gtccaatatt ttgttcactt atttgaactt gaacatgtgt agatcttcgt catgtggctg     1500
gatttcgtca cgtacttgca tcatcatggt tacaagcaga aactgccttg gtaccgtggc     1560
caggtatccc atttaacaca atttgtttca ttaacatttt aagagaattt ttttttcaaa     1620
atagttttcg aaattaagca aataccaagc aaattgttag atctacgctt gtacttgttt     1680
taaagtcaaa ttcatgacca aattgtcctc acaagtccaa accgtccact attttatttt     1740
cacctacttt atagcccaat ttgccatttg gttacttcag aaaagagaac cccatttgta     1800
gtaaatatat tatttatgaa ttatggtagt ttcaacataa aacatactta tgtgcagttt     1860
tgccatcctt caaaagaagg tagaaactta ctccatgtta ctctgtctat atgtaatttc     1920
acaggaatgg agtatctaa ggggtggtct tacaacagta gatcgcgact atggttggat     1980
caacaacatt caccatgaca ttggcaccca tgttatccat cacctttttcc ctcaaattcc     2040
acattatcat ttaatcgaag cggtattaat tctctatttc acaagaaatt attgtatgtc     2100
tgcctatgtg atctaagtca attttcacat aacacatgat caaactttct taattctttc     2160
ttctaaattg aaaagtgga ttatatgtca attgaaaatt ggtcaagacc acaaacatgt     2220
gatgatctcc caccttacat ataataattt ctcctattct acaatcaata atccttctat     2280
ggtcctgaat tgttccttc ttttttcatt ttcttattct ttttgttgtc ccacaataga     2340
ctaaagcagc aaaggcagtg ctaggaaagt attatcgtga gcctcagaaa tctgggccat     2400
tgccacttca tctaataaag tacttgctcc acagcataag tcaggatcac ttcgttagcg     2460
actctggcga cattgtgtac taccagactg attcccagct ccacaaagat tcttggaccc     2520
agtccaacta aagttttga tgctacattt acctatttca ctcttaaata ctatttccta     2580
tgtaatatgt aatttagaat atgttaccta ctcaaatcaa ttaggtgaca tgtataagct     2640
ttcataaatt atgctagaaa tgcacttact tttcaaagca tgc                       2683
```

<210> SEQ ID NO 19
<211> LENGTH: 160
<212> TYPE: DNA
<213> ORGANISM: Glycine max
<220> FEATURE:
<223> OTHER INFORMATION: FAD3-1B intron 1

<400> SEQUENCE: 19

```
gtaactaatt attattacaa attgttatgt tatgttatgt tatgttgttg tgcctttttc       60
tcagtgatgc tttagtcatt tcatttcact tggttatgca tgattgttcg ttcatatgtt      120
ctgtcatggt gagttctaat ttgattgatg catggaacag                             160
```

<210> SEQ ID NO 20

<210> SEQ ID NO 20
<211> LENGTH: 119
<212> TYPE: DNA
<213> ORGANISM: Glycine max
<220> FEATURE:
<223> OTHER INFORMATION: FAD3-1B intron 2

<400> SEQUENCE: 20 gttccttta gcaactttc atgttcactt tgtccttaaa ttttttttta tgtttgttaa    60
aaaatctttg gtctgattta acaacctaac cattttaca actcatggat tttttgcag   119

<210> SEQ ID NO 21
<211> LENGTH: 166
<212> TYPE: DNA
<213> ORGANISM: Glycine max
<220> FEATURE:
<223> OTHER INFORMATION: FAD3-1B intron 3a

<400> SEQUENCE: 21
gtattactat gagtttgctt gattaattc cacattttt ctttcttctt aattttaatc    60
agtggttaga tttggttgtg ttccgataga agaaaagggg gtatctagag agatgtgaat  120
ttcatgaagt ggttcatgat tatgtgtctt tatgccttta tgtcag                166

<210> SEQ ID NO 22
<211> LENGTH: 156
<212> TYPE: DNA
<213> ORGANISM: Glycine max
<220> FEATURE:
<223> OTHER INFORMATION: FAD3-1B intron 3b

<400> SEQUENCE: 22
gtgagaccct ctttttccag aatgacagca ttattttact atatagtacc tcaattttta   60
tatttctaaa attttgaatt cttgaaattg aaaggaaagg actttattgg gtctagcatc  120
tcactctctc tttgtgatat gaaccatata tttcag                            156

<210> SEQ ID NO 23
<211> LENGTH: 148
<212> TYPE: DNA
<213> ORGANISM: Glycine max
<220> FEATURE:
<223> OTHER INFORMATION: FAD3-1B intron 3c

<400> SEQUENCE: 23
gtaatctcac tctcacactt tctttataca tcgcacgcca gtgtgggtta tttgcaacct   60
acaccgaagt aatgccctat aattaatgag gttaacacat gtccaagtcc aatattttgt  120
tcacttattt gaacttgaac atgtgtag                                     148

<210> SEQ ID NO 24
<211> LENGTH: 351
<212> TYPE: DNA
<213> ORGANISM: Glycine max
<220> FEATURE:
<223> OTHER INFORMATION: FAD3-1B intron 4

<400> SEQUENCE: 24
taacacaatt tgtttcatta acatttaag agaattttt tttcaaaata gttttcgaaa    60
ttaagcaaat accaagcaaa ttgttagatc tacgcttgta cttgttttaa agtcaaattc  120
atgaccaaat tgtcctcaca agtccaaacc gtccactatt ttatttcac ctactttata  180 gcccaatttg ccatttggtt acttcagaaa agagaacccc atttgtagta aatatattat  240
ttatgaatta tggtagtttc aacataaaac atacttatgt gcagttttgc catccttcaa  300
aagaaggtag aaacttactc catgttactc tgtctatatg taatttcaca g            351

<210> SEQ ID NO 25
<211> LENGTH: 277
<212> TYPE: DNA
<213> ORGANISM: Glycine max
<220> FEATURE:
<223> OTHER INFORMATION: FAD3-1B intron 5

<400> SEQUENCE: 25
gtattaattc tctatttcac aagaaattat tgtatgtctg cctatgtgat ctaagtcaat    60
tttcacataa cacatgatca aactttctta attctttctt ctaaattgaa aaagtggatt   120
atatgtcaat tgaaaattgg tcaagaccac aaacatgtga tgatctccca ccttacatat   180
aataatttct cctattctac aatcaataat ccttctatgg tcctgaattg ttcctttctt   240
ttttcatttt cttattcttt tgttgtccc acaatag                             277

<210> SEQ ID NO 26
<211> LENGTH: 158
<212> TYPE: DNA
<213> ORGANISM: Glycine max
<220> FEATURE:
<223> OTHER INFORMATION: FAD3-1B 3'UTR

<400> SEQUENCE: 26 agttttgat gctacattta cctatttcac tcttaaatac tatttcctat gtaatatgta    60
atttagaata tgttacctac tcaaatcaat taggtgacat gtataagctt tcataaatta   120
tgctagaaat gcacttactt ttcaaagcat gctatgtc                           158

<210> SEQ ID NO 27
<211> LENGTH: 83
<212> TYPE: DNA
<213> ORGANISM: Glycine max
<220> FEATURE:
<223> OTHER INFORMATION: FAD3-1B 5'UTR

<400> SEQUENCE: 27
tctaatacga ctcactatag ggcaagcagt ggtatcaacg cagagtacgc gggggtaaca    60
gagaaagaaa catttgagca aaa                                            83

<210> SEQ ID NO 28
<211> LENGTH: 4083
<212> TYPE: DNA
<213> ORGANISM: Glycine max
<220> FEATURE:
<223> OTHER INFORMATION: FATB genomic clone

<400> SEQUENCE: 28
gggaaacaac aaggacgcaa aatgacacaa tagcccttct tccctgtttc cagcttttct    60
ccttctctct ctccatcttc ttcttcttct tcactcagtc aggtacgcaa acaaatctgc   120
tattcattca ttcattcctc tttctctctg atcgcaaact gcacctctac gctccactct   180 tctcatttc tcttcctttc tcgcttctca gatccaactc tcagataac acaagaccaa    240 acccgctttt tctgcatttc tagactagac gttctaccgg agaaggttct cgattctttt   300
ctcttttaac tttatttta aaataataat aatgagagct ggatgcgtct gttcgttgtg   360
aatttcgagg caatgggggtt tcatttttcg ttacagttac agattgcatt gtctgctttc   420
ctcttctccc ttgtttcttt gccttgtctg atttttcgtt tttatttctt acttttaatt    480

```
tttggggatg gatatttttt ctgcattttt tcggtttgcg atgttttcag gattccgatt      540
ccgagtcaga tctgcgccgg cttatacgac gaatttgttc ttattcgcaa cttttcgctt      600
gattggcttg ttttacctct ggaatctcac acgtgatcaa ataagcctgc tattttagtt      660
gaagtagaat tgttctttta tcggaaagaa ttctatggat ctgttctgaa attggagcta      720
ctgtttcgag ttgctatttt ttttagtagt attaagaaca agtttgcctt ttattttaca      780 ttttttttcct ttgcttttgc caaaagtttt tatgatcact ctcttctgtt tgtgatataa     840
ctgatgtgct gtgctgttat tatttgttat ttggggtgaa gtaattttt ttgggtgaac       900 ttggagcatt tttagtccga ttgatttctc gatatcattt aaggctaagg ttgacctcta      960
ccacgcgttt gcgtttgatg tttttttccat tttttttta tctcatatct tttacagtgt     1020
ttgcctattt gcatttctct tctttatccc ctttctgtgg aaaggtggga gggaaaatgt     1080
attttttttt tctcttctaa cttgcgtata ttttgcatgc agcgacctta gaaattcatt     1140
atggtggcaa cagctgctac ttcatcattt ttccctgtta cttcaccctc gccggactct     1200
ggtggagcag gcagcaaact tggtggtggg cctgcaaacc ttggaggact aaaatccaaa     1260
tctgcgtctt ctggtggctt gaaggcaaag gcgcaagccc cttcgaaaat taatggaacc     1320
acagttgtta catctaaaga aggcttcaag catgatgatg atctaccttc gcctccccc      1380 agaacttttta tcaaccagtt gcctgattgg agcatgcttc ttgctgctat cacaacaatt    1440
ttcttggccg ctgaaaagca gtggatgatg cttgattgga agccacggcg acctgacatg     1500
cttattgacc cctttgggat aggaaaaaat gttcaggatg gtcttgtgtt ccgtgaaaac     1560
ttttctatta gatcatatga gattggtgct gatcgtaccg catctataga aacagtaatg     1620
aaccatttgc aagtaagtcc gtcctcatac aagtgaatct ttatgatctt cagagatgag     1680
tatgctttga ctaagatagg gctgtttatt tagacactgt aattcaattt catatataga     1740
taatatcatt ctgttgttac ttttcatact atatttatat caactatttg cttaacaaca     1800
ggaaactgca cttaatcatg ttaaaagtgc tgggcttctt ggtgatggct ttggttccac     1860
gccagaaatg tgcaaaaaga acttgatatg ggtggttact cggatgcagg ttgtggtgga     1920
acgctatcct acatggttag tcatctagat tcaaccatta catgtgattt gcaatgtatc     1980
catgttaagc tgctatttct ctgtctattt tagtaatctt tatgaggaat gatcactcct     2040
aaatatattc atggtaatta ttgagactta attatgagaa ccaaaatgct ttggaaattt     2100
gtctgggatg aaaattgatt agatacacaa gctttataca tgatgaacta tgggaaacct     2160
tgtgcaacag agctattgat ctgtacaaga gatgtagtat agcattaatt acatgttatt     2220
agataaggtg acttatcctt gtttaattat tgtaaaaata gaagctgata ctatgtattc     2280
tttgcatttg ttttcttacc agttatatat accctctgtt ctgtttgagt actactagat     2340
gtataaagaa tgcaattatt ctgacttctt ggtgttgggt tgaagttaga taagctatta     2400
gtattattat ggttattcta aatctaatta tctgaaattg tgtgtctata tttgcttcag     2460
gggtgacata gttcaagtgg acacttgggt ttctggatca gggaagaatg gtatgcgtcg     2520
tgattggctt ttacgtgact gcaaaactgg tgaaatcttg acaagagctt ccaggtagaa     2580
atcattctct gtaattttcc ttccccttcc cttctgcttc aagcaaattt taagatgtgt     2640
atcttaatgt gcacgatgct gattggacac aattttaaat cttttcaaaca tttacaaaag    2700 ttatggaacc ctttctttc tctcttgaag atgcaaattt gtcacgactg aagtttgagg      2760
aaatcatttg aattttgcaa tgttaaaaaa gataatgaac tacatatttt gcaggcaaaa     2820
acctctaatt gaacaaactg aacattgtat cttagtttat ttatcagact ttatcatgtg     2880
```

```
tactgatgca tcaccttgga gcttgtaatg aattacatat tagcattttc tgaactgtat    2940
gttatggttt tggtgatcta cagtgtttgg gtcatgatga ataagctgac acggaggctg    3000
tctaaaattc cagaagaagt cagacaggag ataggatctt attttgtgga ttctgatcca    3060
attctagaag aggataacag aaaactgact aaacttgacg acaacacagc ggattatatt    3120
cgtaccggtt taagtgtatg tcaactagtt tttttgtaat tgttgtcatt aatttctttt    3180
cttaaattat ttcagatgtt gctttctaat tagtttacat tatgtatctt cattcttcca    3240
gtctaggtgg agtgatctag atatcaatca gcatgtcaac aatgtgaagt acattgactg    3300
gattctggag gtattttttct gttcttgtat tctaatccac tgcagtcctt gttttgttgt    3360
taaccaaagg actgtccttt gattgtttgc agagtgctcc acagccaatc ttggagagtc    3420
atgagctttc ttccgtgact ttagagtata ggagggagtg tggtagggac agtgtgctgg    3480
attccctgac tgctgtatct ggggccgaca tgggcaatct agctcacagt ggacatgttg    3540
agtgcaagca tttgcttcga ctcgaaaatg gtgctgagat tgtgaggggc aggactgagt    3600
ggaggcccaa acctatgaac aacattggtg ttgtgaacca ggttccagca gaaagcacct    3660
aagattttga atggttaac ggttggagtt gcatcagtct ccttgctatg tttagactta    3720
ttctggcctc tggggagagt tttgcttgtg tctgtccaat caatctacat atctttatat    3780
ccttctaatt tgtgttactt tggtgggtaa gggggaaaag ctgcagtaaa cctcattctc    3840
tctttctgct gctccatatt tcatttcatc tctgattgcg ctactgctag gctgtcttca    3900
atatttaatt gcttgatcaa aatagctagg catgtatatt attattcttt tctcttggct    3960
caattaaaga tgcaattttc attgtgaaca cagcataact attattctta ttattttgt    4020 atagcctgta tgcacgaatg acttgtccat ccaatacaac cgtgattgta tgctccagct    4080
cag                                                                 4083
```

<210> SEQ ID NO 29
<211> LENGTH: 109
<212> TYPE: DNA
<213> ORGANISM: Glycine max
<220> FEATURE:
<223> OTHER INFORMATION: FATB intron I

<400> SEQUENCE: 29

```
gtacgcaaac aaatctgcta ttcattcatt cattcctctt tctctctgat cgcaaactgc      60
acctctacgc tccactcttc tcattttctc ttcctttctc gcttctcag                  109
```

<210> SEQ ID NO 30
<211> LENGTH: 836
<212> TYPE: DNA
<213> ORGANISM: Glycine max
<220> FEATURE:
<223> OTHER INFORMATION: FATB intron II

<400> SEQUENCE: 30

```
gttctcgatt cttttctctt ttaactttat ttttaaaata ataataatga gagctggatg       60
cgtctgttcg ttgtgaattt cgaggcaatg gggttctcat tttcgttaca gttacagatt      120
gcattgtctg ctttcctctt ctcccttgtt tctttgcctt gtctgatttt tcgttttat      180 ttcttacttt taattttgg ggatggatat ttttttctgca tttttcggt ttgcgatgtt       240 ttcaggattc cgattccgag tcagatctgc gccggcttat acgacgaatt tgttcttatt      300
cgcaactttt cgcttgattg gcttgtttta cctctggaat ctcacacgtg atcaaataag      360
```

```
cctgctattt tagttgaagt agaatttgtt ctttatcgga aagaattcta tggatctgtt     420
ctgaaattgg agctactgtt tcgagttgct atttttttta gtagtattaa gaacaagttt     480
gccttttatt ttacattttt ttcctttgct tttgccaaaa gttttatga tcactctctt      540 ctgtttgtga tataactgat gtgctgtgct gttattattt gttatttggg gtgaagtata     600
attttttggg tgaacttgga gcattttag tccgattgat ttctcgatat catttaaggc      660
taaggttgac ctctaccacg cgtttgcgtt tgatgttttt tccattttt ttttatctca      720 tatcttttac agtgtttgcc tatttgcatt tctcttcttt atcccctttc tgtggaaggt     780
gggagggaaa atgtattttt ttttctcttc ctaacttgcg tatattttgc atgcag         836

<210> SEQ ID NO 31
<211> LENGTH: 169
<212> TYPE: DNA
<213> ORGANISM: Glycine max
<220> FEATURE:
<223> OTHER INFORMATION: FATB intron III

<400> SEQUENCE: 31
gtaagtccgt cctcatacaa gtgaatcttt atgatcttca gagatgagta tgctttgact     60
aagatagggc tgtttattta gacactgtaa ttcaatttca tatatagata atatcattct     120
gttgttactt ttcatactat atttatatca actatttgct taacaacag                 169

<210> SEQ ID NO 32
<211> LENGTH: 525
<212> TYPE: DNA
<213> ORGANISM: Glycine max
<220> FEATURE:
<223> OTHER INFORMATION: FATB intron IV

<400> SEQUENCE: 32
gttagtcatc tagattcaac cattacatgt gatttgcaat gtatccatgt taagctgcta     60
tttctctgtc tattttagta atcttatga ggaatgatca ctcctaaata tattcatggt      120
aattattgag acttaattat gagaaccaaa atgctttgga aatttgtctg ggatgaaaat     180
tgattagata cacaagcttt atacatgatg aactatggga aaccttgtgc aacagagcta     240
ttgatctgta caagagatgt agtatagcat taattacatg ttattagata aggtgactta     300
tccttgttta attattgtaa aaatagaagc tgatactatg tattctttgc atttgttttc     360
ttaccagtta tatatacccct ctgttctgtt tgagtactac tagatgtata aagaatgcaa    420
ttattctgac ttccttggtgt tgggttgaag ttagataagc cattagtatt attatggtta    480
ttctaaatct aattatctga aattgtgtgt ctatatttgc ttcag                     525

<210> SEQ ID NO 33
<211> LENGTH: 389
<212> TYPE: DNA
<213> ORGANISM: Glycine max
<220> FEATURE:
<223> OTHER INFORMATION: FATB intron V

<400> SEQUENCE: 33
gtagaaatca ttctctgtaa ttttccttcc cctttccttc tgcttcaagc aaattttaag     60
atgtgtatct taatgtgcac gatgctgatt ggacacaatt ttaaatcttt caaacattta     120
caaaagttat ggaaccctttt cttttctctc ttgaagatgc aaatttgtca cgactgaagt     180
ttgaggaaat cattttgaatt ttgcaatgtt aaaaaagata atgaactaca tattttgcag    240
gcaaaaacct ctaattgaac aaactgaaca ttgtatctta gtttatttat cagactttat     300
```

```
catgtgtact gatgcatcac cttggagctt gtaatgaatt acatattagc attttctgaa      360
ctgtatgtta tggttttggt gatctacag                                        389

<210> SEQ ID NO 34
<211> LENGTH: 106
<212> TYPE: DNA
<213> ORGANISM: Glycine max
<220> FEATURE:
<223> OTHER INFORMATION: FATB intron VI

<400> SEQUENCE: 34
tatgtcaact agttttttg taattgttgt cattaatttc ttttcttaaa ttatttcaga       60
tgttgctttc taattagttt acattatgta tcttcattct tccagt                    106

<210> SEQ ID NO 35
<211> LENGTH: 82
<212> TYPE: DNA
<213> ORGANISM: Glycine max
<220> FEATURE:
<223> OTHER INFORMATION: FATB intron VII

<400> SEQUENCE: 35 gtattttct gttcttgtat tctaatccac tgcagtcctt gttttgttgt taaccaaagg       60
actgtccttt gattgtttgc ag                                               82

<210> SEQ ID NO 36
<211> LENGTH: 208
<212> TYPE: DNA
<213> ORGANISM: Glycine max
<220> FEATURE:
<223> OTHER INFORMATION: FATB 3'UTR

<400> SEQUENCE: 36
gatttgaaat ggttaacgat tggagttgca tcagtctcct tgctatgttt agacttattc      60
tggttccctg gggagagttt tgcttgtgtc tatccaatca atctacatgt ctttaaatat     120
atacaccttc taatttgtga tactttggtg ggtaaggggg aaaagcagca gtaaatctca     180
ttctcattgt aattaaaaaa aaaaaaaa                                        208

<210> SEQ ID NO 37
<211> LENGTH: 229
<212> TYPE: DNA
<213> ORGANISM: Glycine max
<220> FEATURE:
<223> OTHER INFORMATION: FATB 5'UTR

<400> SEQUENCE: 37
acaattacac tgtctctctc ttttccaaaa ttagggaaac aacaaggacg caaaatgaca      60
caatagccct tcttccctgt ttccagcttt tctccttctc tctctctcca tcttcttctt     120
cttcttcact cagtcagatc caactcctca gataacacaa gaccaaaccc gcttttttctg    180 catttctaga ctagacgttc taccggagaa gcgaccttag aaattcatt                 229

<210> SEQ ID NO 38
<211> LENGTH: 1398
<212> TYPE: DNA
<213> ORGANISM: Cuphea pulcherrima
<220> FEATURE:
<223> OTHER INFORMATION: KAS I gene

<400> SEQUENCE: 38
```

-continued

```
atgcattccc tccagtcacc ctcccttcgg gcctccccgc tcgacccctt ccgccccaaa      60
tcatccaccg tccgccccct ccaccgagca tcaattccca acgtccgggc cgcttccccc     120
accgtctccg ctcccaagcg cgagaccgac cccaagaagc gcgtcgtgat caccggaatg     180
ggccttgtct ccgttttcgg ctccgacgtc gatgcgtact acgacaagct cctgtcaggc     240
gagagcggga tcggcccaat cgaccgcttc gacgcctcca agttccccac caggttcggc     300
ggccagattc gtggcttcaa ctccatggga tacattgacg caaaaacgca caggcggctt     360
gatgattgcc ttcgctactg cattgtcgcc gggaagaagt ctcttgagga cgccgatctc     420
ggtgccgacc gcctctccaa gatcgacaag gagagagccg gagtgctggt tgggacagga     480
atgggtggtc tgactgtctt ctctgacggg gttcaatctc ttatcgagaa gggtcaccgg     540
aaaatcaccc ctttcttcat ccccuatgcc attacaaaca tggggtctgc cctgctcgct     600
attgaactcg gtctgatggg cccaaactat tcaatttcca ctgcatgtgc cacttccaac     660
tactgcttcc atgctgctgc taatcatatc cgccgtggtg aggctgatct tatgattgct     720
ggaggcactg aggccgcaat cattccaatt gggttgggag gctttgtggc ttgcagggct     780
ctgtctcaaa ggaacgatga ccctcagact gcctctaggc cctgggataa agaccgtgat     840
ggttttgtga tgggtgaagg tgctggagtg ttggtgctgg agagcttgga acatgcaatg     900
aaacgaggag cacctattat tgcagagtat ttggggaggtg caatcaactg tgatgcttat     960
cacatgactg acccaagggc tgatggtctc ggtgtctcct cttgcattga gagtagcctt    1020
gaagatgctg cgtctcacc tgaagaggtc aattacataa atgctcatgc gacttctact    1080
ctagctgggg atctcgccga gataaatgcc atcaagaagg ttttcaagaa cacaaaggat    1140
atcaaaatta tgcaactaa gtcaatgatc ggacactgtc ttggagcctc tggaggtctt    1200
gaagctatag cgactattaa gggaataaac accggctggc ttcatcccag cattaatcaa    1260
ttcaatcctg agccatccgt ggagttcgac actgttgcca acaagaagca gcaacacgaa    1320
gttaatgttg cgatctcgaa ttcatttgga ttcggaggcc acaactcagt cgtggctttc    1380
tcggctttca agccatga                                                  1398
```

<210> SEQ ID NO 39
<211> LENGTH: 1218
<212> TYPE: DNA
<213> ORGANISM: Cuphea pulcherrima

<400> SEQUENCE: 39

```
atgggtgtgg tgactcctct aggccatgac cctgatgttt tctacaataa tctgcttgat      60
ggaacgagtg gcataagcga gatagagacc tttgattgtg ctcaatttcc tacgagaatt     120
gctggagaga tcaagtcttt ctccacagat ggttgggtgg ccccgaagct ctctaagagg     180
atggacaagt tcatgctata catgctgacc gctggcaaga agcattaac agatggtgga     240
atcaccgaag atgtgatgaa agagctagat aaaagaaaat gcggagttct cattggctca     300
gcaatgggtg gaatgaaggt attcaatgat gccattgaag ccctaaggat ttcatataag     360
aagatgaatc ccttttgtgt acctttcgct accacaaata tgggatcagc tatgcttgca     420
atggacttgg gatggatggg gcccaactac tcgatatcta ctgcttgtgc aacgagtaac     480
ttttgtataa tgaatgctgc gaaccatata atcagaggcg aagcagatgt gatgctttgc     540
gggggctcag atgcggtaat cataccatat ggtatgggag ttttgttgc atgccgagct     600
ttgtcccaga gaaattccga ccctactaaa gcttcaagac catgggacag taatcgtgat     660
ggatttgtta tggggaagg agctggagtg ctactactag aggagttgga gcatgcaaag     720
```

```
aaaagaggtg cgactatttta cgcagaatttt ctaggtggga gtttcacttg cgatgcctac    780
cacatgaccg agcctcaccc tgatggagct ggagtgattc tctgcataga aaggctttg     840 gctcagtcag gagtctctag ggaagacgta aattacataa atgcccatgc cacatccact     900
ccggctggag atatcaaaga gtaccaagct cttatccact gtttcggcca aacagagag      960 ttaaaagtta attcaaccaa atcaatgatt ggtcacctcc tcggagcagc cggtggtgtg    1020
gaagcagttt cagtagttca ggcaataagg actgggtgga tccatccgaa tattaatttg    1080
gaaaacccag atgaaggcgt ggatacaaaa ttgctcgtgg gtcctaagaa ggagagactg    1140
aacgttaagg tcggtttgtc taattcattt gggtttggtg ggcacaactc gtccatactc    1200 ttcgccccctt acatctag                                                1218

<210> SEQ ID NO 40
<211> LENGTH: 1191
<212> TYPE: DNA
<213> ORGANISM: Ricinus communis
<220> FEATURE:
<223> OTHER INFORMATION: delta-9 desaturase

<400> SEQUENCE: 40
atggctctca agctcaatcc tttcctttct caaacccaaa agttaccttc tttcgctctt      60
ccaccaatgg ccagtaccag atctcctaag ttctacatgg cctctaccct caagtctggt    120
tctaaggaag ttgagaatct caagaagcct tcatgcctc ctcgggaggt acatgttcag     180
gttacccatt ctatgccacc ccaaaagatt gagatcttta atccctaga caattgggct     240 gaggagaaca ttctggttca tctgaagcca gttgagaaat gttggcaacc gcaggatttt    300
ttgccagatc ccgcctctga tggatttgat gagcaagtca gggaactcag ggagagagca    360
aaggagattc ctgatgatta ttttgttgtt ttggttggag acatgataac ggaagaagcc    420
cttcccactt atcaaacaat gctgaatacc ttggatggag ttcgggatga acaggtgca     480 agtcctactt cttgggcaat ttggacaagg gcatggactg cggaagagaa tagacatggt    540
gacctcctca ataagtatct ctacctatct ggacagtgg acatgaggca aattgagaag     600
acaattcaat atttgattgg ttcaggaatg gatccacgga cagaaaacag tccatacctt    660
gggttcatct atacatcatt ccaggaaagg gcaaccttca tttctcatgg aacactgcc     720 cgacaagcca aagagcatgg agacataaag ttggctcaaa tatgtggtac aattgctgca    780
gatgagaagc gccatgagac agcctacaca aagatagtgg aaaaactctt tgagattgat    840
cctgatggaa ctgttttggc ttttgctgat atgatgagaa agaaaatttc tatgcctgca    900
cacttgatgt atgatggccg agatgataat cttttttgacc acttttcagc tgttgcgcag    960
cgtcttggag tctacacagc aaaggattat gcagatatat tggagttctt ggtgggcaga   1020
tggaaggtgg ataaactaac gggcctttca gctgagggac aaaaggctca ggactatgtt    1080
tgtcggttac ctccaagaat tagaaggctg gaagagagag ctcaaggaag gcaaaggaa   1140 gcacccacca tgcctttcag ctggattttc gataggcaag tgaagctgta g            1191

<210> SEQ ID NO 41
<211> LENGTH: 1194
<212> TYPE: DNA
<213> ORGANISM: Simmondsia chinensis
<220> FEATURE:
<223> OTHER INFORMATION: delta-9 desaturase

<400> SEQUENCE: 41
```

-continued

```
atggcgttga agcttcacca cacggccttc aatccttcca tggcggttac ctcttcggga      60
cttcctcgat cgtatcacct cagatctcac cgcgttttca tggcttcttc tacaattgga     120
attacttcta aggagatacc caatgccaaa aagcctcaca tgcctcctag agaagctcat     180
gtgcaaaaga cccattcaat gccgcctcaa aagattgaga ttttcaaatc cttggagggt     240
tgggctgagg agaatgtctt ggtgcatctt aaacctgtgg agaagtgttg gcaaccacaa     300
gattttctac ccgacccggc ctccgaggga tttatggatc aagtcaagga gttgagggaa     360
agaaccaaag aaatcccgga tgagtacctt gtggtgttgg ttggcgatat gatcactgaa     420
gaagctcttc cgacctacca gacgatgcta aacacgctcg atggagtacg tgatgagacg     480
ggtgccagcc ttacttcttg ggctatctgg acccgggcat ggaccgctga agagaatagg     540
cacggtgatc ttttgaacaa gtatctttac cttactggtc gagttgacat gaagcagata     600
gagaagacaa tccagtatct aatcggatct ggaatggacc ctcgaagtga aaacaacccc     660
tatctaggct tcatctacac ttccttccaa gagagagcaa ccttcatctc ccatggaaac     720
accgctaggc tcgccaaaga ccacggcgac tttcaactag cacaagtatg tggcatcatc     780
gctgcagatg agaagcgcca cgaaactgcc tacacaaaaa ttgtcgaaaa gctctttgaa     840
atcgacccag acggcgctgt tctagcacta gctgacatga tgagaaagaa ggtttccatg     900
ccagcccact taatgtatga tggcaaagat gacaatctct ttgagaacta ctcagccgtc     960
gctcaacaaa ttggagttta caccgcgaag gactacgctg acatcctcga acacctcgtt    1020
aatcgctgga aagtcgagaa tttaatgggt ctgtctggcg agggacataa ggctcaagat    1080
ttcgtatgtg ggttggcccc gaggatcagg aaactcgggg agagagctca gtcgctaagc    1140
aaaccggtat ctcttgtccc cttcagctgg attttcaaca aggaattgaa ggtt          1194
```

NUCLEIC ACID CONSTRUCTS AND METHODS FOR PRODUCING ALTERED SEED OIL COMPOSITIONS

CROSS-REFERENCE TO RELATED APPLICATIONS

This application claims the benefit under 35 U.S.C. § 119 (e) of U.S. Provisional Application No. 60/365,794 filed Mar. 21, 2002, and No. 60/390,185 filed Jun. 21, 2002, each of which is herein incorporated by reference in its entirety.

INCORPORATION OF SEQUENCE LISTING

A paper copy of the Sequence Listing and a computer readable form of the sequence listing on diskette, containing the file named "OmniSeq for US.txt", which is 45,810 bytes in size (measured in MS-DOS), and which was recorded on Mar. 21, 2003, are herein incorporated by reference.

FIELD OF THE INVENTION

The present invention is directed to recombinant nucleic acid molecules, constructs, and other agents associated with the coordinate manipulation of multiple genes in the fatty acid synthesis pathway. In particular, the agents of the present invention are associated with the simultaneous enhanced expression of certain genes in the fatty acid synthesis pathway and suppressed expression of certain other genes in the same pathway. The present invention is also directed to plants incorporating such agents, and in particular to plants incorporating such constructs where the plants exhibit altered seed oil compositions.

BACKGROUND

Plant oils are used in a variety of applications. Novel vegetable oil compositions and improved approaches to obtain oil compositions, from biosynthetic or natural plant sources, are needed. Depending upon the intended oil use, various different fatty acid compositions are desired. Plants, especially species which synthesize large amounts of oils in seeds, are an important source of oils both for edible and industrial uses. Seed oils are composed almost entirely of triacylglycerols in which fatty acids are esterified to the three hydroxyl groups of glycerol.

Soybean oil typically contains about 16-20% saturated fatty acids: 13-16% palmitate and 3-4% stearate. See generally Gunstone et al., *The Lipid Handbook*, Chapman & Hall, London (1994). Soybean oils have been modified by various breeding methods to create benefits for specific markets. However, a soybean oil that is broadly beneficial to major soybean oil users such as consumers of salad oil, cooking oil and frying oil, and industrial markets such as biodiesel and biolube markets, is not available. Prior soybean oils were either too expensive or lacked an important food quality property such as oxidative stability, good fried food flavor or saturated fat content, or an important biodiesel property such as appropriate nitric oxide emissions or cold tolerance or cold flow.

Higher plants synthesize fatty acids via a common metabolic pathway—the fatty acid synthetase (FAS) pathway, which is located in the plastids. β-ketoacyl-ACP synthases are important rate-limiting enzymes in the FAS of plant cells and exist in several versions. β-ketoacyl-ACP synthase I catalyzes chain elongation to palmitoyl-ACP(C16:0), whereas β-ketoacyl-ACP synthase II catalyzes chain elongation to stearoyl-ACP(C18:0). β-ketoacyl-ACP synthase IV is a variant of β-ketoacyl-ACP synthase II, and can also catalyze chain elongation to 18:0-ACP. In soybean, the major products of FAS are 16:0-ACP and 18:0-ACP. The desaturation of 18:0-ACP to form 18:1-ACP is catalyzed by a plastid-localized soluble delta-9 desaturase (also referred to as "stearoyl-ACP desaturase"). See Voelker et al., 52 *Annu. Rev. Plant Physiol. Plant Mol. Biol.* 335-61 (2001).

The products of the plastidial FAS and delta-9 desaturase, 16:0-ACP, 18:0-ACP, and 18:1-ACP, are hydrolyzed by specific thioesterases (FAT). Plant thioesterases can be classified into two gene families based on sequence homology and substrate preference. The first family, FATA, includes long chain acyl-ACP thioesterases having activity primarily on 18:1-ACP. Enzymes of the second family, FATB, commonly utilize 16:0-ACP (palmitoyl-ACP), 18:0-ACP (stearoyl-ACP), and 18:1-ACP (oleoyl-ACP). Such thioesterases have an important role in determining chain length during de novo fatty acid biosynthesis in plants, and thus these enzymes are useful in the provision of various modifications of fatty acyl compositions, particularly with respect to the relative proportions of various fatty acyl groups that are present in seed storage oils.

The products of the FATA and FATB reactions, the free fatty acids, leave the plastids and are converted to their respective acyl-CoA esters. Acyl-CoAs are substrates for the lipid-biosynthesis pathway (Kennedy Pathway), which is located in the endoplasmic reticulum (ER). This pathway is responsible for membrane lipid formation as well as the biosynthesis of triacylglycerols, which constitute the seed oil. In the ER there are additional membrane-bound desaturases, which can further desaturate 18:1 to polyunsaturated fatty acids. A delta-12 desaturase (FAD2) catalyzes the insertion of a double bond into 18:1, forming linoleic acid (18:2). A delta-15 desaturase (FAD3) catalyzes the insertion of a double bond into 18:2, forming linolenic acid (18:3).

Many complex biochemical pathways have now been manipulated genetically, usually by suppression or over-expression of single genes. Further exploitation of the potential for plant genetic manipulation will require the coordinate manipulation of multiple genes in a pathway. A number of approaches have been used to combine transgenes in one plant—including sexual crossing, retransformation, co-transformation, and the use of linked transgenes. A chimeric transgene with linked partial gene sequences can be used to coordinately suppress numerous plant endogenous genes. Constructs modeled on viral polyproteins can be used to simultaneously introduce multiple coding genes into plant cells. For a review, see Halpin et al., *Plant Mol. Biol.* 47:295-310 (2001).

Thus, a desired plant phenotype may require the expression of one or more genes and the concurrent reduction of expression of another gene or genes. Thus, there exists a need to simultaneously over-express one or more genes and suppress, or down-regulate, the expression of a another gene or genes in plants using a single transgenic construct.

SUMMARY OF THE INVENTION

The present invention provides a nucleic acid molecule or molecules, which when introduced into a cell or organism are capable of suppressing, at least partially reducing, reducing, substantially reducing, or effectively eliminating the expression of at least one or more endogenous FAD2, FAD3, or FATB RNAs while at the same time coexpressing, simultaneously expressing, or coordinately producing one or more RNAs or proteins transcribed from or encoded by beta-ketoacyl-ACP synthase I, beta-ketoacyl-ACP synthase IV, delta-9 desaturase, or CP4 EPSPS, plant cells and plants transformed with the same, and seeds, oil, and other products produced from the transformed plants.

Also provided by the present invention is a recombinant nucleic acid molecule comprising a first set of DNA sequences that is capable, when expressed in a host cell, of suppressing the endogenous expression of at least one, preferably two, genes selected from the group consisting of FAD2, FAD3, and FATB genes; and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, and a delta-9 desaturase gene.

Further provided by the present invention is a recombinant nucleic acid molecule comprising a first set of DNA sequences that is capable, when expressed in a host cell, of forming a dsRNA construct and suppressing the endogenous expression of at least one, preferably two, genes selected from the group consisting of FAD2, FAD3, and FA TB genes, where the first set of DNA sequences comprises a first non-coding sequence that expresses a first RNA sequence that exhibits at least 90% identity to a non-coding region of a FAD2 gene, a first antisense sequence that expresses a first antisense RNA sequence capable of forming a double-stranded RNA molecule with the first RNA sequence, a second non-coding sequence that expresses a second RNA sequence that exhibits at least 90% identity to a non-coding region of a FAD3 gene, and a second antisense sequence that expresses a second antisense RNA sequence capable of forming a double-stranded RNA molecule with the second RNA sequence; and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, and a delta-9 desaturase gene.

The present invention provides methods of transforming plants with these recombinant nucleic acid molecules. The methods include a method of producing a transformed plant having seed with an increased oleic acid content, reduced saturated fatty acid content, and reduced polyunsaturated fatty acid content, comprising (A) transforming a plant cell with a recombinant nucleic acid molecule which comprises a first set of DNA sequences that is capable, when expressed in a host cell, of suppressing the endogenous expression of at least one, preferably two, genes selected from the group consisting of FAD2, FAD3, and FATB genes, and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, and a delta-9 desaturase gene; and (B) growing the transformed plant, where the transformed plant produces seed with an increased oleic acid content, reduced saturated fatty acid content, and reduced polyunsaturated fatty acid content relative to seed from a plant having a similar genetic background but lacking the recombinant nucleic acid molecule.

Further provided are methods of transforming plant cells with the recombinant nucleic acid molecules. The methods include a method of altering the oil composition of a plant cell comprising (A) transforming a plant cell with a recombinant nucleic acid molecule which comprises a first set of DNA sequences that is capable, when expressed in a host cell, of suppressing the endogenous expression of at least one, preferably two, genes selected from the group consisting of FAD2, FAD3, and FATB genes, and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, and a delta-9 desaturase gene; and (B) growing the plant cell under conditions where transcription of the first set of DNA sequences and the second set of DNA sequences is initiated, where the oil composition is altered relative to a plant cell with a similar genetic background but lacking the recombinant nucleic acid molecule.

The present invention also provides a transformed plant comprising a recombinant nucleic acid molecule which comprises a first set of DNA sequences that is capable, when expressed in a host cell, of suppressing the endogenous expression of at least one, preferably two, genes selected from the group consisting of FAD2, FAD3, and FATB genes, and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, and a delta-9 desaturase gene. Further provided by the present invention is a transformed soybean plant bearing seed, where the seed exhibits an oil composition which comprises 55 to 80% by weight oleic acid, 10 to 40% by weight linoleic acid, 6% or less by weight linolenic acid, and 2 to 8% by weight saturated fatty acids, and feedstock, plant parts, and seed derived from the plant.

The present invention provides a soybean seed exhibiting an oil composition comprising 55 to 80% by weight oleic acid, 10 to 40% by weight linoleic acid, 6% or less by weight linolenic acid, and 2 to 8% by weight saturated fatty acids, and also provides a soybean seed exhibiting an oil composition comprising 65 to 80% by weight oleic acid, 10 to 30% by weight linoleic acid, 6% or less by weight linolenic acid, and 2 to 8% by weight of saturated fatty acids. Also provided by the present invention are soyfoods comprising an oil composition which comprises 69 to 73% by weight oleic acid, 21 to 24% by weight linoleic acid, 0.5 to 3% by weight linolenic acid, and 2-3% by weight of saturated fatty acids.

The crude soybean oil provided by the present invention exhibits an oil composition comprising 55 to 80% by weight oleic acid, 10 to 40% by weight linoleic acid, 6% or less by weight linolenic acid, and 2 to 8% by weight saturated fatty acids. Another crude soybean oil provided by the present invention exhibits an oil composition comprising 65 to 80% by weight oleic acid, 10 to 30% by weight linoleic acid, 6% or less by weight linolenic acid, and 2 to 8% by weight of saturated fatty acids.

BRIEF DESCRIPTION OF THE DRAWINGS

FIGS. 7-15 each depict nucleic acid molecules of the present invention.

DETAILED DESCRIPTION OF THE INVENTION

Description of the Nucleic Acid Sequences

Figure 1:
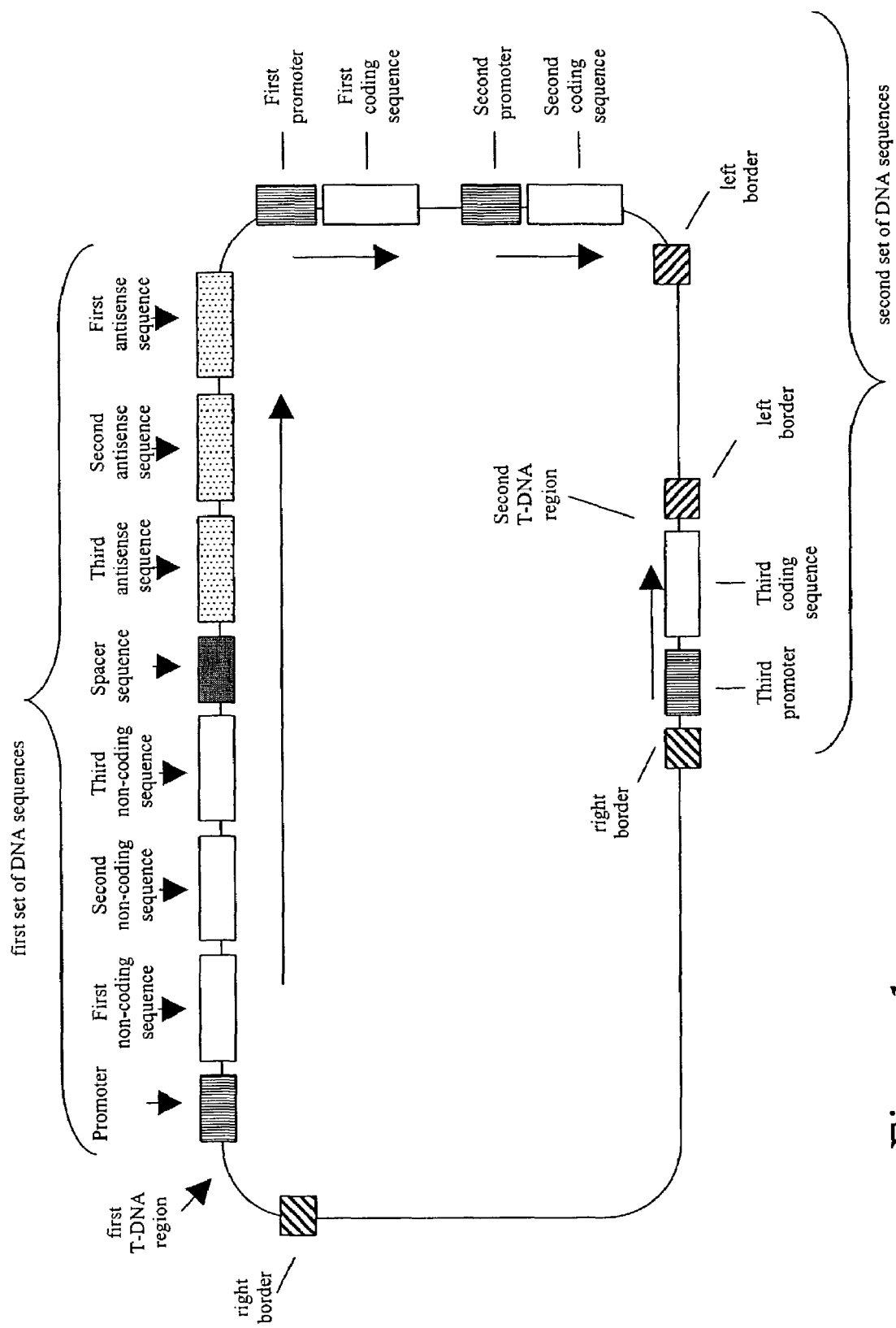
FIGS. 1-4 each depict exemplary nucleic acid molecule configurations.

SEQ ID NO: 1 is a nucleic acid sequence of a FAD2-1A intron 1.

SEQ ID NO: 2 is a nucleic acid sequence of a FAD2-1B intron 1.

SEQ ID NO: 3 is a nucleic acid sequence of a FAD2-1B promoter.

SEQ ID NO: 4 is a nucleic acid sequence of a FAD2-1A genomic clone.

SEQ ID NOs: 5 & 6 are nucleic acid sequences of a FAD2-1A 3' UTR and 5' UTR, respectively.

SEQ ID NOs: 7-13 are nucleic acid sequences of FAD3-1A introns 1, 2, 3A, 4, 5, 3B, and 3C, respectively.

SEQ ID NO: 14 is a nucleic acid sequence of a FAD3-1C intron 4.

SEQ ID NO: 15 is a nucleic acid sequence of a partial FAD3-1A genomic clone.

SEQ ID NOs: 16 & 17 are nucleic acid sequences of a FAD3-1A 3'UTR and 5'UTR, respectively.

SEQ ID NO: 18 is a nucleic acid sequence of a partial FAD3-1B genomic clone.

SEQ ID NOs: 19-25 are nucleic acid sequences of FAD3-1B introns 1, 2, 3A, 3B, 3C, 4, and 5, respectively.

SEQ ID NOs: 26 & 27 are nucleic acid sequences of a FAD3-1B 3'UTR and 5'UTR, respectively.

SEQ ID NO: 28 is a nucleic acid sequence of a FATB genomic clone.

SEQ ID NO: 29-35 are nucleic acid sequences of FATB introns I, II, III, IV, V, VI, and VII, respectively.

SEQ ID NOs: 36 & 37 are nucleic acid sequences of a FATB 3'UTR and 5'UTR, respectively.

SEQ ID NO: 38 is a nucleic acid sequence of a *Cuphea pulcherrima* KAS I gene.

SEQ ID NO: 39 is a nucleic acid sequence of a *Cuphea pulcherrima* KAS IV gene.

SEQ ID NOs: 40 & 41 are nucleic acid sequences of *Ricinus communis* and *Simmondsia chinensis* delta-9 desaturase genes, respectively.

Definitions

"ACP" refers to an acyl carrier protein moiety. "Altered seed oil composition" refers to a seed oil composition from a transgenic or transformed plant of the invention which has altered or modified levels of the fatty acids therein, relative to a seed oil from a plant having a similar genetic background but that has not been transformed. "Antisense suppression" refers to gene-specific silencing that is induced by the introduction of an antisense RNA molecule.

"Coexpression of more than one agent such as an mRNA or protein" refers to the simultaneous expression of an agent in overlapping time frames and in the same cell or tissue as another agent. "Coordinated expression of more than one agent" refers to the coexpression of more than one agent when the production of transcripts and proteins from such agents is carried out utilizing a shared or identical promoter. "Complement" of a nucleic acid sequence refers to the complement of the sequence along its complete length.

"Cosuppression" is the reduction in expression levels, usually at the level of RNA, of a particular endogenous gene or gene family by the expression of a homologous sense construct that is capable of transcribing mRNA of the same strandedness as the transcript of the endogenous gene. Napoli et al., *Plant Cell* 2:279-289 (1990); van der Krol et al., *Plant Cell* 2:291-299 (1990). "Crude soybean oil" refers to soybean oil that has been extracted from soybean seeds, but has not been refined, processed, or blended, although it may be degummed.

When referring to proteins and nucleic acids herein, "derived" refers to either directly (for example, by looking at the sequence of a known protein or nucleic acid and preparing a protein or nucleic acid having a sequence similar, at least in part, to the sequence of the known protein or nucleic acid) or indirectly (for example, by obtaining a protein or nucleic acid from an organism which is related to a known protein or nucleic acid) obtaining a protein or nucleic acid from a known protein or nucleic acid. Other methods of "deriving" a protein or nucleic acid from a known protein or nucleic acid are known to one of skill in the art.

"dsRNA", "dsRNAi" and "RNAi" all refer to gene-specific silencing that is induced by the introduction of a construct capable of forming a double-stranded RNA molecule. A "dsRNA molecule" and an "RNAi molecule" both refer to a double-stranded RNA molecule capable, when introduced into a cell or organism, of at least partially reducing the level of an mRNA species present in a cell or a cell of an organism.

"Exon" refers to the normal sense of the term as meaning a segment of nucleic acid molecules, usually DNA, that encodes part of or all of an expressed protein.

"Fatty acid" refers to free fatty acids and fatty acyl groups.

"Gene" refers to a nucleic acid sequence that encompasses a 5' promoter region associated with the expression of the gene product, any intron and exon regions and 3' or 5' untranslated regions associated with the expression of the gene product. "Gene silencing" refers to the suppression of gene expression or down-regulation of gene expression.

A "gene family" is two or more genes in an organism which encode proteins that exhibit similar functional attributes, and a "gene family member" is any gene of the gene family found within the genetic material of the plant, e.g., a "FAD2 gene family member" is any FAD2 gene found within the genetic material of the plant. An example of two members of a gene family are FAD2-1 and FAD2-2. A gene family can be additionally classified by the similarity of the nucleic acid sequences. Preferably, a gene family member exhibits at least 60%, more preferably at least 70%, more preferably at least 80% nucleic acid sequence identity in the coding sequence portion of the gene.

"Heterologous" means not naturally occurring together. A "high oleic soybean seed" is a seed with oil having greater than 75% oleic acid present in the oil composition of the seed.

A nucleic acid molecule is said to be "introduced" if it is inserted into a cell or organism as a result of human manipulation, no matter how indirect. Examples of introduced nucleic acid molecules include, but are not limited to, nucleic acids that have been introduced into cells via transformation, transfection, injection, and projection, and those that have been introduced into an organism via methods including, but not limited to, conjugation, endocytosis, and phagocytosis.

"Intron" refers to the normal sense of the term as meaning a segment of nucleic acid molecules, usually DNA, that does not encode part of or all of an expressed protein, and which, in endogenous conditions, is transcribed into RNA molecules, but which is spliced out of the endogenous RNA before the RNA is translated into a protein. An "intron dsRNA molecule" and an "intron RNAi molecule" both refer to a double-stranded RNA molecule capable, when introduced into a cell or organism, of at least partially reducing the level of an mRNA species present in a cell or a cell of an organism where the double-stranded RNA molecule exhibits sufficient identity to an intron of a gene present in the cell or organism to reduce the level of an mRNA containing that intron sequence.

A "low saturate" oil composition contains between 3.6 and 8 percent saturated fatty acids.

A "mid-oleic soybean seed" is a seed having between 50% and 85% oleic acid present in the oil composition of the seed.

The term "non-coding" refers to sequences of nucleic acid molecules that do not encode part or all of an expressed protein. Non-coding sequences include but are not limited to introns, promoter regions, 3' untranslated regions (3'UTRs), and 5' untranslated regions (5'UTRs).

A promoter that is "operably linked" to one or more nucleic acid sequences is capable of driving expression of one or more nucleic acid sequences, including multiple coding or non-coding nucleic acid sequences arranged in a polycistronic configuration.

"Physically linked" nucleic acid sequences are nucleic acid sequences that are found on a single nucleic acid molecule. A "plant" includes reference to whole plants, plant organs (e.g., leaves, stems, roots, etc.), seeds, and plant cells and progeny of the same. The term "plant cell" includes, without limitation, seed suspension cultures, embryos, meristematic regions, callus tissue, leaves, roots, shoots, gametophytes, sporophytes, pollen, and microspores. "Plant promoters," include, without limitation, plant viral promoters, promoters derived from plants, and synthetic promoters capable of functioning in a plant cell to promote the expression of an mRNA.

A "polycistronic gene" or "polycistronic mRNA" is any gene or mRNA that contains transcribed nucleic acid sequences which correspond to nucleic acid sequences of more than one gene targeted for expression. It is understood that such polycistronic genes or mRNAs may contain sequences that correspond to introns, 5'UTRs, 3'UTRs, or combinations thereof, and that a recombinant polycistronic gene or mRNA might, for example without limitation, contain sequences that correspond to one or more UTRs from one gene and one or more introns from a second gene.

A "seed-specific promoter" refers to a promoter that is active preferentially or exclusively in a seed. "Preferential activity" refers to promoter activity that is substantially greater in the seed than in other tissues, organs or organelles of the plant. "Seed-specific" includes without limitation activity in the aleurone layer, endosperm, and/or embryo of the seed.

"Sense intron suppression" refers to gene silencing that is induced by the introduction of a sense intron or fragment thereof. Sense intron suppression is described by Fillatti in PCT WO 01/14538 A2. "Simultaneous expression" of more than one agent such as an mRNA or protein refers to the expression of an agent at the same time as another agent. Such expression may only overlap in part and may also occur in different tissue or at different levels.

"Total oil level" refers to the total aggregate amount of fatty acid without regard to the type of fatty acid. "Transgene" refers to a nucleic acid sequence associated with the expression of a gene introduced into an organism. A transgene includes, but is not limited to, a gene endogenous or a gene not naturally occurring in the organism. A "transgenic plant" is any plant that stably incorporates a transgene in a manner that facilitates transmission of that transgene from a plant by any sexual or asexual method.

A "zero saturate" oil composition contains less than 3.6 percent saturated fatty acids.

When referring to proteins and nucleic acids herein, the use of plain capitals, e.g. "FAD2", indicates a reference to an enzyme, protein, polypeptide, or peptide, and the use of italicized capitals, e.g., "FAD2", is used to refer to nucleic acids, including without limitation genes, cDNAs, and mRNAs. A cell or organism can have a family of more than one gene encoding a particular enzyme, and the capital letter that follows the gene terminology (A, B, C) is used to designate the family member, i.e., FAD2-1A is a different gene family member from FAD2-1B.

As used herein, any range set forth is inclusive of the end points of the range unless otherwise stated.

A. Agents

The agents of the invention will preferably be "biologically active" with respect to either a structural attribute, such as the capacity of a nucleic acid molecule to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, greater than 75% free, preferably greater than 90% free, and most preferably greater than 95% free from the other molecules (exclusive of solvent) present in the natural mixture. The term "substantially purified" is not intended to encompass molecules present in their native environmental conditions.

The agents of the invention may also be recombinant. As used herein, the term "recombinant" means any agent (e.g., including but limited to DNA, peptide), that is, or results, however indirectly, from human manipulation of a nucleic acid molecule. It is also understood that the agents of the invention may be labeled with reagents that facilitate detection of the agent, e.g., fluorescent labels, chemical labels, and/or modified bases.

Agents of the invention include nucleic acid molecules that comprise a DNA sequence which is at least 50%, 60%, or 70% identical over their entire length to a plant coding region or non-coding region, or to a nucleic acid sequence that is complementary to a plant coding or non-coding region. More preferable are DNA sequences that are, over their entire length, at least 80% identical; at least 85% identical; at least 90% identical; at least 95% identical; at least 97% identical; at least 98% identical; at least 99% identical; or 100% identical to a plant coding region or non-coding region, or to a nucleic acid sequence that is complementary to a plant coding or non-coding region.

"Identity," as is well understood in the art, is a relationship between two or more polypeptide sequences or two or more nucleic acid molecule sequences, as determined by comparing the sequences. In the art, "identity" also means the degree of sequence relatedness between polypeptide or nucleic acid molecule sequences, as determined by the match between strings of such sequences. "Identity" can be readily calculated by known methods including, but not limited to, those described in *Computational Molecular Biology*, Lesk, ed., Oxford University Press, New York 1988; *Biocomputing: Informatics and Genome Projects*, Smith, ed., Academic Press, New York 1993; *Computer Analysis of Sequence Data, Part I*, Griffin and Griffin, eds., Humana Press, New Jersey 1994; *Sequence Analysis in Molecular Biology*, von Heinje, Academic Press 1987; *Sequence Analysis Primer*, Gribskov and Devereux, eds., Stockton Press, New York 1991; and Carillo and Lipman, SIAM *J. Applied Math*, 48:1073 1988.

Methods to determine identity are designed to give the largest match between the sequences tested. Moreover, methods to determine identity are codified in publicly available programs. Computer programs which can be used to determine identity between two sequences include, but are not limited to, GCG; a suite of five BLAST programs, three designed for nucleotide sequences queries (BLASTN, BLASTX, and TBLASTX) and two designed for protein sequence queries (BLASTP and TBLASTN). The BLASTX program is publicly available from NCBI and other sources, e.g., *BLAST Manual*, Altschul et al., NCBI NLM NIH, Bethesda, Md. 20894; Altschul et al., *J. Mol. Biol.* 215:403410 (1990). The well-known Smith Waterman algorithm can also be used to determine identity.

Parameters for polypeptide sequence comparison typically include the following: Algorithm: Needleman and Wunsch, *J. Mol. Biol.* 48:443-453 (1970); Comparison matrix: BLOSUM62 from Hentikoff and Hentikoff, *Proc. Natl. Acad. Sci. USA* 89:10915-10919 (1992); Gap Penalty: 12; Gap Length Penalty: 4. A program that can be used with these parameters is publicly available as the "gap" program from Genetics Computer Group ("GCG"), Madison, Wis. The above parameters along with no penalty for end gap are the default parameters for peptide comparisons.

Parameters for nucleic acid molecule sequence comparison include the following: Algorithm: Needleman and Wunsch, *J. Mol. Bio.* 48:443-453 (1970); Comparison matrix: matches—+10; mismatches=0; Gap Penalty: 50; Gap Length Penalty: 3. As used herein, "% identity" is determined using the above parameters as the default parameters for nucleic acid molecule sequence comparisons and the "gap" program from GCG, version 10.2.

Subsets of the nucleic acid sequences of the present invention include fragment nucleic acid molecules. "Fragment nucleic acid molecule" refers to a piece of a larger nucleic acid molecule, which may consist of significant portion(s) of, or indeed most of, the larger nucleic acid molecule, or which may comprise a smaller oligonucleotide having from about 15 to about 400 contiguous nucleotides and more preferably, about 15 to about 45 contiguous nucleotides, about 20 to about 45 contiguous nucleotides, about 15 to about 30 contiguous nucleotides, about 21 to about 30 contiguous nucleotides, about 21 to about 25 contiguous nucleotides, about 21 to about 24 contiguous nucleotides, about 19 to about 25 contiguous nucleotides, or about 21 contiguous nucleotides. Fragment nucleic acid molecules may consist of significant portion(s) of, or indeed most of, a plant coding or non-coding region, or alternatively may comprise smaller oligonucleotides. In a preferred embodiment, a fragment shows 100% identity to the plant coding or non-coding region. In another preferred embodiment, a fragment comprises a portion of a larger nucleic acid sequence. In another aspect, a fragment nucleic acid molecule has a nucleic acid sequence that has at least 15, 25, 50, or 100 contiguous nucleotides of a nucleic acid molecule of the present invention. In a preferred embodiment, a nucleic acid molecule has a nucleic acid sequence that has at least 15, 25, 50, or 100 contiguous nucleotides of a plant coding or non-coding region.

In another aspect of the present invention, the DNA sequence of the nucleic acid molecules of the present invention can comprise sequences that differ from those encoding a polypeptide or fragment of the protein due to conservative amino acid changes in the polypeptide; the nucleic acid sequences coding for the polypeptide can therefore have sequence differences corresponding to the conservative changes. In a further aspect of the present invention, one or more of the nucleic acid molecules of the present invention differ in nucleic acid sequence from those for which a specific sequence is provided herein because one or more codons have been replaced with a codon that encodes a conservative substitution of the amino acid originally encoded.

Agents of the invention also include nucleic acid molecules that encode at least about a contiguous 10 amino acid region of a polypeptide of the present invention, more preferably at least about a contiguous 25, 40, 50, 100, or 125 amino acid region of a polypeptide of the present invention. Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above-described nucleic acid and amino acid sequences may be modified to reflect the preferred codon usage of a host cell or organism in which they are contained. Therefore, a contiguous 10 amino acid region of a polypeptide of the present invention could be encoded by numerous different nucleic acid sequences. Modification of a structural nucleic acid sequence for optimal codon usage in plants is described in U.S. Pat. No. 5,689,052.

Agents of the invention include nucleic acid molecules. For example, without limitation, in an aspect of the present invention, the nucleic acid molecule of the present invention comprises an intron sequence of SEQ ID NO: 19, 20, 21, 22, 23, 25, 32, 33, 34, or 35 or fragments thereof or complements thereof. In another aspect of the invention, the nucleic acid molecule comprises a nucleic acid sequence, which when introduced into a cell or organism, is capable of suppressing the production of an RNA or protein while simultaneously expressing, coexpressing or coordinately expressing another RNA or protein. In an aspect of the invention, the nucleic acid molecule comprises a nucleic acid sequence, which when introduced into a cell or organism is capable of suppressing, at least partially reducing, reducing, substantially reducing, or effectively eliminating the expression of endogenous FAD2, FAD3, and/or FATB RNA while at the same time coexpressing, simultaneously expressing, or coordinately expressing a beta-ketoacyl-ACP synthase I, beta-ketoacyl-ACP synthase IV, delta-9 desaturase, and/or CP4 EPSPS RNA or protein.

By decreasing the amount of FAD2 and/or FAD3 available in a plant cell, a decreased percentage of polyunsaturated fatty acids such as linoleate (C18:2) and linolenate (C18:3) may be provided. Modifications in the pool of fatty acids available for incorporation into triacylglycerols may likewise affect the composition of oils in the plant cell. Thus, a decrease in expression of FAD2 and/or FAD3 may result in an increased proportion of mono-unsaturated fatty acids such as oleate (C18:1). When the amount of FATB is decreased in a plant cell, a decreased amount of saturated fatty acids such as palmitate and stearate may be provided. Thus, a decrease in expression of FATB may result in an increased proportion of unsaturated fatty acids such as oleate (18:1). The simultaneous suppression of FAD2, FAD3, and FATB expression thereby results in driving the FAS pathway toward an overall increase in mono-unsaturated fatty acids of 18-carbon length, such as oleate (C18:1). See U.S. Pat. No. 5,955,650.

By increasing the amount of beta-ketoacyl-ACP synthase I (KAS I) and/or beta-ketoacyl-ACP synthase IV (KAS IV) available in a plant cell, a decreased percentage of 16:0-ACP may be provided, leading to an increased percentage of 18:0-ACP. A greater amount of 18:0-ACP in combination with the simultaneous suppression of one or more of FAD2, FAD3, and FATB, thereby helps drive the oil composition toward an overall increase in oleate (C18:1). By increasing the amount of delta-9 desaturase available in a plant cell, an increased percentage of unsaturated fatty acids may be provided, resulting in an overall lowering of stearate and total saturates.

These combinations of increased and decreased enzyme expression may be manipulated to produce fatty acid compositions, including oils, having an increased oleate level, decreased linoleate, linolenate, stearate, and/or palmitate levels, and a decreased overall level of saturates. Enhancement of gene expression in plants may occur through the introduction of extra copies of coding sequences of the genes into the plant cell or, preferably, the incorporation of extra copies of coding sequences of the gene into the plant genome. Overexpression may also occur though increasing the activities of the regulatory mechanisms that regulate the expression of genes, i.e., up-regulation of the gene expression.

Production of CP4 EPSPS in a plant cell provides the plant cell with resistance or tolerance to glyphosate, thereby providing a convenient method for identification of successful transformants via glyphosate-tolerant selection.

Suppression of gene expression in plants, also known as gene silencing, occurs at both the transcriptional level and post-transcriptional level. There are various methods for the suppression of expression of endogenous sequences in a host cell, including, but not limited to, antisense suppression, cosuppression, ribozymes, combinations of sense and antisense (double-stranded RNAi), promoter silencing, and DNA binding proteins such as zinc finger proteins. (See, e.g., WO 98/53083 and WO 01/14538). Certain of these mechanisms are associated with nucleic acid homology at the DNA or RNA level. In plants, double-stranded RNA molecules can induce sequence-specific silencing. Gene silencing is often referred to as double stranded RNA ("dsRNAi") in plants, as RNA interference or RNAi in *Caenorhabditis elegans* and in animals, and as quelling in fungi.

In a preferred embodiment, the nucleic acid molecule of the present invention comprises (a) a first set of DNA sequences, each of which exhibits sufficient homology to one or more coding or non-coding sequences of a plant gene such that when it is expressed, it is capable of effectively eliminating, substantially reducing, or at least partially reducing the level of an mRNA transcript or protein encoded by the gene from which the coding or non-coding sequence was derived, or any gene which has homology to the target non-coding sequence, and (b) a second set of DNA sequences, each of which exhibits sufficient homology to a plant gene so that when it is expressed, it is capable of at least partially enhancing, increasing, enhancing, or substantially enhancing the level of an mRNA transcript or protein encoded by the gene.

As used herein, "a reduction" of the level or amount of an agent such as a protein or mRNA means that the level or amount is reduced relative to a cell or organism lacking a DNA sequence capable of reducing the agent. For example, "at least a partial reduction" refers to a reduction of at least 25%, "a substantial reduction" refers to a reduction of at least 75%, and "an effective elimination" refers to a reduction of greater than 95%, all of which reductions in the level or amount of the agent are relative to a cell or organism lacking a DNA sequence capable of reducing the agent.

As used herein, "an enhanced" or "increased" level or amount of an agent such as a protein or mRNA means that the level or amount is higher than the level or amount of agent present in a cell, tissue or plant with a similar genetic background but lacking an introduced nucleic acid molecule encoding the protein or mRNA. For example, an "at least partially enhanced" level refers to an increase of at least 25%, and a "substantially enhanced" level refers to an increase of at least 100%, all of which increases in the level or amount of an agent are relative to the level or amount of agent that is present in a cell, tissue or plant with a similar genetic background but lacking an introduced nucleic acid molecule encoding the protein or mRNA.

When levels of an agent are compared, such a comparison is preferably carried out between organisms with a similar genetic background. Preferably, a similar genetic background is a background where the organisms being compared share 50% or greater, more preferably 75% or greater, and, even more preferably 90% or greater sequence identity of nuclear genetic material. In another preferred aspect, a similar genetic background is a background where the organisms being compared are plants, and the plants are isogenic except for any genetic material originally introduced using plant transformation techniques. Measurement of the level or amount of an agent may be carried out by any suitable method, non-limiting examples of which include comparison of mRNA transcript levels, protein or peptide levels, and/or phenotype, especially oil content. As used herein, mRNA transcripts include processed and non-processed mRNA transcripts, and proteins or peptides include proteins or peptides with or without any post-translational modification.

The DNA sequences of the first set of DNA sequences may be coding sequences, intron sequences, 3'UTR sequences, 5'UTR sequences, promoter sequences, other non-coding sequences, or any combination of the foregoing. The first set of DNA sequences encodes one or more sequences which, when expressed, are capable of selectively reducing either or both the protein and the transcript encoded by a gene selected from the group consisting of FAD2, FAD3, and FATB. In a preferred embodiment, the first set of DNA sequences is capable of expressing antisense RNA, in which the individual antisense sequences may be linked in one transcript, or may be in unlinked individual transcripts. In a further preferred embodiment, the first set of DNA sequences are physically linked sequences which are capable of expressing a single dsRNA molecule. In a different preferred embodiment, the first set of DNA sequences is capable of expressing sense cosuppresion RNA, in which the individual sense sequences may be linked in one transcript, or may be in unlinked individual transcripts. Exemplary embodiments of the first set of DNA sequences are described in Part B of the Detailed Description, and in the Examples.

The second set of DNA sequences encodes one or more sequences which, when expressed, are capable of increasing one or both of the protein and transcript encoded by a gene selected from the group consisting of beta-ketoacyl-ACP synthase I (KAS I), beta-ketoacyl-ACP synthase IV (KAS IV), delta-9 desaturase, and CP4 EPSPS. The DNA sequences of the second set of DNA sequences may be physically linked sequences. Exemplary embodiments of the second set of DNA sequences are described below in Parts C and D of the Detailed Description.

Thus, the present invention provides methods for altering the composition of fatty acids and compounds containing such fatty acids, such as oils, waxes, and fats. The present invention also provides methods for the production of particular fatty acids in host cell plants. Such methods employ the use of the expression cassettes described herein for the modification of the host plant cell's FAS pathway.

B. First Set of DNA Sequences

In an aspect of the present invention, a nucleic acid molecule comprises a first set of DNA sequences, which when introduced into a cell or organism, expresses one or more sequences capable of effectively eliminating, substantially reducing, or at least partially reducing the levels of mRNA transcripts or proteins encoded by one or more genes. Preferred aspects include as a target an endogenous gene, a plant gene, and a non-viral gene. In an aspect of the present invention, a gene is a FAD2, FAD3, or FATB gene.

In an aspect, a nucleic acid molecule of the present invention comprises a DNA sequence which exhibits sufficient homology to one or more coding or non-coding sequences from a plant gene, which when introduced into a plant cell or plant and expressed, is capable of effectively eliminating, substantially reducing, or at least partially reducing the level of an mRNA transcript or protein encoded by the gene from which the coding or non-coding sequence(s) was derived. The DNA sequences of the first set of DNA sequences encode RNA sequences or RNA fragments which exhibit at least 90%, preferably at least 95%, more preferably at least 98%, most preferably at least 100% identity to a coding or non-coding region derived from the gene which is to be suppressed. Such percent identity may be to a nucleic acid fragment.

Preferably, the non-coding sequence is a 3' UTR, 5'UTR, or a plant intron from a plant gene. More preferably, the non-coding sequence is a promoter sequence, 3' UTR, 5'UTR, or a plant intron from a plant gene. The intron may be located between exons, or located within a 5' or 3' UTR of a plant gene.

The sequence(s) of the first set of DNA sequences may be designed to express a dsRNA construct, a sense suppression RNA construct, or an antisense RNA construct or any other suppression construct in order to achieve the desired effect when introduced into a plant cell or plant. Such DNA sequence(s) may be fragment nucleic acid molecules. In a preferred aspect, a dsRNA construct contains exon sequences, but the exon sequences do not correspond to a sufficient part of a plant exon to be capable of effectively eliminating, substantially reducing, or at least partially reducing the level of an mRNA transcript or protein encoded by the gene from which the exon was derived.

A plant intron can be any plant intron from a gene, whether endogenous or introduced. Nucleic acid sequences of such introns can be derived from a multitude of sources, including, without limitation, databases such as EMBL and Genbank which may be found on the Internet at ebi.ac.uk/swisprot/; expasy.ch/; embl-heidelberg.de/; and ncbi.nlm.nih.gov. Nucleic acid sequences of such introns can also be derived, without limitation, from sources such as the GENSCAN program which may be found on the Internet at genes.mit.edu/GENSCAN.html.

Additional introns may also be obtained by methods which include, without limitation, screening a genomic library with a probe of either known exon or intron sequences, comparing genomic sequence with its corresponding cDNA sequence, or cloning an intron such as a soybean intron by alignment to an intron from another organism, such as, for example, Arabidopsis. In addition, other nucleic acid sequences of introns will be apparent to one of ordinary skill in the art. The above-described methods may also be used to derive and obtain other non-coding sequences, including but not limited to, promoter sequences, 3'UTR sequences, and 5'UTR sequences.

A "FAD2", "Δ12 desaturase" or "omega-6 desaturase" gene encodes an enzyme (FAD2) capable of catalyzing the insertion of a double bond into a fatty acyl moiety at the twelfth position counted from the carboxyl terminus. The term "FAD2-1" is used to refer to a FAD2 gene that is naturally expressed in a specific manner in seed tissue, and the term "FAD2-2" is used to refer a FAD2 gene that is (a) a different gene from a FAD2-1 gene and (b) is naturally expressed in multiple tissues, including the seed. Representative FAD2 sequences include, without limitation, those set forth in U.S. patent application Ser. No. 10/176,149 filed on Jun. 21, 2002, and in SEQ ID NOs: 1-6.

A "FAD3", "Δ15 desaturase" or "omega-3 desaturase" gene encodes an enzyme (FAD3) capable of catalyzing the insertion of a double bond into a fatty acyl moiety at the fifteenth position counted from the carboxyl terminus. The term "FAD3-1" is used to refer a FAD3 gene family member that is naturally expressed in multiple tissues, including the seed. Representative FAD3 sequences include, without limitation, those set forth in U.S. patent application Ser. No. 10/176,149 filed on Jun. 21, 2002, and in SEQ ID NOs: 7-27.

A "FATB" or "palmitoyl-ACP thioesterase" gene encodes an enzyme (FATB) capable of catalyzing the hydrolytic cleavage of the carbon-sulfur thioester bond in the panthothene prosthetic group of palmitoyl-ACP as its preferred reaction. Hydrolysis of other fatty acid-ACP thioesters may also be catalyzed by this enzyme. Representative FATB sequences include, without limitation, those set forth in U.S. Provisional Application No. 60/390,185 filed on Jun. 21, 2002; U.S. Pat. Nos. 5,955,329; 5,723,761; 5,955,650; and 6,331,664; and SEQ ID NOs: 28-37.

C. Second Set of DNA Sequences

In an aspect of the present invention, a nucleic acid molecule comprises a second set of DNA sequences, which when introduced into a cell or organism, is capable of partially enhancing, increasing, enhancing, or substantially enhancing the levels of mRNA transcripts or proteins encoded by one or more genes. In an aspect of the present invention, a gene is an endogenous gene. In an aspect of the present invention, a gene is a plant gene. In another aspect of the present invention, a gene is a truncated gene where the truncated gene is capable of catalyzing the reaction catalyzed by the full gene. In an aspect of the present invention, a gene is a beta-ketoacyl-ACP synthase I, beta-ketoacyl-ACP synthase IV, delta-9 desaturase, or CP4 EPSPS gene.

A gene of the present invention can be any gene, whether endogenous or introduced. Nucleic acid sequences of such genes can be derived from a multitude of sources, including, without limitation, databases such as EMBL and Genbank which may be found on the Internet at ebi.ac.uk/swisprot/; expasy.ch/; embl-heidelberg.de/; and ncbi.nlm.nih.gov. Nucleic acid sequences of such genes can also be derived, without limitation, from sources such as the GENSCAN program which may be found on the Internet at genes.mit.edu/GENSCAN.html.

Additional genes may also be obtained by methods which include, without limitation, screening a genomic library or a cDNA library with a probe of either known gene sequences, cloning a gene by alignment to a gene or probe from another organism, such as, for example, Arabidopsis. In addition, other nucleic acid sequences of genes will be apparent to one of ordinary skill in the art. Additional genes may, for example without limitation, be amplified by polymerase chain reaction (PCR) and used in an embodiment of the present invention. In addition, other nucleic acid sequences of genes will be apparent to one of ordinary skill in the art.

Automated nucleic acid synthesizers may be employed for this purpose, and to make a nucleic acid molecule that has a sequence also found in a cell or organism. In lieu of such synthesis, nucleic acid molecules may be used to define a pair of primers that can be used with the PCR to amplify and obtain any desired nucleic acid molecule or fragment of a first gene.

A "KAS I" or "beta-ketoacyl-ACP synthase I" gene encodes an enzyme (KAS I) capable of catalyzing the elongation of a fatty acyl moiety up to palmitoyl-ACP(C 16:0). Representative KAS I sequences include, without limitation, those set forth in U.S. Pat. No. 5,475,099 and PCT Publication WO 94/10189, and in SEQ ID NO: 38.

A "KAS IV" or "beta-ketoacyl-ACP synthase IV" gene encodes an enzyme (KAS IV) capable of catalyzing the condensation of medium chain acyl-ACPs and enhancing the production of 18:0-ACP. Representative KAS IV sequences include, without limitation, those set forth in PCT Publication WO 98/46776, and in SEQ ID NO: 39.

A "delta-9 desaturase" or "stearoyl-ACP desaturase" or "omega-9 desaturase" gene encodes an enzyme capable of catalyzing the insertion of a double bond into a fatty acyl moiety at the ninth position counted from the carboxyl terminus. A preferred delta-9 desaturase of the present invention is a plant or cyanobacterial delta-9 desaturase, and more preferably a delta-9 desaturase that is also found in an organism selected from the group consisting of *Cartharmus tinctorius, Ricinus communis, Simmonsia chinensis*, and *Brassica campestris*. Representative delta-9 desaturase sequences include, without limitation, those set forth in U.S. Pat. No. 5,723,595, and SEQ ID NOs: 4041.

A "CP4 EPSPS" or "CP45-enolpyruvylshikimate-3-phosphate synthase" gene encodes an enzyme (CP4 EPSPS) capable of conferring a substantial degree of glyphosate resistance upon the plant cell and plants generated therefrom. The CP4 EPSPS sequence may be a CP4 EPSPS sequence derived from *Agrobacterium tumefaciens* sp. CP4 or a variant or synthetic form thereof, as described in U.S. Pat. No. 5,633,435. Representative CP4 EPSPS sequences include, without limitation, those set forth in U.S. Pat. Nos. 5,627,061 and 5,633,435.

D. Recombinant Vectors and Constructs

One or more of the nucleic acid constructs of the invention may be used in plant transformation or transfection. The levels of products such as transcripts or proteins may be increased or decreased throughout an organism such as a plant or localized in one or more specific organs or tissues of the organism. For example the levels of products may be increased or decreased in one or more of the tissues and organs of a plant including without limitation: roots, tubers, stems, leaves, stalks, fruit, berries, nuts, bark, pods, seeds and flowers. A preferred organ is a seed. For example, exogenous genetic material may be transferred into a plant cell and the plant cell regenerated into a whole, fertile or sterile plant or plant part.

"Exogenous genetic material" is any genetic material, whether naturally occurring or otherwise, from any source that is capable of being inserted into any organism. Such exogenous genetic material includes, without limitation, nucleic acid molecules and constructs of the present invention. Exogenous genetic material may be transferred into a host cell by the use of a DNA vector or construct designed for such a purpose. Design of such a vector is generally within the skill of the art (See, e.g., *Plant Molecular Biology: A Laboratory Manual*, Clark (ed.), Springer, New York (1997)).

A construct or vector may include a promoter functional in a plant cell, or a plant promoter, to express a nucleic acid molecule of choice. A number of promoters that are active in plant cells have been described in the literature, and the CaMV 35S and FMV promoters are preferred for use in plants. Preferred promoters are enhanced or duplicated versions of the CaMV 35S and FMV 35S promoters. Odell et al., *Nature* 313: 810-812 (1985); U.S. Pat. No. 5,378,619. Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used.

Particularly preferred promoters can also be used to express a nucleic acid molecule of the present invention in seeds or fruits. Indeed, in a preferred embodiment, the promoter used is a seed specific promoter. Examples of such promoters include the 5' regulatory regions from such genes as napin (Kridl et al., *Seed Sci. Res.* 1:209-219 (1991)), phaseolin, stearoyl-ACP desaturase, 7Sα, 7sα' (Chen et al., *Proc. Natl. Acad. Sci.*, 83:8560-8564 (1986)), USP, arcelin and oleosin. Preferred promoters for expression in the seed are 7Sα, 7sα', napin, and FAD2-1A promoters.

Constructs or vectors may also include other genetic elements, including but not limited to, 3' transcriptional terminators, 3' polyadenylation signals, other untranslated nucleic acid sequences, transit or targeting sequences, selectable or screenable markers, promoters, enhancers, and operators. Constructs or vectors may also contain a promoterless gene that may utilize an endogenous promoter upon insertion.

Nucleic acid molecules that may be used in plant transformation or transfection may be any of the nucleic acid molecules of the present invention. It is not intended that the present invention be limited to the illustrated embodiments. Exemplary nucleic acid molecules have been described in Part A of the Detailed Description, and further non-limiting exemplary nucleic acid molecules are described below and illustrated in FIGS. 1-4, and in the Examples.

Referring now to the drawings, embodiments of the nucleic acid molecule of the present invention are shown in FIGS. 1-4. As described above, the nucleic acid molecule comprises (a) a first set of DNA sequences and (b) a second set of DNA sequences, which are located on one or more T-DNA regions, each of which is flanked by a right border and a left border. Within the T-DNA regions the direction of transcription is shown by arrows. The nucleic acid molecules described may have their DNA sequences arranged in monocistronic or polycistronic configurations. Preferred configurations include a configuration in which the first set of DNA sequences and the second set of DNA sequences are located on a single T-DNA region.

In each of the illustrated embodiments, the first set of DNA sequences comprises one or more sequences which when expressed are capable of selectively reducing one or both of the protein and transcript encoded by a gene selected from the group consisting of FAD2, FAD3, and FA TB. Preferably each sequence in the first set of DNA sequences is capable, when expressed, of suppressing the expression of a different gene, including without limitation different gene family members. The sequences may include coding sequences, intron sequences, 3'UTR sequences, 5'UTR sequences, other non-coding sequences, or any combination of the foregoing. The first set of DNA sequences may be expressed in any suitable form, including as a dsRNA construct, a sense cosuppression construct, or as an antisense construct. The first set of DNA sequences is operably linked to at least one promoter which drives expression of the sequences, which can be any promoter functional in a plant, or any plant promoter. Preferred promoters include, but are not limited to, a napin promoter, a 7Sα promoter, a 7sα' promoter, an arcelin promoter, or a FAD2-1A promoter.

The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which can be any promoter functional in a plant, or any plant promoter. Preferred promoters for use in the second set of DNA sequences are an FMV promoter and/or seed-specific promoters. Particularly preferred seed-specific promoters include, but are not limited to, a napin promoter, a 7Sα promoter, a 7sα' promoter, an arcelin promoter, a delta-9 desaturase promoter, or a FAD2-1A promoter.

Figure 2:
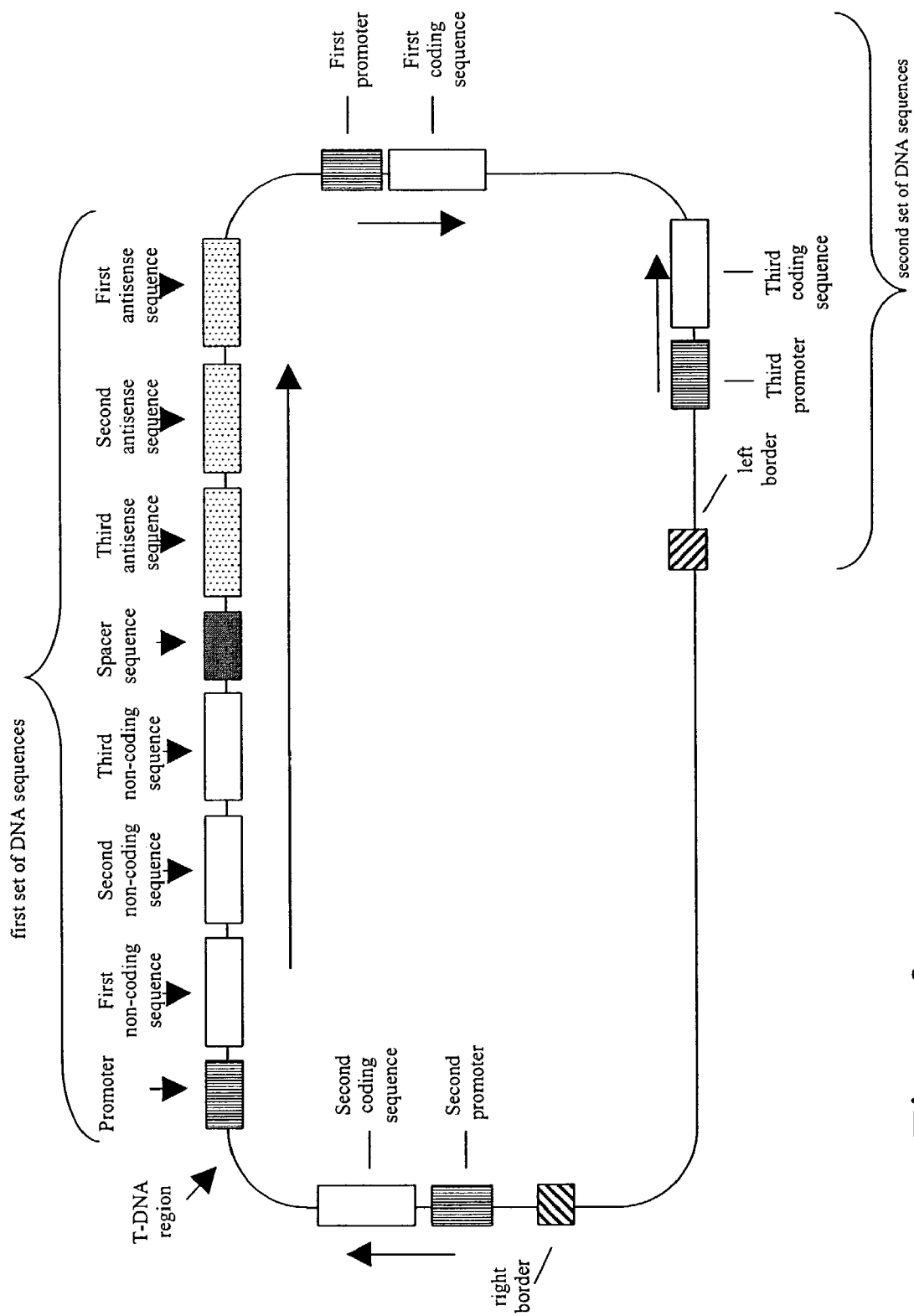

In the embodiments depicted in FIGS. 1 and 2, the first set of DNA sequences, when expressed, is capable of forming a dsRNA molecule that is capable of suppressing the expression of one or both of the protein and transcript encoded by, or transcribed from, a gene selected from the group consisting of FAD2, FAD3, and FATB. The first set of DNA sequences depicted in FIG. 1 comprises three non-coding sequences, each of which expresses an RNA sequence (not shown) that exhibits identity to a non-coding region of a gene selected from the group consisting of FAD2, FAD3, and FATB genes. The non-coding sequences each express an RNA sequence that exhibits at least 90% identity to a non-coding region of a gene selected from the group consisting of FAD2, FAD3, and FA TB genes. The first set of DNA sequences also comprises three antisense sequences, each of which expresses an antisense RNA sequence (not shown) that is capable of forming a double-stranded RNA molecule with its respective corresponding RNA sequence (as expressed by the non-coding sequences).

The non-coding sequences may be separated from the antisense sequences by a spacer sequence, preferably one that promotes the formation of a dsRNA molecule. Examples of such spacer sequences include those set forth in Wesley et al., supra, and Hamilton et al., Plant J., 15:737-746 (1988). In a preferred aspect, the spacer sequence is capable of forming a hairpin structure as illustrated in Wesley et al., supra. Particularly preferred spacer sequences in this context are plant introns or parts thereof. A particularly preferred plant intron is a spliceable intron. Spliceable introns include, but are not limited to, an intron selected from the group consisting of PDK intron, FAD3-1A or FAD3-1B intron #5, FAD3 intron #1, FAD3 intron #3A, FAD3 intron #3B, FAD3 intron #3C, FAD3 intron #4, FAD3 intron #5, FAD2 intron #1, and FAD2-2 intron. Preferred spliceable introns include, but are not limited to, an intron selected from the group consisting of FAD3 intron #1, FAD3 intron #3A, FAD3 intron #3B, FAD3 intron #3C, and FAD3 intron #5. Other preferred spliceable introns include, but are not limited to, a spliceable intron that is about 0.75 kb to about 1.1 kb in length and is capable of facilitating an RNA hairpin structure. One non-limiting example of a particularly preferred spliceable intron is FAD3 intron #5.

Referring now to FIG. 1, the nucleic acid molecule comprises two T-DNA regions, each of which is flanked by a right border and a left border. The first T-DNA region comprises the first set of DNA sequences that is operably linked to a promoter, and the first T-DNA region further comprises a first part of the second set of DNA sequences that comprises a first promoter operably linked to a first coding sequence, and a second promoter operably linked to a second coding sequence. The second T-DNA region comprises a second part of the second set of DNA sequences that comprises a third promoter operably linked to a third coding sequence. In a preferred embodiment depicted in FIG. 2, the nucleic acid molecule comprises a single T-DNA region, which is flanked by a right border and a left border. The first and second sets of DNA sequences are all located on the single T-DNA region.

In the dsRNA-expressing embodiments shown in FIGS. 1 and 2, the order of the sequences may be altered from that illustrated and described, however the non-coding sequences and the antisense sequences preferably are arranged around the spacer sequence such that, when expressed, the first non-coding sequence can hybridize to the first antisense sequence, the second non-coding sequence can hybridize to the second antisense sequence, and the third non-coding sequence can hybridize to the third antisense sequence such that a single dsRNA molecule can be formed. Preferably the non-coding sequences are in a sense orientation, and the antisense sequences are in an antisense orientation relative to the promoter. The numbers of non-coding, antisense, and coding sequences, and the various relative positions thereof on the T-DNA region(s) may also be altered in any manner suitable for achieving the goals of the present invention.

Figure 3:
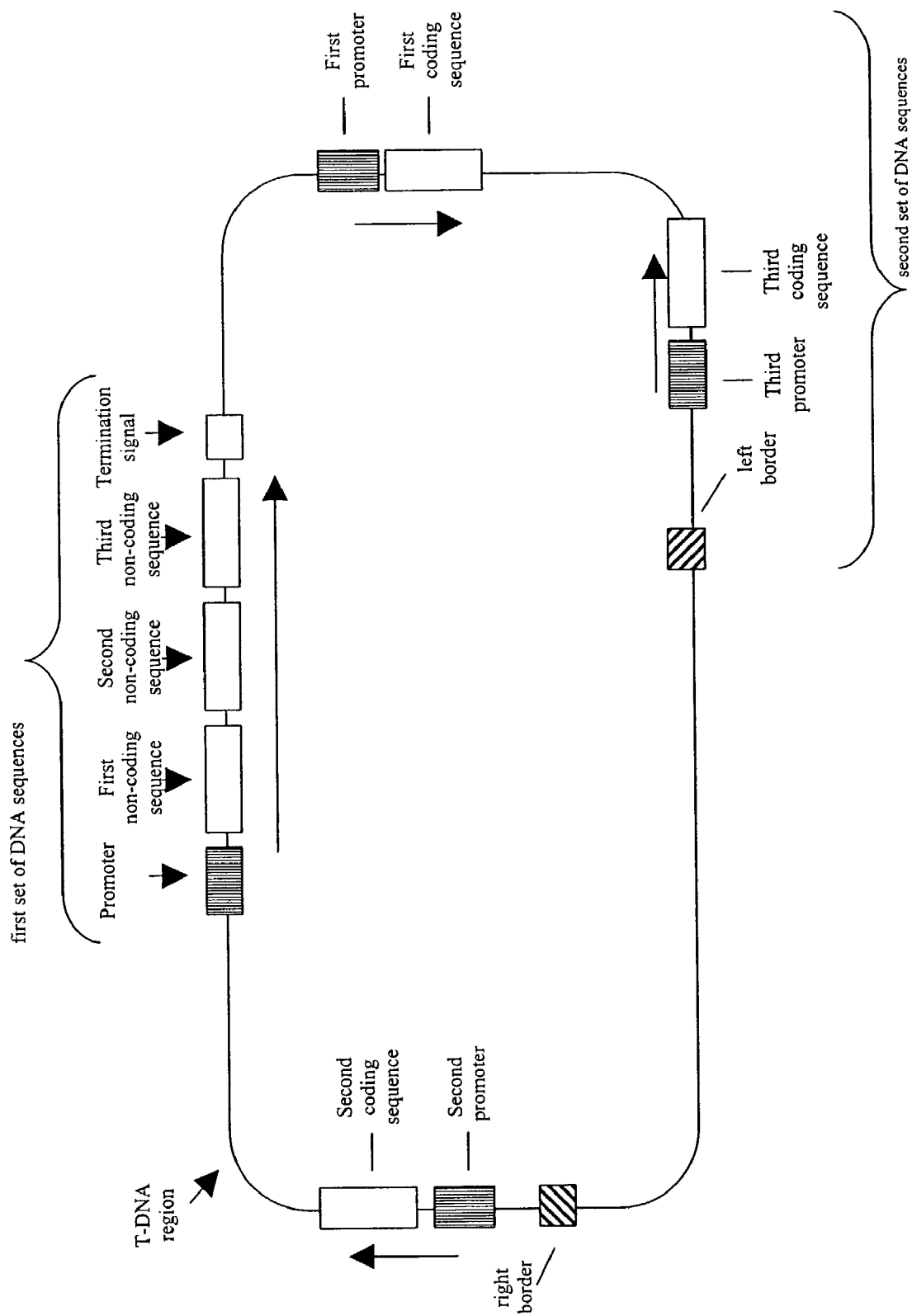
Figure 4:
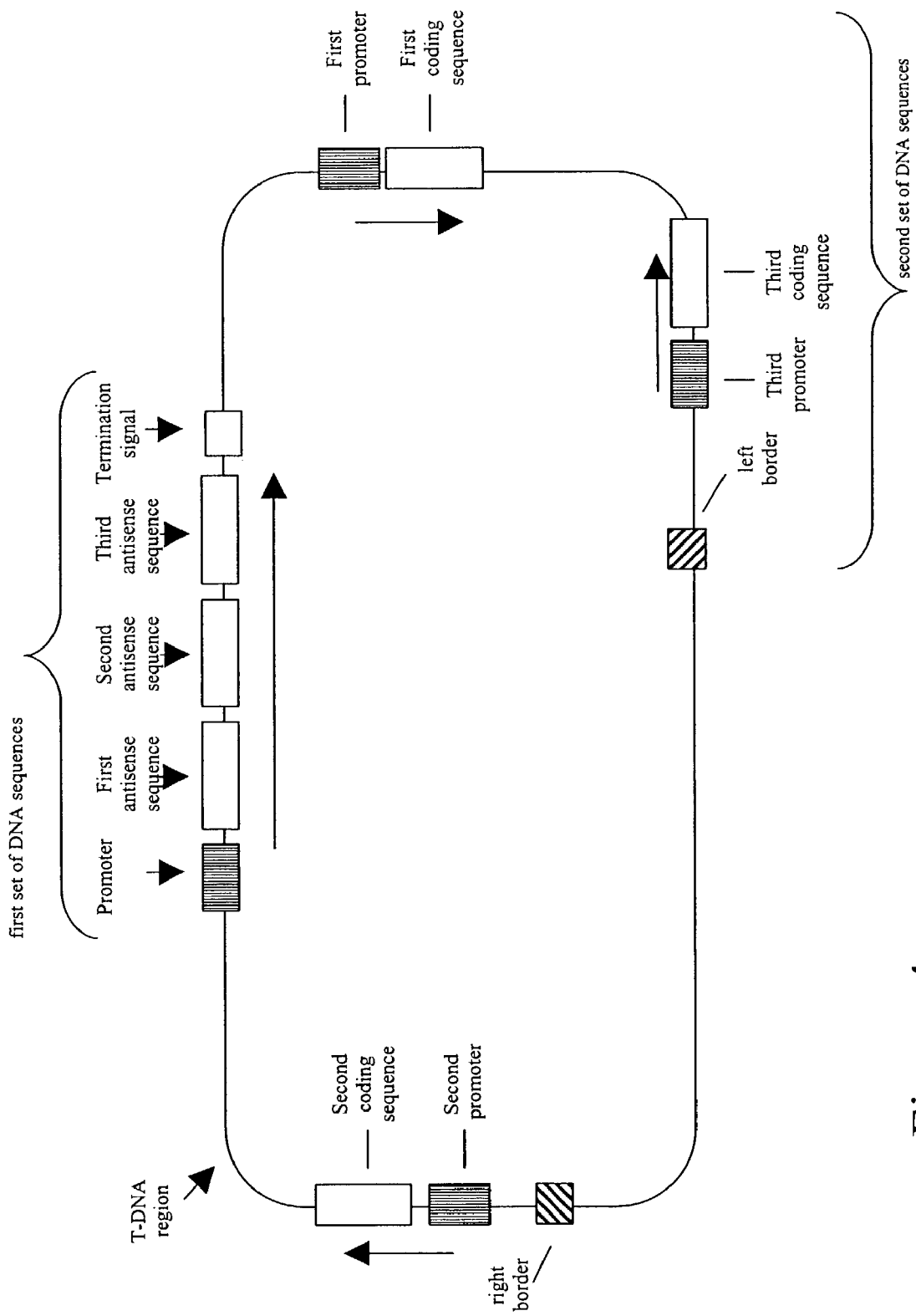

Referring now to FIGS. 3 and 4, the illustrated nucleic acid molecule comprises a T-DNA region flanked by a right border and a left border, on which are located the first and second sets of DNA sequences. The first set of DNA sequences is operably linked to a promoter and a transcriptional termination signal. The second set of DNA sequences that comprises a first promoter operably linked to a first coding sequence, a second promoter operably linked to a second coding sequence, and a third promoter operably linked to a third coding sequence. The transcriptional termination signal can be any transcriptional termination signal functional in a plant, or any plant transcriptional termination signal. Preferred transcriptional termination signals include, but are not limited to, a pea Rubisco E9 3' sequence, a Brassica napin 3' sequence, a tml 3' sequence, and a nos 3' sequence.

In the embodiment depicted in FIG. 3, the first set of DNA sequences, when expressed, is capable of forming a sense cosuppression construct that is capable of suppressing the expression of one or more proteins or transcripts encoded by, or derived from, a gene selected from the group consisting of FAD2, FAD3, and FATB. The first set of DNA sequences comprises three non-coding sequences, each of which expresses an RNA sequence (not shown) that exhibits identity to one or more non-coding region(s) of a gene selected from the group consisting of FAD2, FAD3, and FATB genes. The non-coding sequences each express an RNA sequence that exhibits at least 90% identity to one or more non-coding region(s) of a gene selected from the group consisting of FAD2, FAD3, and FA TB genes. The order of the non-coding sequences within the first set of DNA sequences may be altered from that illustrated and described herein, but the non-coding sequences are arranged in a sense orientation relative to the promoter.

FIG. 4 depicts an embodiment in which the first set of DNA sequences, when expressed, is capable of forming an antisense construct that is capable of suppressing the expression of one or more proteins or transcripts encoded by, or derived from, a gene selected from the group consisting of FAD2, FAD3, and FA TB. The first set of DNA sequences comprises three antisense sequences, each of which expresses an antisense RNA sequence (not shown) that exhibits identity to one or more non-coding region(s) of a gene selected from the group consisting of FAD2, FAD3, and FATB genes. The antisense sequences each express an antisense RNA sequence that exhibits at least 90% identity to one or more non-coding region(s) of a gene selected from the group consisting of FAD2, FAD3, and FATB genes. The order of the antisense sequences within the first set of DNA sequences may be altered from that illustrated and described herein, but the antisense sequences are arranged in an antisense orientation relative to the promoter.

The above-described nucleic acid molecules are preferred embodiments which achieve the objects, features and advantages of the present invention. It is not intended that the present invention be limited to the illustrated embodiments. The arrangement of the sequences in the first and second sets of DNA sequences within the nucleic acid molecule is not limited to the illustrated and described arrangements, and may be altered in any manner suitable for achieving the objects, features and advantages of the present invention as described herein and illustrated in the accompanying drawings.

E. Transgenic Organisms, and Methods for Producing Same

Any of the nucleic acid molecules and constructs of the invention may be introduced into a plant or plant cell in a permanent or transient manner. Preferred nucleic acid molecules and constructs of the present invention are described above in Parts A through D of the Detailed Description, and in the Examples. Another embodiment of the invention is directed to a method of producing transgenic plants which generally comprises the steps of selecting a suitable plant or plant cell, transforming the plant or plant cell with a recombinant vector, and obtaining a transformed host cell.

In a preferred embodiment the plant or cell is, or is derived from, a plant involved in the production of vegetable oils for edible and industrial uses. Especially preferred are temperate oilseed crops. Plants of interest include, but are not limited to, rapeseed (canola and High Erucic Acid varieties), maize, soybean, crambe, mustard, castor bean, peanut, sesame, cotton, linseed, safflower, oil palm, flax, sunflower, and coconut. The invention is applicable to monocotyledonous or dicotyledonous species alike, and will be readily applicable to new and/or improved transformation and regulatory techniques.

Methods and technology for introduction of DNA into plant cells are well known to those of skill in the art, and virtually any method by which nucleic acid molecules may be introduced into a cell is suitable for use in the present invention. Non-limiting examples of suitable methods include: chemical methods; physical methods such as microinjection, electroporation, the gene gun, microprojectile bombardment, and vacuum infiltration; viral vectors; and receptor-mediated mechanisms. Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

Agrobacterium-mediated transfer is a widely applicable system for introducing genes into plant cells. See, e.g., Fraley et al., *Bio/Technology* 3:629-635 (1985); Rogers et al., *Methods Enzymol.* 153:253-277 (1987). The region of DNA to be transferred is defined by the border sequences and intervening DNA is usually inserted into the plant genome. Spielmann et al., *Mol. Gen. Genet.* 205:34 (1986). Modern Agrobacterium transformation vectors are capable of replication in *E. coli* as well as Agrobacterium, allowing for convenient manipulations. Klee et al., In: *Plant DNA Infectious Agents*, Hohn and Schell (eds.), Springer-Verlag, New York, pp. 179-203 (1985).

The regeneration, development and cultivation of plants from single plant protoplast transformants or from various transformed explants is well known in the art. See generally, Maliga et al., *Methods in Plant Molecular Biology*, Cold Spring Harbor Press (1995); Weissbach and Weissbach, In: *Methods for Plant Molecular Biology*, Academic Press, San Diego, Calif. (1988). Plants of the present invention can be part of or generated from a breeding program, and may also be reproduced using apomixis. Methods for the production of apomictic plants are known in the art. See, e.g., U.S. Pat. No. 5,811,636.

In a preferred embodiment, a plant of the present invention that includes nucleic acid sequences which when expressed are capable of selectively reducing the level of a FAD2, FAD3, and/or FATB protein, and/or a FAD2, FAD3, and/or FATB transcript is mated with another plant of the present invention that includes nucleic acid sequences which when expressed are capable of overexpressing another enzyme. Preferably the other enzyme is selected from the group consisting of beta-ketoacyl-ACP synthase I, beta-ketoacyl-ACP synthase IV, delta-9 desaturase, and CP4 EPSPS.

F. Products of the Present Invention

The plants of the present invention may be used in whole or in part. Preferred plant parts include reproductive or storage parts. The term "plant parts" as used herein includes, without limitation, seed, endosperm, ovule, pollen, roots, tubers, stems, leaves, stalks, fruit, berries, nuts, bark, pods, seeds and flowers. In a particularly preferred embodiment of the present invention, the plant part is a seed.

Any of the plants or parts thereof of the present invention may be processed to produce a feed, meal, protein, or oil preparation. A particularly preferred plant part for this purpose is a seed. In a preferred embodiment the feed, meal, protein or oil preparation is designed for livestock animals, fish or humans, or any combination. Methods to produce feed, meal, protein and oil preparations are known in the art. See, e.g., U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v.

In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such an oil may exhibit enhanced oxidative stability. Also, such oil may be a minor or major component of any resultant product.

Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

Seeds of the plants may be placed in a container. As used herein, a container is any object capable of holding such seeds. A container preferably contains greater than about 500, 1,000, 5,000, or 25,000 seeds where at least about 10%, 25%, 50%, 75% or 100% of the seeds are derived from a plant of the present invention. The present invention also provides a container of over about 10,000, more preferably about 20,000, and even more preferably about 40,000 seeds where over about 10%, more preferably about 25%, more preferably 50% and even more preferably about 75% or 90% of the seeds are seeds derived from a plant of the present invention. The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

G. Oil Compositions

For many oil applications, saturated fatty acid levels are preferably less than 8% by weight, and more preferably about 2-3% by weight. Saturated fatty acids have high melting points which are undesirable in many applications. When used as a feedstock for fuel, saturated fatty acids cause clouding at low temperatures, and confer poor cold flow properties such as pour points and cold filter plugging points to the fuel. Oil products containing low saturated fatty acid levels may be preferred by consumers and the food industry because they are perceived as healthier and/or may be labeled as "saturated fat free" in accordance with FDA guidelines. In addition, low saturate oils reduce or eliminate the need to winterize the oil for food applications such as salad oils. In biodiesel and lubricant applications oils with low saturated fatty acid levels confer improved cold flow properties and do not cloud at low temperatures.

The factors governing the physical properties of a particular oil are complex. Palmitic, stearic and other saturated fatty acids are typically solid at room temperature, in contrast to the unsaturated fatty acids, which remain liquid. Because saturated fatty acids have no double bonds in the acyl chain, they remain stable to oxidation at elevated temperatures. Saturated fatty acids are important components in margarines and chocolate formulations, but for many food applications, reduced levels of saturated fatty acids are desired.

Oleic acid has one double bond, but is still relatively stable at high temperatures, and oils with high levels of oleic acid are suitable for cooking and other processes where heating is required. Recently, increased consumption of high oleic oils has been recommended, because oleic acid appears to lower blood levels of low density lipoproteins ("LDLs") without affecting levels of high density lipoproteins ("HDLs"). However, some limitation of oleic acid levels is desirable, because when oleic acid is degraded at high temperatures, it creates negative flavor compounds and diminishes the positive flavors created by the oxidation of linoleic acid. Neff et al., *JAOCS,* 77:1303-1313 (2000); Warner et al., *J. Agric. Food Chem.* 49:899-905 (2001). Preferred oils have oleic acid levels that are 65-85% or less by weight, in order to limit off-flavors in food applications such as frying oil and fried food. Other preferred oils have oleic acid levels that are greater than 55% by weight in order to improve oxidative stability.

Linoleic acid is a major polyunsaturated fatty acid in foods and is an essential nutrient for humans. It is a desirable component for many food applications because it is a major precursor of fried food flavor substances such as 2,4 decadienal, which make fried foods taste good. However, linoleic acid has limited stability when heated. Preferred food oils have linoleic acid levels that are 10% or greater by weight, to enhance the formation of desirable fried food flavor substances, and also are 25% or less by weight, so that the formation of off-flavors is reduced. Linoleic acid also has cholesterol-lowering properties, although dietary excess can reduce the ability of human cells to protect themselves from oxidative damage, thereby increasing the risk of cardiovascular disease. Toborek et al., *Am J. Clin. J.* 75:119-125 (2002). See generally *Flavor Chemistry of Lipid Foods*, editors D. B. Min & T. H. Smouse, Am Oil Chem. Soc., Champaign, Ill. (1989).

Linoleic acid, having a lower melting point than oleic acid, further contributes to improved cold flow properties desirable in biodiesel and biolubricant applications. Preferred oils for most applications have linoleic acid levels of 30% or less by weight, because the oxidation of linoleic acid limits the useful storage or use-time of frying oil, food, feed, fuel and lubricant products. See generally, *Physical Properties of Fats, Oils, and Emulsifiers*, ed. N. Widlak, AOCS Press (1999); Erhan & Asadauskas, *Lubricant Basestocks from Vegetable Oils, Industrial Crops and Products,* 11:277-282 (2000). In addition, high linoleic acid levels in cattle feed can lead to undesirably high levels of linoleic acid in the milk of dairy cattle, and therefore poor oxidative stability and flavor. Timmons et al., *J. Dairy Sci.* 84:2440-2449 (2001). A broadly useful oil composition has linoleic acid levels of 10-25% by weight.

Linolenic acid is also an important component of the human diet. It is used to synthesize the ω-3 family of long-chain fatty acids and the prostaglandins derived therefrom. However, its double bonds are highly susceptible to oxidation, so that oils with high levels of linolenic acid deteriorate rapidly on exposure to air, especially at high temperatures. Partial hydrogenation of such oils is often necessary before they can be used in food products to retard the formation of off-flavors and rancidity when the oil is heated, but hydrogenation creates unhealthy trans fatty acids which can contribute to cardiovascular disease. To achieve improved oxidative stability, and reduce the need to hydrogenate oil, preferred oils have linolenic acid levels that are 8% or less by weight, 6% or less, 4% or less, and more preferably 0.5-2% by weight of the total fatty acids in the oil of the present invention.

The oil of the present invention can be a blended oil, synthesized oil or in a preferred embodiment an oil generated from an oilseed having an appropriate oil composition. In a preferred embodiment, the oil is a soybean oil. The oil can be a crude oil such as crude soybean oil, or can be a processed oil, for example the oil can be refined, bleached, deodorized, and/or winterized. As used herein, "refining" refers to a process of treating natural or processed fat or oil to remove impurities, and may be accomplished by treating fat or oil with caustic soda, followed by centrifugation, washing with water, and heating under vacuum. "Bleaching" refers to a process of treating a fat or oil to remove or reduce the levels of coloring materials in the fat or oil. Bleaching may be accomplished by treating fat or oil with activated charcoal or Fullers (diatomaceous) earth. "Deodorizing" refers to a process of removing components from a fat or oil that contribute objectionable flavors or odors to the end product, and may be accomplished by use of high vacuum and superheated steam washing. "Winterizing" refers to a process of removing saturated glycerides from an oil, and may be accomplished by chilling and removal of solidified portions of fat from an oil.

A preferred oil of the present invention has a low saturate oil composition, or a zero saturate oil composition. In other preferred embodiments, oils of the present invention have increased oleic acid levels, reduced saturated fatty levels, and reduced polyunsaturated fatty acid levels. In a preferred embodiment, the oil is a soybean oil. The percentages of fatty acid content, or fatty acid levels, used herein refer to percentages by weight.

In a first embodiment, an oil of the present invention preferably has an oil composition that is 55 to 80% oleic acid, 10 to 40% linoleic acid, 6% or less linolenic acid, and 2 to 8% saturated fatty acids; more preferably has an oil composition that is 55 to 80% oleic acid, 10 to 39% linoleic acid, 4.5% or less linolenic acid, and 3 to 6% saturated fatty acids; and even more preferably has an oil composition that is 55 to 80% oleic acid, 10 to 39% linoleic acid, 3.0% or less linolenic acid, and 2 to 3.6% saturated fatty acids.

In a second embodiment, an oil of the present invention preferably has an oil composition that is 65 to 80% oleic acid, 10 to 30% linoleic acid, 6% or less linolenic acid, and 2 to 8% saturated fatty acids; more preferably has an oil composition that is 65 to 80% oleic acid, 10 to 29% linoleic acid, 4.5% or less linolenic acid, and 3 to 6% saturated fatty acids; and even more preferably has an oil composition that is 65 to 80% oleic acid, 10 to 29% linoleic acid, 3.0% or less linolenic acid, and 2 to 3.6% saturated fatty acids.

In other embodiments, the percentage of oleic acid is 50% or greater; 55% or greater; 60% or greater; 65% or greater; 70% or greater; 75% or greater; or 80% or greater; or is a range from 50 to 80%; 55 to 80%; 55 to 75%; 55 to 65%; 65 to 80%; 65 to 75%; 65 to 70%; or 69 to 73%. Suitable percentage ranges for oleic acid content in oils of the present invention also include ranges in which the lower limit is selected from the following percentages: 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 percent; and the upper limit is selected from the following percentages: 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 percent.

In these other embodiments, the percentage of linoleic acid in an oil of the present invention is a range from 10 to 40%; 10 to $^{39}$%; 10 to 30%; 10 to 29%; 10 to 28%; 10 to 25%; 10 to 21%; 10 to 20%; 11 to 30%; 12 to 30%; 15 to 25%; 20 to 25%; 20 to 30%; or 21 to 24%. Suitable percentage ranges for linoleic acid content in oils of the present invention also include ranges in which the lower limit is selected from the following percentages: 10, 11, 12, 13, 14, 15, 16, 17, 18, 19, 20, 21, 22, 23, 24, 25, 26, 27, 28, 29, or 30 percent; and the upper limit is selected from the following percentages: 20, 21, 22, 23, 24, 25, 26, 27, 28, 29, 30, 31, 32, 33, 34, 35, 36, 37, 38, 39, or 40 percent.

In these other embodiments, the percentage of linolenic acid in an oil of the present invention is 10% or less; 9% or less; 8% or less; 7% or less; 6% or less; 5% or less; 4.5% or less; 4% or less; 3.5% or less; 3% or less; 3.0% or less; 2.5% or less; or 2% or less; or is a range from 0.5 to 2%; 0.5 to 3%; 0.5 to 4.5%; 0.5% to 6%; 3 to 5%; 3 to 6%; 3 to 8%; 1 to 2%; 1 to 3%; or 1 to 4%. In these other embodiments, the percentage of saturated fatty acids in an oil composition of the present invention is 15% or less; 14% or less; 13% or less; 12% or less, 11% or less; 10% or less; 9% or less; 8% or less; 7% or less; 6% or less; 5% or less; 4% or less; or 3.6% or less; or is a range from 2 to 3%; 2 to 3.6%; 2 to 4%; 2 to 8%; 3 to 15%; 3 to 10%;3 to 8%;3 to 6%;3.6 to 7%;5 to 8%;7 to 10%; or 10 to 15%.

An oil of the present invention is particularly suited to use as a cooking or frying oil. Because of its reduced polyunsaturated fatty acid content, the oil of the present invention does not require the extensive processing of typical oils because fewer objectionable odorous and colorant compounds are present. In addition, the low saturated fatty acid content of the present oil improves the cold flow properties of the oil, and obviates the need to heat stored oil to prevent it from crystallizing or solidifying. Improved cold flow also enhances drainage of oil from fried food material once it has been removed from frying oil, thereby resulting in a lower fat product. See Bouchon et al., *J. Food Science* 66: 918-923 (2001). The low levels of linolenic acid in the present oil are particularly advantageous in frying to reduce off-flavors.

The present oil is also well-suited for use as a salad oil (an oil that maintains clarity at refrigerator temperatures of 40-50 degrees Fahrenheit). Its improved clarity at refrigerator temperatures, due to its low saturated fatty acid and moderate linoleic acid content, reduces or eliminates the need to winterize the oil before use as a salad oil.

In addition, the moderate linoleic acid and low linolenic acid content of the present oil make it well-suited for the production of shortening, margarine and other semi-solid vegetable fats used in foodstuffs. Production of these fats typically involves hydrogenation of unsaturated oils such as soybean oil, corn oil, or canola oil. The increased oxidative and flavor stability of the present oil mean that it need not be hydrogenated to the extent that typical vegetable oil is for uses such as margarine and shortening, thereby reducing processing costs and the production of unhealthy trans isomers.

An oil of the present invention is also suitable for use as a feedstock to produce biodiesel, particularly because biodiesel made from such an oil has improved cold flow, improved ignition quality (cetane number), improved oxidative stability, and reduced nitric oxide emissions. Biodiesel is an alternative diesel fuel typically comprised of methyl esters of saturated, monounsaturated, and polyunsaturated $C_{16}$-$C_{22}$ fatty acids. Cetane number is a measure of ignition quality— the shorter the ignition delay time of fuel in the engine, the higher the cetane number. The ASTM standard specification for biodiesel fuel (D 6751-$O_2$) requires a minimum cetane number of 47.

The use of biodiesel in conventional diesel engines results in substantial reductions of pollutants such as sulfates, carbon monoxide, and particulates compared to petroleum diesel fuel, and use in school buses can greatly reduce children's exposure to toxic diesel exhaust. A limitation to the use of 100% conventional biodiesel as fuel is the high cloud point of conventional soy biodiesel (2 degrees C.) compared to number 2 diesel (−16 degrees C.). Dunn et al., *Recent. Res. Devel. in Oil Chem.*, 1:31-56 (1997). Biodiesel made from oil of the present invention has an improved (reduced) cloud point and cold filter plugging point, and may also be used in blends to improve the cold-temperature properties of biodiesel made from inexpensive but highly saturated sources of fat such as animal fats (tallow, lard, chicken fat) and palm oil. Biodiesel can also be blended with petroleum diesel at any level.

Biodiesel is typically obtained by extracting, filtering and refining soybean oil to remove free fats and phospholipids, and then transesterifying the oil with methanol to form methyl esters of the fatty acids. See, e.g., U.S. Pat. No. 5,891, 203. The resultant soy methyl esters are commonly referred to as "biodiesel." The oil of the present invention may also be used as a diesel fuel without the formation of methyl esters, such as, for example, by mixing acetals with the oil. See, e.g., U.S. Pat. No. 6,013,114. Due to its improved cold flow and oxidative stability properties, the oil of the present invention is also useful as a lubricant, and as a diesel fuel additive. See, e.g., U.S. Pat. Nos. 5,888,947, 5,454,842 and 4,557,734.

Soybeans, and oils of the present invention are also suitable for use in a variety of soyfoods made from whole soybeans, such as soymilk, soy nut butter, natto, and tempeh, and soyfoods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin. Whole soybeans are also edible, and are typically sold to consumers raw, roasted, or as edamamé. Soymilk, which is typically produced by soaking and grinding whole soybeans, may be consumed as is, spray-dried, or processed to form soy yogurt, soy cheese, tofu, or yuba. The present soybean or oil may be advantageously used in these and other soyfoods because of its improved oxidative stability, the reduction of off-flavor precursors, and its low saturated fatty acid level.

The following examples are illustrative and not intended to be limiting in any way.

All publications, patents, and patent applications mentioned in this specification are herein incorporated by reference to the same extent as if each individual publication, patent, or patent application was specifically and individually indicated to be incorporated by reference.

EXAMPLES

Example 1

Suppression Constructs

1A. FAD2-1 Constructs

The FAD2-1A intron (SEQ ID NO: 1) is cloned into the expression cassette, pCGN3892, in sense and antisense orientations. The vector pCGN3892 contains the soybean 7S promoter and a pea rbcS 3'. Both gene fusions are then separately ligated into pCGN9372, a vector that contains the CP4 EPSPS gene regulated by the FMV promoter. The resulting expression constructs (pCGN5469 sense and pCGN5471 antisense) are used for transformation of soybean.

The FAD2-1B intron (SEQ ID NO: 2) is fused to the 3' end of the FAD2-1A intron in plasmid pCGN5468 (contains the soybean 7S promoter fused to the FAD2-1A intron (sense) and a pea rbcS 3') or pCGN5470 (contains the soybean 7S promoter fused to the FAD2-1A intron (antisense) and a pea rbcS 3') in sense or antisense orientation respectively. The resulting intron combination fusions are then ligated separately into pCGN9372, a vector that contains the CP4 EPSPS gene regulated by the FMV promoter. The resulting expression constructs (pCGN5485, FAD2-1A & FAD2-1B intron sense and pCGN5486, FAD2-1A & FAD2-1B intron antisense) are used for transformation of soybean.

1B. FAD3-1 Constructs

FAD3-1A introns #1, #2, #4 and #5 (SEQ ID NOs: 7, 8, 10 and 11, respectively), FAD3-1B introns #3C (SEQ ID NO: 23) and #4 (SEQ ID NO: 24), are all ligated separately into pCGN3892, in sense or antisense orientations. pCGN3892 contains the soybean 7S promoter and a pea rbcS 3'. These fusions are ligated into pCGN9372, a vector that contains the CP4 EPSPS gene regulated by the FMV promoter for transformation into soybean. The resulting expression constructs (pCGN5455, FAD3-1A intron #4 sense; pCGN5459, FAD3-1A intron #4 antisense; pCGN5456, FAD3 intron #5 sense; pCGN5460, FAD3-1A intron #5 antisense; pCGN5466, FAD3-1A intron #2 antisense; pCGN5473, FAD3-1A intron #1 antisense) are used for transformation of soybean.

1C. FatB Constructs

The soybean FATB intron II sequence (SEQ ID NO: 30) is amplified via PCR using a FATB partial genomic clone as a template. PCR amplification is carried out as follows: 1 cycle, 95° C. for 10 min; 25 cycles, 95° C. for 30 sec, 62° C. for 30 sec, 72° C. for 30 sec; 1 cycle, 72° C. for 7 min. PCR amplification results in a product that is 854 bp long, including reengineered restriction sites at both ends. The PCR product is cloned directly into the expression cassette pCGN3892 in sense orientation, by way of XhoI sites engineered onto the 5' ends of the PCR primers, to form pMON70674. Vector pCGN3892 contains the soybean 7S promoter and a pea rbcS 3'. pMON70674 is then cut with NotI and ligated into pMON41164, a vector that contains the CP4 EPSPS gene regulated by the FMV promoter. The resulting gene expression construct, pMON70678, is used for transformation of soybean using Agrobacterium methods.

Two other expression constructs containing the soybean FATB intron II sequence (SEQ ID NO: 30) are created. pMON70674 is cut with NotI and ligated into pMON70675 which contains the CP4 EPSPS gene regulated by the FMV promoter and the KAS IV gene regulated by the napin promoter, resulting in pMON70680. The expression vector pMON70680 is then cut with SnaBI and ligated with a gene fusion of the jojoba delta-9 desaturase gene (SEQ ID NO: 41) in sense orientation regulated by the 7S promoter. The expression constructs pMON70680 and pMON70681 are used for transformation of soybean using Agrobacterium methods.

1D. Combination Constructs

Expression constructs are made containing various permutations of a first set of DNA sequences. The first set of DNA sequences are any of those described, or illustrated in FIGS. 5 and 6, or any other set of DNA sequences that contain either various combinations of sense and antisense FAD2, FAD3, and FATB non-coding regions so that they are capable of forming dsRNA constructs, sense cosuppression constructs, antisense constructs, or various combinations of the foregoing.

Figure 5A:
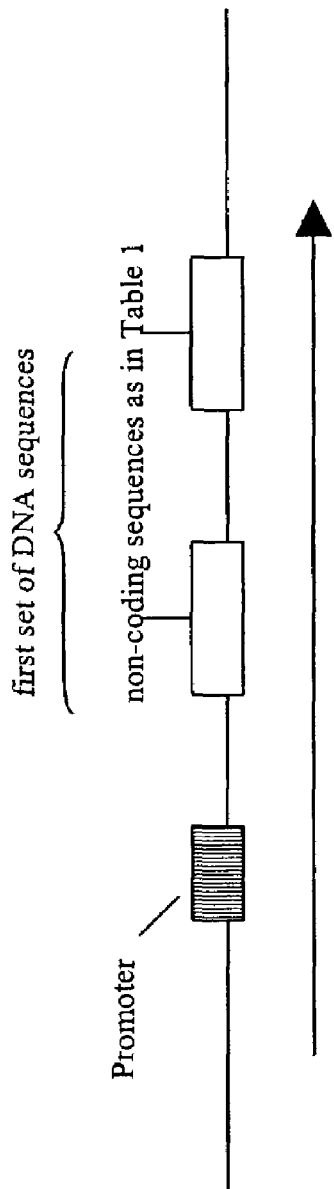
FIGS. 5 and 6 each depict illustrative configurations of a first set of DNA sequences.
Figure 5B:
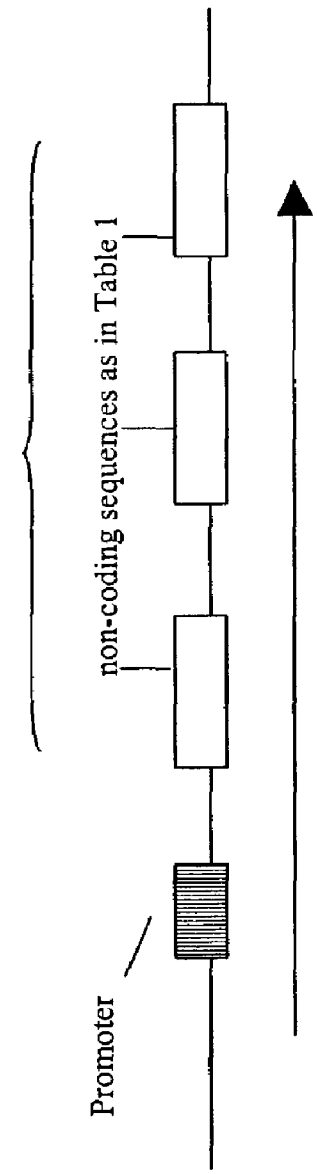
Figure 5C:
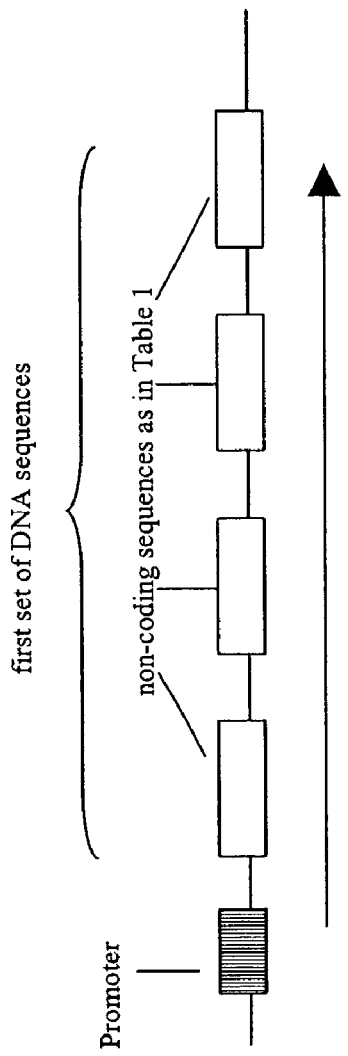
Figure 5D:
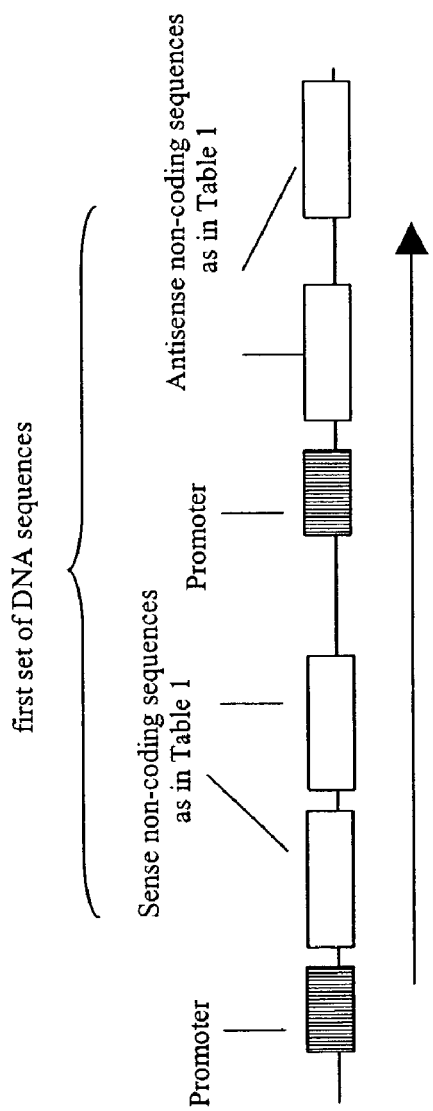

FIGS. 5(a)-(c) depict several first sets of DNA sequences which are capable of expressing sense cosuppression or antisense constructs according to the present invention, the non-coding sequences of which are described in Tables 1 and 2 below. The non-coding sequences may be single sequences, combinations of sequences (e.g., the 5'UTR linked to the 3'UTR), or any combination of the foregoing. To express a sense cosuppression construct, all of the non-coding sequences are sense sequences, and to express an antisense construct, all of the non-coding sequences are antisense sequences. FIG. 5(d) depicts a first set of DNA sequences which is capable of expressing sense and antisense constructs according to the present invention.

Figure 6A:
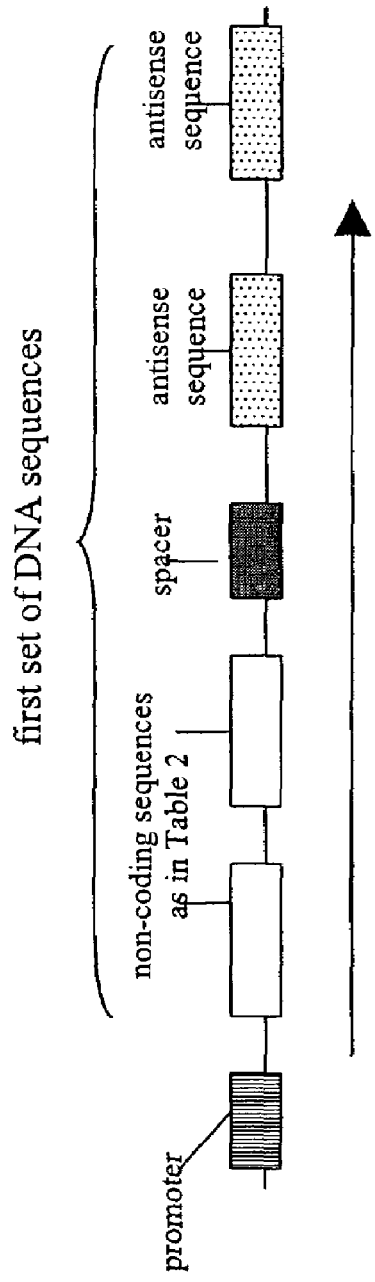
Figure 6B:
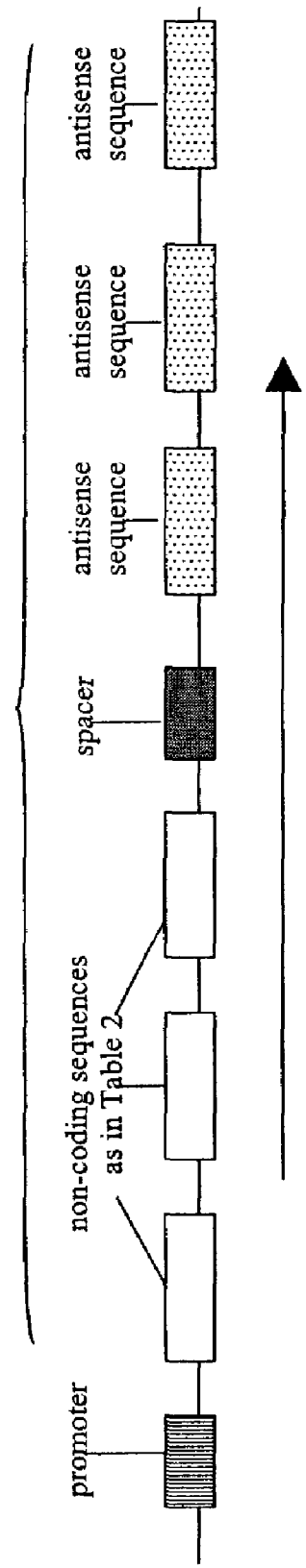
Figure 6C:
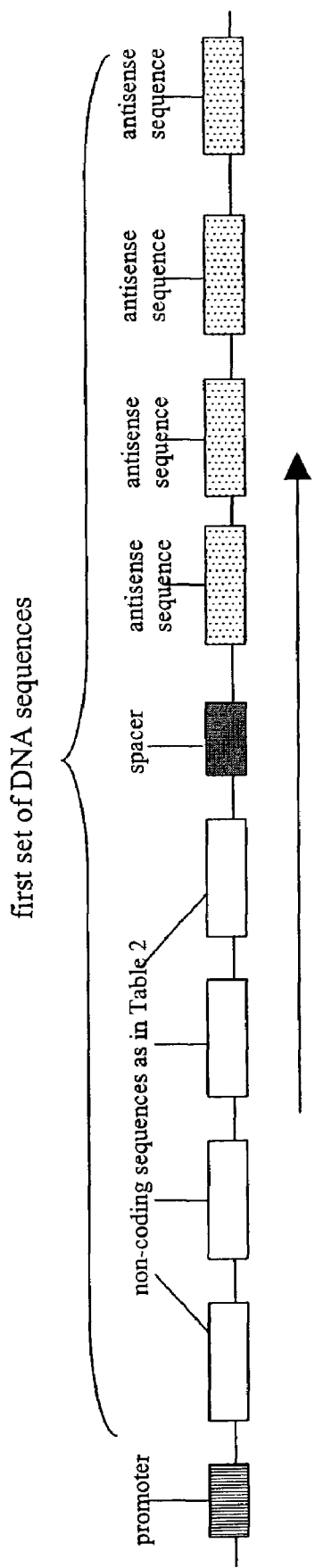

FIGS. 6(a)-(c) depict several first sets of DNA sequences which are capable of expressing dsRNA constructs according to the present invention, the non-coding sequences of which are described in Tables 1 and 2 below. The first set of DNA sequences depicted in FIG. 6 comprises pairs of related sense and antisense sequences, arranged such that, e.g., the RNA expressed by the first sense sequence is capable of forming a double-stranded RNA with the antisense RNA expressed by the first antisense sequence. For example, referring to FIG. 6(a) and illustrative combination No. 1 (of Table 1), the first set of DNA sequences comprises a sense FAD2-1 sequence, a sense FAD3-1 sequence, an antisense FAD2-1 sequence and an antisense FAD3-1 sequence. Both antisense sequences correspond to the sense sequences so that the expression products of the first set of DNA sequences are capable of forming a double-stranded RNA with each other. The sense sequences may be separated from the antisense sequences by a spacer sequence, preferably one that promotes the formation of a dsRNA molecule. Examples of such spacer sequences include those set forth in Wesley et al., supra, and Hamilton et al., *Plant J.*, 15:737-746 (1988). The promoter is any promoter functional in a plant, or any plant promoter. Non-limiting examples of suitable promoters are described in Part D of the Detailed Description.

The first set of DNA sequences is inserted in an expression construct in either the sense or anti-sense orientation using a variety of DNA manipulation techniques. If convenient restriction sites are present in the DNA sequences, they are inserted into the expression construct by digesting with the restriction endonucleases and ligation into the construct that has been digested at one or more of the available cloning sites. If convenient restriction sites are not available in the DNA sequences, the DNA of either the construct or the DNA sequences is modified in a variety of ways to facilitate cloning of the DNA sequences into the construct. Examples of methods to modify the DNA include by PCR, synthetic linker or adapter ligation, in vitro site-directed mutagenesis, filling in or cutting back of overhanging 5' or 3' ends, and the like.

These and other methods of manipulating DNA are well known to those of ordinary skill in the art.

sequences are labeled in normal text, and antisense sequences are labeled in upside-down text. The abbreviations used in

TABLE 1

| Illustrative Combinations | Non-Coding Sequences (sense or antisense) | | | |
|---|---|---|---|---|
| | First | Second | Third | Fourth |
| 1 | FAD2-1A or B | FAD3-1A or B or C | | |
| 2 | FAD3-1A or B or C | FAD2-1A or B | | |
| 3 | FAD2-1A or B | FAD3-1A or B or C | different FAD3-1A or B or C sequence | |
| 4 | FAD2-1A or B | FAD3-1A or B or C | FATB | |
| 5 | FAD2-1A or B | FATB | FAD3-1A or B or C | |
| 6 | FAD3-1A or B or C | FAD2-1A or B | FATB | |
| 7 | FAD3-1A or B or C | FATB | FAD2-1A or B | |
| 8 | FATB | FAD3-1A or B or C | FAD2-1A or B | |
| 9 | FATB | FAD2-1A or B | FAD3-1A or B or C | |
| 10 | FAD2-1A or B | FAD3-1A or B or C | different FAD3-1A or B or C sequence | FATB |
| 11 | FAD3-1A or B or C | FAD2-1A or B | different FAD3-1A or B or C sequence | FATB |
| 12 | FAD3-1A or B or C | different FAD3-1A or B or C sequence | FAD2-1A or B | FATB |
| 13 | FAD2-1A or B | FAD3-1A or B or C | FATB | different FAD3-1A or B or C sequence |
| 14 | FAD3-1A or B or C | FAD2-1A or B | FATB | different FAD3-1A or B or C sequence |
| 15 | FAD3-1A or B or C | different FAD3-1A or B or C sequence | FATB | FAD2-1A or B |
| 16 | FAD2-1A or B | FATB | FAD3-1A or B or C | different FAD3-1A or B or C sequence |
| 17 | FAD3-1A or B or C | FATB | FAD2-1A or B | different FAD3-1A or B or C sequence |
| 18 | FAD3-1A or B or C | FATB | different FAD3-1A or B or C sequence | FAD2-1A or B |
| 19 | FATB | FAD2-1A or B | FAD3-1A or B or C | different FAD3-1A or B or C sequence |
| 20 | FATB | FAD3-1A or B or C | FAD2-1A or B | different FAD3-1A or B or C sequence |
| 21 | FATB | FAD3-1A or B or C | different FAD3-1A or B or C sequence | FAD2-1A or B |

TABLE 2

Correlation of SEQ ID NOs with Sequences in Table 1

| | FAD2-1A | FAD2-1B | FAD3-1A | FAD3-1B | FAD3-1C | FATB |
|---|---|---|---|---|---|---|
| 3' UTR | SEQ NO: 5 | n/a | SEQ NO: 16 | SEQ NO: 26 | n/a | SEQ NO: 36 |
| 5' UTR | SEQ NO: 6 | n/a | SEQ NO: 17 | SEQ NO: 27 | n/a | SEQ NO: 37 |
| 5' + 3' UTR (or 3' + 5' UTR) | Linked SEQ NOs: 5 and 6 | n/a | Linked SEQ NOs: 16 and 17 | Linked SEQ NOs: 26 and 27 | n/a | Linked SEQ NOs: 36 and 37 |
| Intron #1 | SEQ NO: 1 | SEQ NO: 2 | SEQ NO: 7 | SEQ NO: 19 | n/a | SEQ NO: 29 |
| Intron #2 | n/a | n/a | SEQ NO: 8 | SEQ NO: 20 | n/a | SEQ NO: 30 |
| Intron #3 | n/a | n/a | n/a | n/a | n/a | SEQ NO: 31 |
| Intron #3A | n/a | n/a | SEQ NO: 9 | SEQ NO: 21 | n/a | n/a |
| Intron #3B | n/a | n/a | SEQ NO: 12 | SEQ NO: 22 | n/a | n/a |
| Intron #3C | n/a | n/a | SEQ NO: 13 | SEQ NO: 23 | n/a | n/a |
| Intron #4 | n/a | n/a | SEQ NO: 10 | SEQ NO: 24 | SEQ NO: 14 | SEQ NO: 32 |
| Intron #5 | n/a | n/a | SEQ NO: 11 | SEQ NO: 25 | n/a | SEQ NO: 33 |
| Intron #6 | n/a | n/a | n/a | n/a | n/a | SEQ NO: 34 |
| Intron #7 | n/a | n/a | n/a | n/a | n/a | SEQ NO: 35 |

Example 2

Combination Constructs

In FIGS. 7-15, promoters are indicated by arrows, encoding sequences (both coding and non-coding) are indicated by pentagons which point in the direction of transcription, sense these Figures include: 7Sa=7Sα promoter; 7Sa'=7Sα' promoter; Br napin=Brassica napin promoter; FMV=an FMV promoter; ARC=arcelin promoter; RBC E9 3'=Rubisco E9 termination signal; Nos 3'=nos termination signal; TML 3'=tml termination signal; napin 3'=napin termination signal; '3 (in the same box as FAD or FAT)=3' UTR; 5' (in the same box as FAD or FAT)=5'UTR; Cr=*Cuphea pulcherrima*;

Gm=Glycine max; Rc=*Ricinus communis*; FAB2=a FAB2 allele of a stearoyl-desaturase gene; and Intr or Int=intron.

2A. dsRNA Constructs

Figure 7:
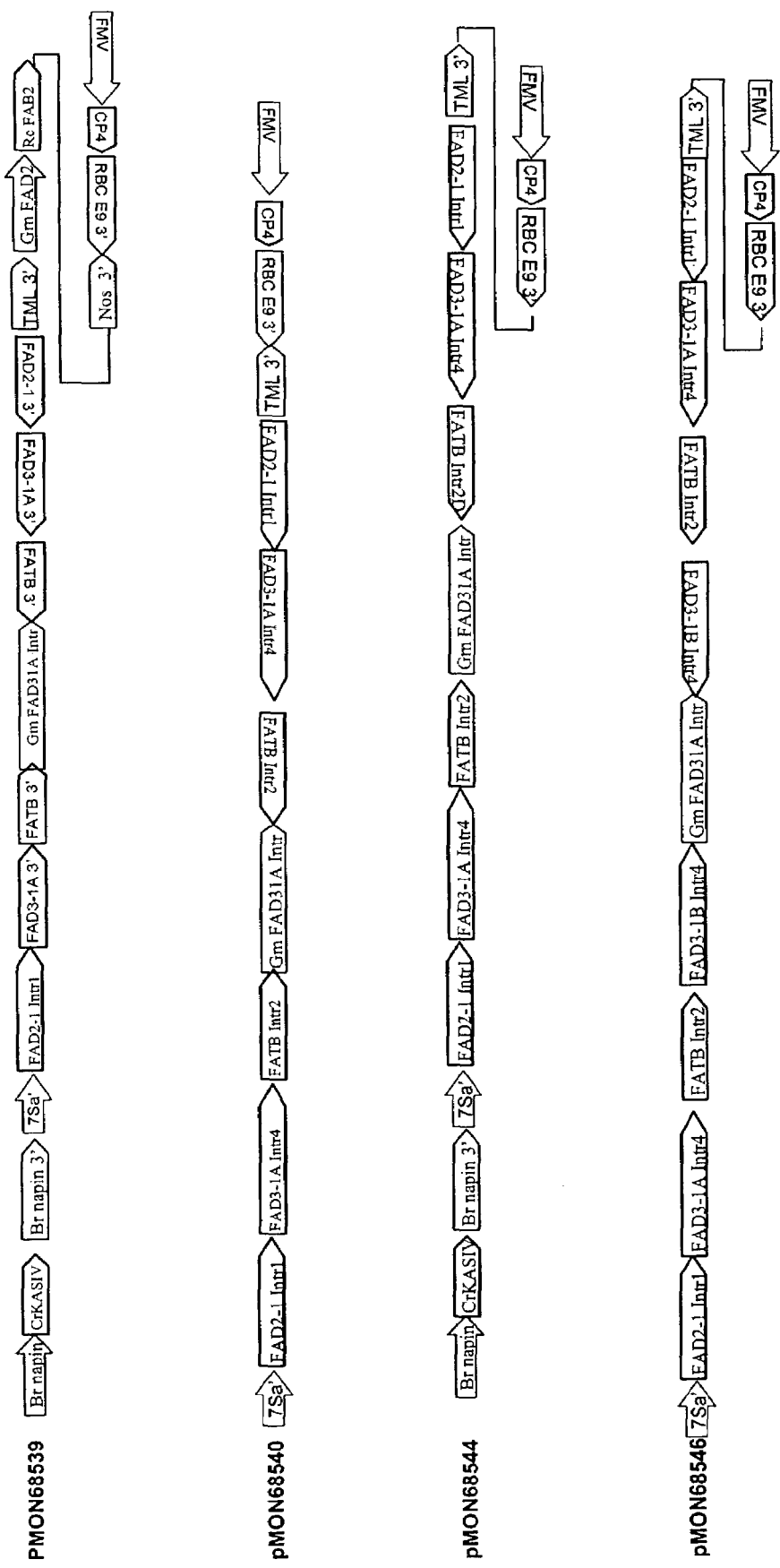
Figure 8:
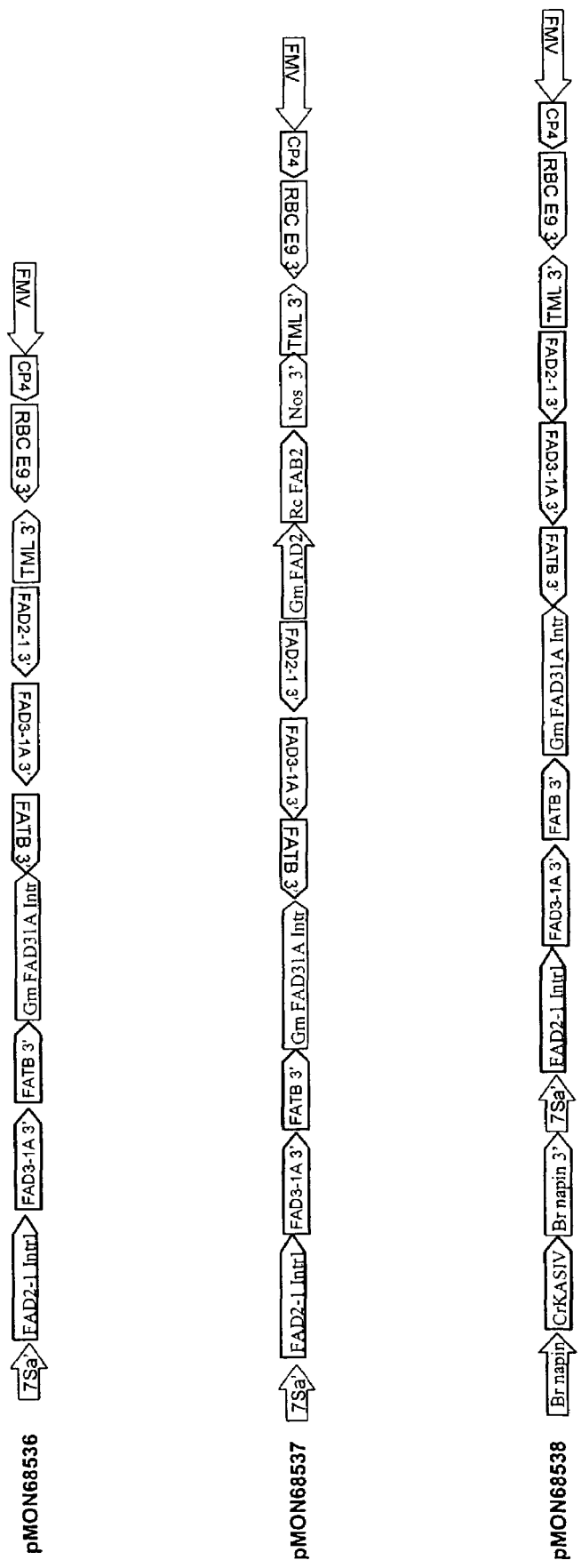
Figure 9:
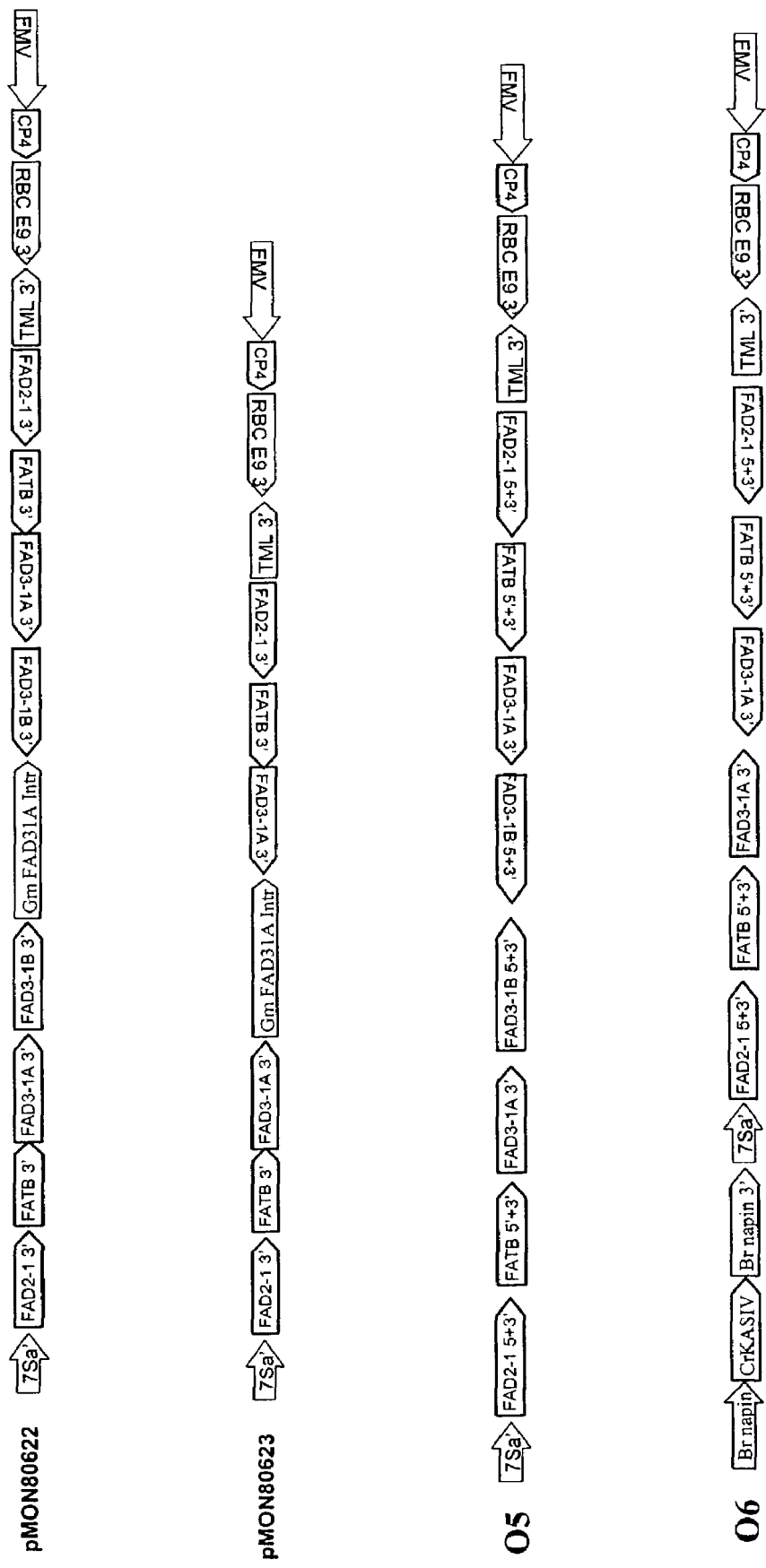

FIGS. 7-9 depict nucleic acid molecules of the present invention in which the first sets of DNA sequences are capable of expressing dsRNA constructs. The first set of DNA sequences depicted in FIGS. 7-9 comprise pairs of related sense and antisense sequences, arranged such that, e.g., the RNA expressed by the first sense sequence is capable of forming a double-stranded RNA with the antisense RNA expressed by the first antisense sequence. The sense sequences may be adjacent to the antisense sequences, or separated from the antisense sequences by a spacer sequence, as shown in FIG. 9.

The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which can be any promoter functional in a plant, or any plant promoter, and may be an FMV promoter, a napin promoter, a 7S (either 7Sα or 7Sα') promoter, an arcelin promoter, a delta-9 desaturase promoter, or a FAD2-1A promoter.

Referring now to FIG. 7, soybean FAD2-1 intron 1 (SEQ ID NO: 1 or 2), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. Vectors containing a *C. pulcherrima* KAS IV gene (SEQ ID NO: 39) regulated by a Brassica napin promoter and a Brassica napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON68539, is depicted in FIG. 7 and is used for transformation using methods as described herein.

Soybean FAD2-1 intron 1 (SEQ ID NO: 1 or 2), FAD3-1A intron 4 (SEQ ID NO: 10), and FATB intron II (SEQ ID NO: 30) sequences are amplified via PCR to result in PCR products that include reengineered restriction sites at both ends. The PCR products are cloned directly, in sense and antisense orientations, separated by a spliceable soybean FAD3-JA intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68540, is depicted in FIG. 7 and is used for transformation using methods as described herein.

Soybean FAD2-1 intron 1 (SEQ ID NO: 1 or 2), FAD3-1A intron 4 (SEQ ID NO: 10), and FATB intron II (SEQ ID NO: 30) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a Brassica napin promoter and a Brassica napin 3' termination sequence is cut with appropriate restriction enzymes, and ligated into pMON41164. The resulting gene expression construct, pMON68544, is depicted in FIG. 7 and is used for transformation using methods as described herein.

Soybean FAD2-1 intron 1 (SEQ ID NO: 1 or 2), FAD3-1A intron 4 (SEQ ID NO: 10), FATB intron II (SEQ ID NO: 30), and FAD3-1B intron 4 (SEQ ID NO: 24) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68546, is depicted in FIG. 7 and is used for transformation using methods as described herein.

Referring now to FIG. 8, soybean FAD2-1 intron 1 (SEQ ID NO: 1 or 2), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68536, is depicted in FIG. 8 and is used for transformation using methods as described herein.

Soybean FAD2-1 intron 1 (SEQ ID NO: 1 or 2), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. A vector containing a *R. communis* delta-9 desaturase (FAB2) gene (SEQ ID NO: 40) regulated by a soybean FAD2 promoter and a nos 3' termination sequence, is cut with appropriate restriction enzymes, and ligated just upstream of the tml 3' termination sequence. The vector is then cut with NotI and ligated into pMON41164, a vector that contains the CP4 EPSPS gene regulated by the FMV promoter and a pea Rubisco E9 3' termination sequence. The resulting gene expression construct, pMON68537, is depicted in FIG. 8 and is used for transformation using methods as described herein.

Soybean FAD2-1 intron 1 (SEQ ID NO: 1 or 2), FAD3-1A 3'UTR (SEQ ID NO: 16), and FATB 3'UTR (SEQ ID NO: 36)

sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a Brassica napin promoter and a Brassica napin 3' termination sequence is cut with appropriate restriction enzymes, and ligated into pMON41164. The resulting gene expression construct, pMON68538, is depicted in FIG. 8 and is used for transformation using methods as described herein.

Referring now to FIG. 9, soybean FAD2-1 3'UTR (SEQ ID NO: 5), FATB 3'UTR (SEQ ID NO: 36), FAD3-1A 3'UTR (SEQ ID NO: 16), and FAD3-1B 3'UTR (SEQ ID NO: 26) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80622, is depicted in FIG. 9 and is used for transformation using methods as described herein.

Soybean FAD2-1 3'UTR (SEQ ID NO: 5), FATB 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80623, is depicted in FIG. 9 and is used for transformation using methods as described herein.

Soybean FAD2-1 5'UTR-3'UTR (SEQ ID NOs: 6 and 5, ligated together), FATB 5'UTR-3'UTR (SEQ ID NOs: 37 and 36, ligated together), FAD3-1A 3'UTR (SEQ ID NO: 16) and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in sense and antisense orientations, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, O5, is depicted in FIG. 9 and is used for transformation using methods as described herein.

Soybean FAD2-1 5'UTR-3'UTR (SEQ ID NOs: 6 and 5, ligated together), FATB 5'UTR-3'UTR (SEQ ID NOs: 37 and 36, ligated together) and FAD3-1A 3'UTR (SEQ ID NO: 16) sequences are amplified via PCR to result in PCR products that include reengineered restriction sites at both ends. The PCR products are cloned directly, in sense and antisense orientations, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a Brassica napin promoter and a Brassica napin 3' termination sequence is cut with appropriate restriction enzymes, and ligated into pMON41164. The resulting gene expression construct, 06, is depicted in FIG. 9 and is used for transformation using methods as described herein.

2B. Sense Cosuppression Constructs

FIGS. 10-13 depict nucleic acid molecules of the present invention in which the first sets of DNA sequences are capable of expressing sense cosuppression constructs. The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which is any promoter functional in a plant, or any plant promoter, and may be an FMV promoter, a napin promoter, a 7S promoter (either 7Sα or 7Sα'), an arcelin promoter, a delta-9 desaturase promoter, or a FAD2-1A promoter.

Figure 10:
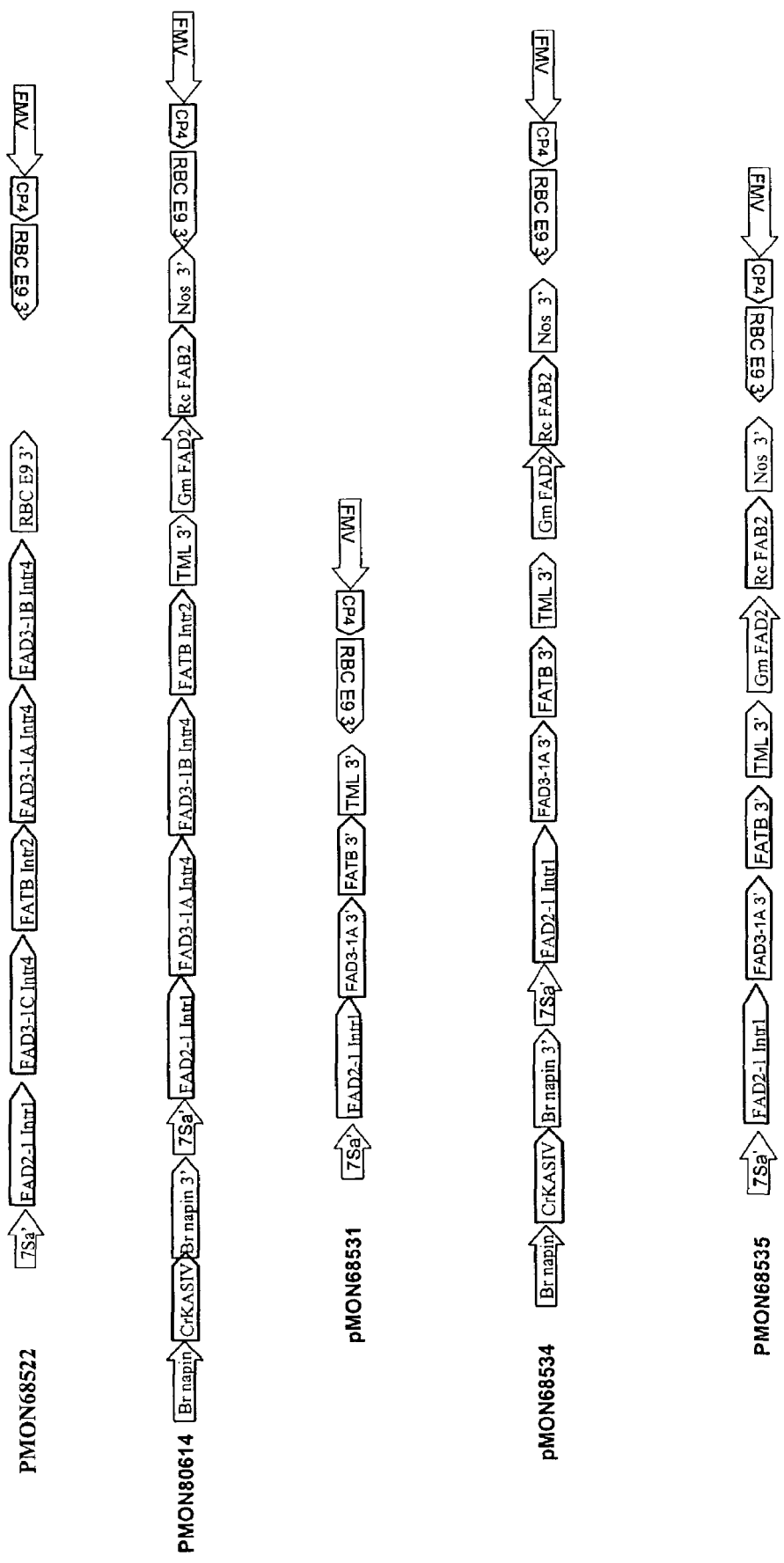

Referring now to FIG. 10, soybean FAD2-1 intron I (SEQ ID NO: 1 or 2), FAD3-1C intron 4 (SEQ ID NO: 14), FATB intron II (SEQ ID NO: 30), FAD3-1A intron 4 (SEQ ID NO: 10), and FAD3-1B intron 4 (SEQ ID NO: 24) sequences are amplified via PCR to result in PCR products that include reengineered restriction sites at both ends. The PCR products are cloned directly, in sense orientation, into a vector containing the soybean 7Sα' promoter and a pea Rubisco E9 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68522, is depicted in FIG. 10 and is used for transformation using methods as described herein.

Soybean FAD2-1 intron 1 (SEQ ID NO: 1 or 2), FAD3-1A intron 4 (SEQ ID NO: 10), FAD3-1B intron 4 (SEQ ID NO: 24), and FATB intron II (SEQ ID NO: 30) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. Vectors containing a *C. pulcherrima* KAS IV gene (SEQ ID NO: 39) regulated by a Brassica napin promoter and a Brassica napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON80614, is depicted in FIG. 10 and is used for transformation using methods as described herein.

Soybean FAD2-1 intron 1 (SEQ ID NO: 1 or 2), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68531, is depicted in FIG. 10 and is used for transformation using methods as described herein.

Soybean FAD2-1 intron 1 (SEQ ID NO: 1 or 2), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. Vectors containing a *C. pulcherrima* KAS IV gene (SEQ ID NO: 39) regulated by a Brassica napin promoter and a Brassica napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON68534, is depicted in FIG. 10 and is used for transformation using methods as described herein.

Soybean FAD2-1 intron 1 (SEQ ID NO: 1 or 2), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *R. communis* delta-9 desaturase (FAB2) gene (SEQ ID NO: 40) regulated by a soybean FAD2 promoter and a nos 3' termination sequence, is cut with appropriate restriction enzymes, and ligated into pMON41164. The resulting gene expression construct, pMON68535, is depicted in FIG. 10 and is used for transformation using methods as described herein.

Figure 11:
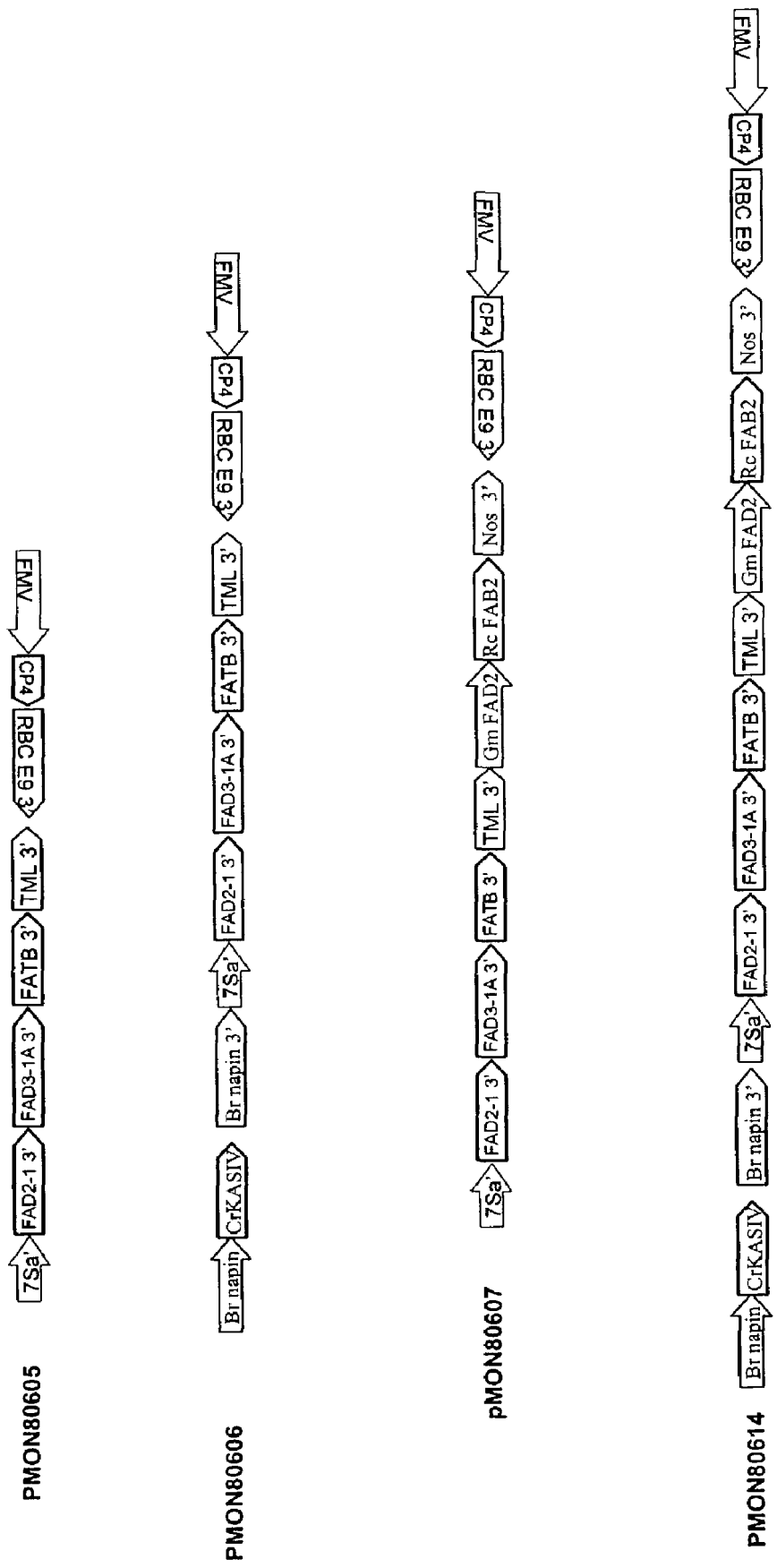

Referring now to FIG. 11, soybean FAD2-1 3'UTR (SEQ ID NO: 5), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80605, is depicted in FIG. 11 and is used for transformation using methods as described herein.

Soybean FAD2-1 3'UTR (SEQ ID NO: 5), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a Brassica napin promoter and a Brassica napin 3' termination sequence is cut with appropriate restriction enzymes, and ligated into pMON41164. The resulting gene expression construct, pMON80606, is depicted in FIG. 11 and is used for transformation using methods as described herein.

Soybean FAD2-1 3'UTR (SEQ ID NO: 5), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *R. communis* delta-9 desaturase (FAB2) gene (SEQ ID NO: 40) regulated by a soybean FAD2 promoter and a nos 3' termination sequence is cut with appropriate restriction enzymes, and ligated into pMON41164. The resulting gene expression construct, pMON80607, is depicted in FIG. 11 and is used for transformation using methods as described herein.

Soybean FAD2-1 3'UTR (SEQ ID NO: 5), FAD3-1A 3'UTR (SEQ ID NO: 16), and FATB 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. Vectors containing a *C. pulcherrima* KAS W gene (SEQ ID NO: 39) regulated by a Brassica napin promoter and a Brassica napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON80614, is depicted in FIG. 11 and is used for transformation using methods as described herein.

Figure 12:
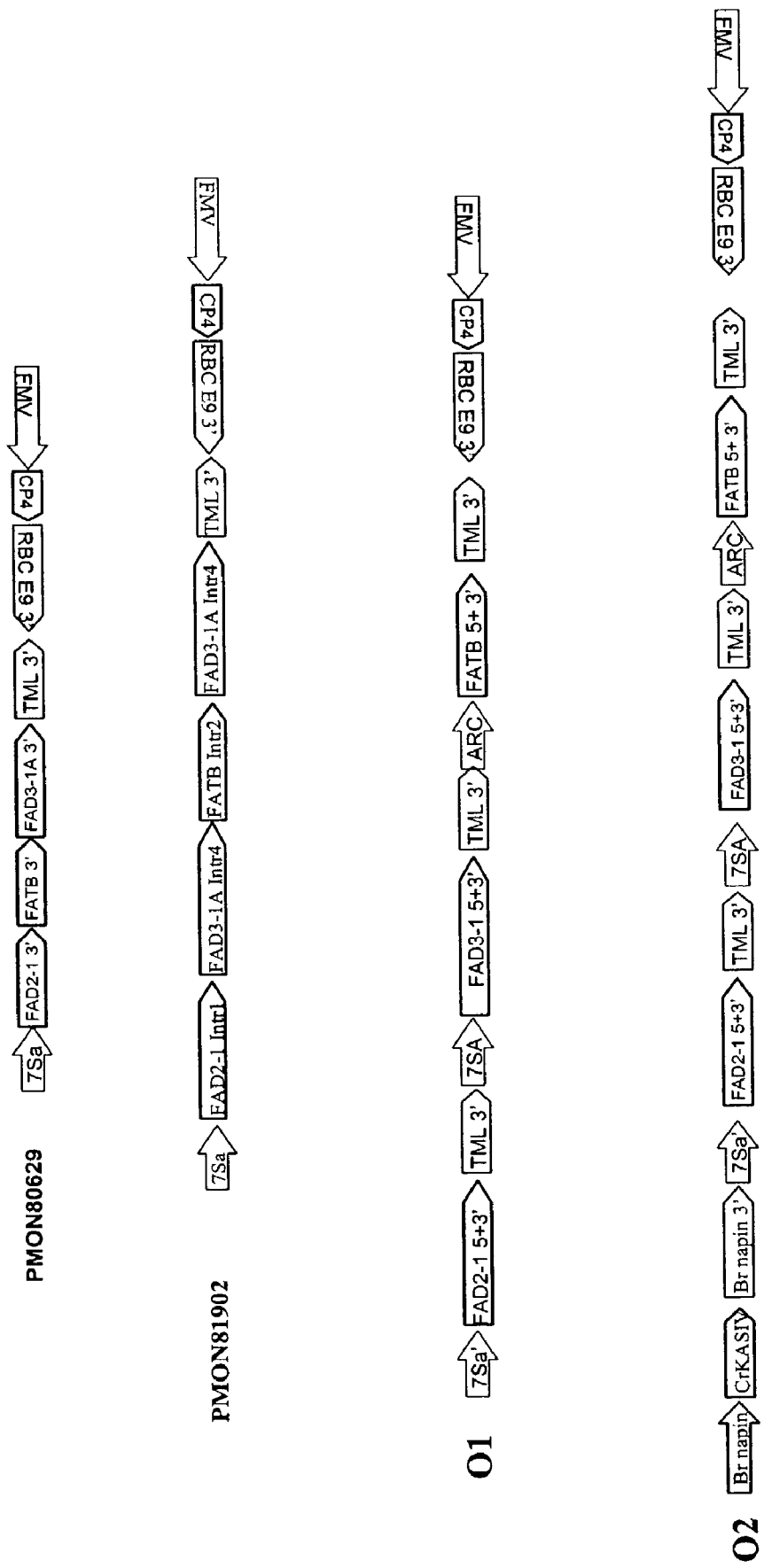

Referring now to FIG. 12, soybean FAD2-1 3'UTR (SEQ ID NO: 5), FATB 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in sense orientation, into a vector containing the soybean 7Sα promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80629, is depicted in FIG. 12 and is used for transformation using methods as described herein.

Soybean FAD2-1 intron 1 (SEQ ID NO: 1 or 2), FAD3-1A intron 4 (SEQ ID NO: 10), FATB intron II (SEQ ID NO: 30), and FAD3-1A intron 4 (SEQ ID NO: 10) sequences are amplified via PCR to result in PCR products that include reengineered restriction sites at both ends. The PCR products are cloned directly, in sense orientation, into a vector containing the soybean 7Sa promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON81902, is depicted in FIG. 12 and is used for transformation using methods as described herein.

Soybean FAD2-1 5'UTR-3'UTR (SEQ ID NOs: 6 and 5, ligated together), FAD3-1 5'UTR-3'UTR (SEQ ID NOs: 17 and 16, ligated together, or 27 and 26, ligated together), and FATB 5'UTR-3'UTR (SEQ ID NOs: 37 and 36, ligated together) sequences are amplified via PCR to result in PCR products that include reengineered restriction sites at both ends. The FAD2-1 PCR product is cloned directly, in sense orientation, into a vector containing the soybean 7Sα' promoter and a tml 3' termination sequence, by way of XhoI sites engineered onto the 5' ends of the PCR primers. Similarly, the FAD3-1 PCR product is cloned directly, in sense orientation, into a vector containing the soybean 7Sα' promoter and a tml 3' termination sequence, by way of XhoI sites engineered onto the 5' ends of the PCR primers. The FATB PCR product is cloned directly, in sense orientation, into a vector containing the arcelin promoter and a tml 3' termination sequence, by way of XhoI sites engineered onto the 5' ends of the PCR primers. These vectors are then cut with NotI and ligated into pMON41164, a vector that contains the CP4 EPSPS gene regulated by the FMV promoter and a pea Rubisco E9 3' termination sequence. The resulting gene expression construct, O1, is depicted in FIG. 12 and is used for transformation using methods as described herein.

Soybean FAD2-1 5'UTR-3'UTR (SEQ ID NOs: 6 and 5, ligated together), FAD3-1 5'UTR-3'UTR (SEQ ID NOs: 17 and 16, ligated together, or 27 and 26, ligated together), and FATB 5'UTR-3'UTR (SEQ ID NOs: 37 and 36, ligated together) sequences are amplified via PCR to result in PCR products that include reengineered restriction sites at both ends. The FAD2-1 PCR product is cloned directly, in sense orientation, into a vector containing the soybean 7Sα' promoter and a tml 3' termination sequence, by way of XhoI sites engineered onto the 5' ends of the PCR primers. Similarly, the FAD3-1 PCR product is cloned directly, in sense orientation, into a vector containing the soybean 7Sα promoter and a tml 3' termination sequence, by way of XhoI sites engineered onto the 5' ends of the PCR primers. The FATB PCR product is cloned directly, in sense orientation, into a vector containing the arcelin promoter and a tml 3' termination sequence, by way of XhoI sites engineered onto the 5' ends of the PCR primers. These vectors are then cut with NotI and ligated into pMON41164, a vector that contains the CP4 EPSPS gene regulated by the FMV promoter and a pea Rubisco E9 3' termination sequence. A vector containing a C. pulcherrima KAS IV gene (SEQ ID NO: 39) regulated by a Brassica napin promoter and a Brassica napin 3' termination sequence is cut with appropriate restriction enzymes, and ligated into pMON41164. The resulting gene expression construct, O2, is depicted in FIG. 12 and is used for transformation using methods as described herein.

Figure 13:
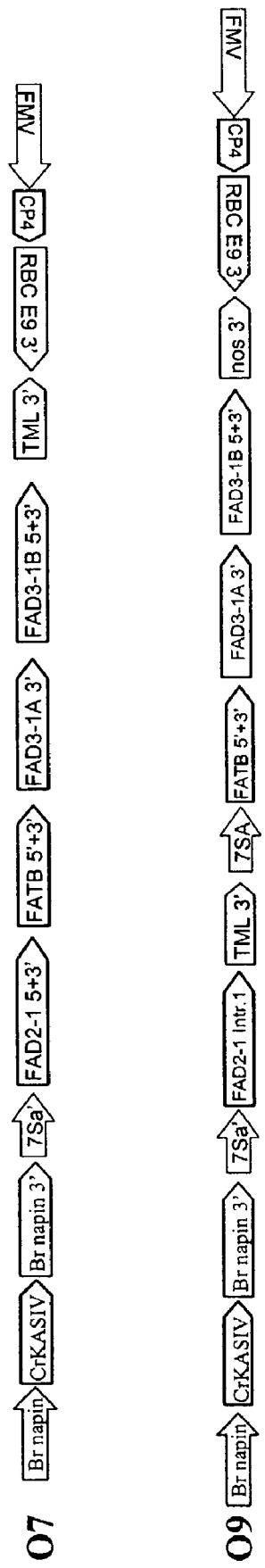

Referring now to FIG. 13, soybean FAD2-1 5'UTR-3'UTR (SEQ ID NOs: 6 and 5, ligated together), FATB 5'UTR-3'UTR (SEQ ID NOs: 37 and 36, ligated together), FAD3-1A 3'UTR (SEQ ID NO: 16), and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vectors are then cut with NotI and ligated into pMON41164, a vector that contains the CP4 EPSPS gene regulated by the FMV promoter and a pea Rubisco E9 3' termination sequence. A vector////////// containing a C. pulcherrima KAS IV gene (SEQ ID NO: 39) regulated by a Brassica napin promoter and a Brassica napin 3' termination sequence is cut with appropriate restriction enzymes, and ligated into pMON41164. The resulting gene expression construct, O7, is depicted in FIG. 13 and is used for transformation using methods as described herein.

Soybean FAD2-1 intron 1 (SEQ ID NO: 1 or 2) is amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. Soybean FATB 5'UTR-3'UTR (SEQ ID NOs: 37 and 36, ligated together), FAD3-1A 3'UTR (SEQ ID NO: 16), and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in sense orientation, into a vector containing the soybean 7Sα promoter and a nos 3' termination sequence, by way of XhoI sites engineered onto the 5' ends of the PCR primers. The vectors are then cut with NotI and ligated into pMON41164, a vector that contains the CP4 EPSPS gene regulated by the FMV promoter and a pea Rubisco E9 3' termination sequence. A vector containing a C. pulcherrima KAS IV gene (SEQ ID NO: 39) regulated by a Brassica napin promoter and a Brassica napin 3' termination sequence is cut with appropriate restriction enzymes, and ligated into pMON41164. The resulting gene expression construct, O9, is depicted in FIG. 13 and is used for transformation using methods as described herein.

2C. Antisense Constructs

Figure 14:
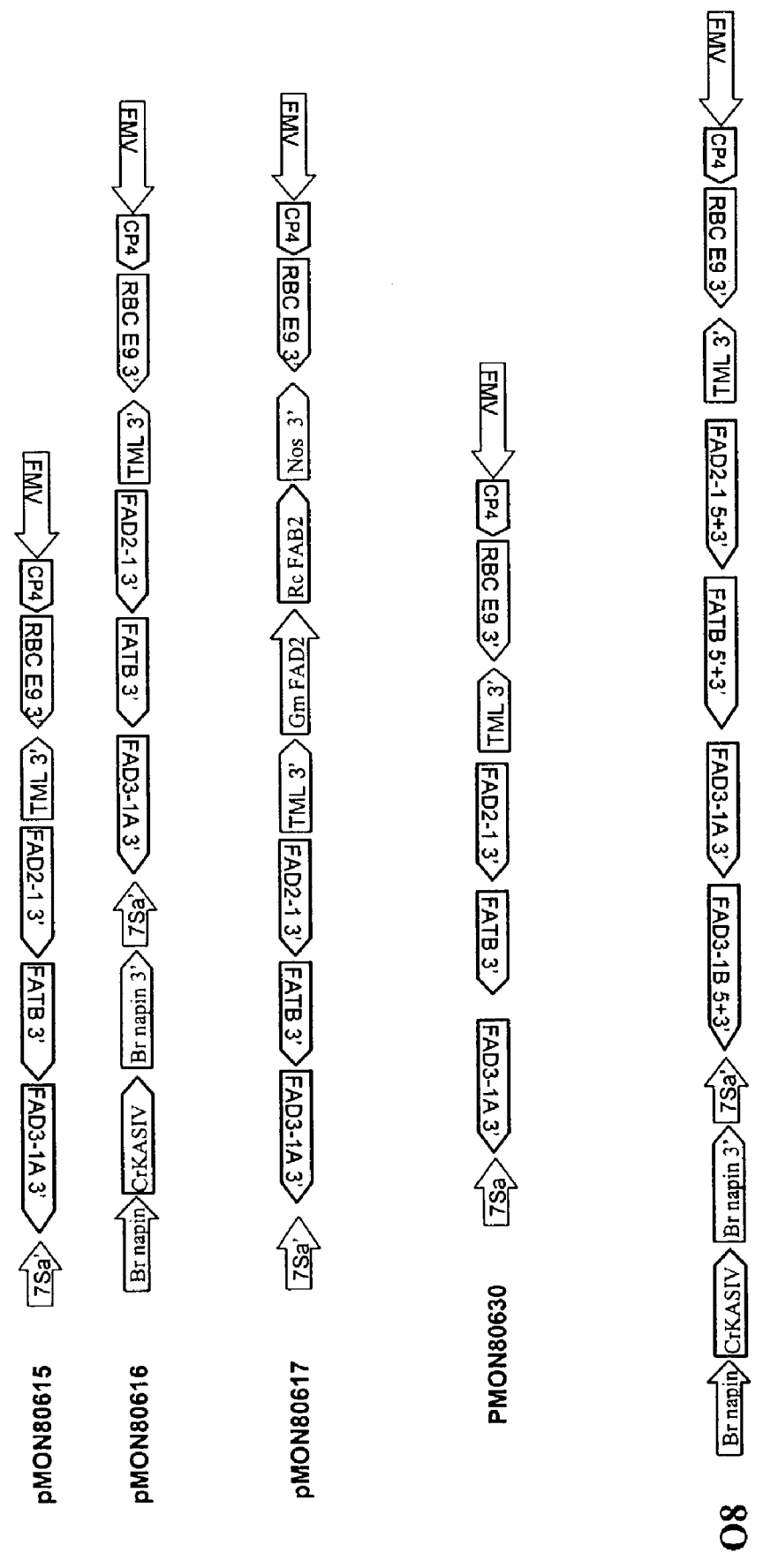
Figure 15:
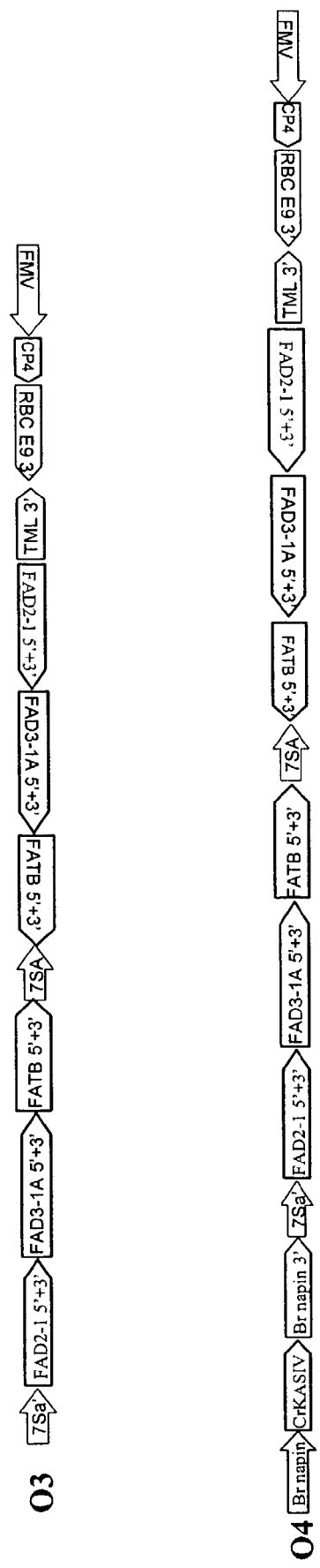

FIG. 14 depicts nucleic acid molecules of the present invention in which the first sets of DNA sequences are capable of expressing antisense constructs, and FIG. 15 depicts nucleic acid molecules of the present invention in which the first sets of DNA sequences are capable of expressing combinations of sense and antisense constructs. The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which is any promoter functional in a plant, or any plant promoter, and may be an FMV promoter, a napin promoter, a 7S (either 7Sα or 7Sα') promoter, an arcelin promoter, a delta-9 desaturase promoter, or a FAD2-1A promoter.

Referring now to FIG. 14, soybean FAD2-1 3'UTR (SEQ ID NO: 5), FATB 3'UTR (SEQ ID NO: 36), and FAD3-1A 3

'UTR (SEQ ID NO: 16) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80615, is depicted in FIG. 14 and is used for transformation using methods as described herein.

Soybean FAD2-1 3'UTR (SEQ ID NO: 5), FATB 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a Brassica napin promoter and a Brassica napin 3' termination sequence is cut with appropriate restriction enzymes, and ligated into pMON41164. The resulting gene expression construct, pMON80616, is depicted in FIG. 14 and is used for transformation using methods as described herein.

Soybean FAD2-1 3'UTR (SEQ ID NO: 5), FATB 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *R. communis* delta-9 desaturase (FAB2) gene (SEQ ID NO: 40) regulated by a soybean FAD2 promoter and a nos 3' termination sequence, is cut with appropriate restriction enzymes, and ligated into pMON41164. The resulting gene expression construct, pMON80617, is depicted in FIG. 14 and is used for transformation using methods as described herein.

Soybean FAD2-1 3'UTR (SEQ ID NO: 5), FATB 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in antisense orientation, into a vector containing the soybean 7Sα promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80630, is depicted in FIG. 14 and is used for transformation using methods as described herein.

Soybean FAD2-1 5'UTR-3'UTR (SEQ ID NOs: 6 and 5, ligated together), FATB 5'UTR-3'UTR (SEQ ID NOs: 37 and 36, ligated together), FAD3-1A 3'UTR (SEQ ID NO: 16), and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a Brassica napin promoter and a Brassica napin 3' termination sequence is cut with appropriate restriction enzymes, and ligated into pMON41164. The resulting gene expression construct, O8, is depicted in FIG. 14 and is used for transformation using methods as described herein.

Referring now to FIG. 15, soybean FAD2-1 5'UTR-3'UTR (SEQ ID NOs: 6 and 5, ligated together), FAD3-1A 5'UTR-3'UTR (SEQ ID NOs: 17 and 16, ligated together), and FATB 5'UTR-3'UTR (SEQ ID NOs: 37 and 36, ligated together) sequences are amplified via PCR to result in PCR products that include reengineered restriction sites at both ends. The PCR products are cloned directly in sense and antisense orientation into a vector containing the soybean 7Sα' promoter and a tml 3' termination sequence, with an additional soybean 7Sα promoter located between the sense and antisense sequences, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, O3, is depicted in FIG. 15 and is used for transformation using methods as described herein.

Soybean FAD2-1 5'UTR-3'UTR (SEQ ID NOs: 6 and 5, ligated together), FAD3-1A 5'UTR-3'UTR (SEQ ID NOs: 27 and 26, ligated together), and FATB 5'UTR-3'UTR (SEQ ID NOs: 37 and 36, ligated together) sequences are amplified via PCR to result in PCR products that include reengineered restriction sites at both ends. The PCR products are cloned directly in sense and antisense orientation into a vector containing the soybean 7Sα' promoter and a tml 3' termination sequence, with an additional soybean 7Sα promoter located between the sense and antisense sequences, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a Brassica napin promoter and a Brassica napin 3' termination sequence is cut with appropriate restriction enzymes, and ligated into pMON41164. The resulting gene expression construct, O4, is depicted in FIG. 15 and is used for transformation using methods as described herein.

The above-described nucleic acid molecules are preferred embodiments which achieve the objects, features and advantages of the present invention. It is not intended that the present invention be limited to the illustrated embodiments. The arrangement of the sequences in the first and second sets of DNA sequences within the nucleic acid molecule is not limited to the illustrated and described arrangements, and may be altered in any manner suitable for achieving the objects, features and advantages of the present invention as

Example 3

Plant Transformation and Analysis

The constructs of Examples 1 and 2 are stably introduced into soybean (for example, Asgrow variety A4922 or Asgrow variety A3244 or Asgrow variety A3525) by the methods described earlier, including the methods of McCabe et al., Bio/Technology, 6:923-926 (1988), or Agrobacterium-mediated transformation. Transformed soybean plants are identified by selection on media containing glyphosate. Fatty acid compositions are analyzed from seed of soybean lines transformed with the constructs using gas chromatography. In addition, any of the constructs may contain other sequences of interest, as well as different combinations of promoters.

For some applications, modified fatty acid compositions are detected in developing seeds, whereas in other instances, such as for analysis of oil profile, detection of fatty acid modifications occurring later in the FAS pathway, or for detection of minor modifications to the fatty acid composition, analysis of fatty acid or oil from mature seeds is preferred. Furthermore, analysis of oil and/or fatty acid content of individual seeds may be desirable, especially in detection of oil modification in the segregating R1 seed populations. As used herein, R0 indicates the plant and seed arising from transformation/regeneration protocols described herein, and R1 indicates plants and seeds generated from the transgenic R0 seed.

Fatty acid compositions are determined for the seed of soybean lines transformed with the constructs of Example 2. One to ten seeds of each of the transgenic and control soybean lines are ground individually using a tissue homogenizer (Pro Scientific) for oil extraction. Oil from ground soybean seed is extracted overnight in 1.5 ml heptane containing triheptadecanoin (0.50 mg/ml). Aliquots of 200 µl of the extracted oil are derivatized to methyl esters with the addition of 500 µl sodium methoxide in absolute methanol. The derivatization reaction is allowed to progress for 20 minutes at 50° C. The reaction is stopped by the simultaneous addition of 500 µl 10% (w/v) sodium chloride and 400 µl heptane. The resulting fatty acid methyl esters extracted in hexane are resolved by gas chromatography (GC) on a Hewlett-Packard model 6890 GC (Palo Alto, Calif.). The GC was fitted with a Supelcowax 250 column (30 m, 0.25 mm id, 0.25 micron film thickness) (Supelco, Bellefonte, Pa.). Column temperature is 175° C. at injection and the temperature programmed from 175° C. to 245° C. to 175° C. at 40° C./min. Injector and detector temperatures are 250° C. and 270° C., respectively.

Example 4

Synthesized Fuel Oil with Improved Biodiesel Properties

A synthesized fuel oil fatty acid composition is prepared having the following mixtures of fatty acid methyl esters: 73.3% oleic acid, 21.4% linoleic acid, 2.2% palmitic acid, 2.1% linolenic acid and 1.0% stearic acid (all by weight). Purified fatty acid methyl esters are obtained from Nu-Chek Prep, Inc., Elysian, Minn., USA. The cetane number and ignition delay of this composition is determined by the Southwest Research Institute using an Ignition Quality Tester ("IQT") 613 (Southwest Research Institute, San Antonio, Tex., USA).

An IQT consists of a constant volume combustion chamber that is electrically heated, a fuel injection system, and a computer that is used to control the experiment, record the data and provide interpretation of the data. The fuel injection system includes a fuel injector nozzle that forms an entrance to the combustion chamber. A needle lift sensor in the fuel injector nozzle detects fuel flow into the combustion chamber. A pressure transducer attached to the combustion chamber measures cylinder pressure, the pressure within the combustion chamber. The basic concept of an IQT is measurement of the time from the start of fuel injection into the combustion chamber to the start of combustion. The thermodynamic conditions in the combustion chamber are precisely controlled to provide consistent measurement of the ignition delay time.

For a cetane number and ignition delay test, the test fuel is filtered using a 5-micron filter. The fuel reservoir, injection line, and nozzle are purged with pressurized nitrogen. The fuel reservoir is then cleaned with a lint free cloth. A portion of the test fuel is used to flush the fuel reservoir, injection line, and nozzle. The reservoir is filled with the test fuel and all air is bled from the system. The reservoir is pressurized to 50 psig. The method basically consists of injecting at high pressure a precisely metered quantity of the test fuel into the combustion chamber that is charged with air to the desired pressure and temperature. The measurement consists of determining the time from the start of injection to the onset of combustion, often referred to as the ignition delay time. This determination is based on the measured needle lift and combustion chamber pressures. The normal cetane rating procedure calls for setting the skin temperature at 567.5° C. and the air pressure at 2.1 MPa.

A fuel with a known injection delay is run in the IQT combustion bomb at the beginning of the day to make sure the unit is operating within normal parameters. The test synthetic is then run. The known fuel is run again to verify that the system has not changed. Once the fuel reservoir is reconnected to the fuel injection pump, the test procedure is initiated on the PC controller. The computer controls all the procedure, including the air charging, fuel injection, and exhaust events. 32 repeat combustion events are undertaken.

The ignition delay is the time from the start of injection to the start of ignition. It is determined from the needle lift and cylinder pressure data. The rise of the injection needle signals start of injection. The cylinder pressure drops slightly due to the cooling effect of the vaporization of the fuel. Start of combustion is defined as the recovery time of the cylinder pressure—increases due to combustion to the pressure it was just prior to fuel injection.

The measured ignition delay times are then used to determine the cetane number based on a calibration curve that is incorporated into the data acquisition and reduction software. The calibration curve, consisting of cetane number as a function of ignition delay time, is generated using blends of the primary reference fuels and NEG check fuels. In the case of test fuels that are liquid at ambient conditions, the calibration curve is checked on a daily basis using at least one check fuel of known cetane number (Ryan, "Correlation of Physical and Chemical Ignition Delay to Cetane Number", SAE Paper 852103 (1985); Ryan, "Diesel Fuel Ignition Quality as Determined in a Constant Volume Combustion Bomb", SAE Paper 870586 (1986); Ryan, "Development of a Portable Fuel Cetane Quality Monitor", Belvoir Fuels and Lubricants Research Facility Report No. 277, May (1992); Ryan, "Engine and Constant Volume Bomb Studies of Diesel Ignition and Combustion", SAE Paper 881616 (1988); and Allard et al., "Diesel Fuel Ignition Quality as Determined in the Ignition Quality Tester ("IQT")", SAE Paper 961182 (1996)). As shown in Table 3, the synthesized oil composition exhibits cetane numbers and ignition delays that are suitable for use for example, without limitation, as a biodiesel oil.

TABLE 3

| Fuel Name | Test Number | Cetane Number | Std. Dev. Cetane No. | Ignition Delay (ms) | Std. Dev. Ign. Delay |
|---|---|---|---|---|---|
| Check-High[1] | 1777 | 49.55 | 0.534 | 4.009 | 0.044 |
| Check-High | 1778 | 49.33 | 0.611 | 4.028 | 0.051 |
| Average | | 49.4 | | 4.02 | |
| Synthesized Oil | 1779 | 55.02 | 1.897 | 3.622 | 0.116 |
| Synthesized Oil | 1780 | 55.65 | 1.807 | 3.583 | 0.109 |
| Synthesized Oil | 1781 | 55.63 | 1.649 | 3.583 | 0.098 |
| Average | | 55.4 | | 3.60 | |
| Check-High | 1786 | 49.2 | 0.727 | 4.04 | 0.061 |

[1]The fuel called "Check-High" is a calibration fuel. It should have a cetane number of 49.3 ± 0.5.
The unit is checked with the calibration before and after running the synthetic test fuel.

The density (ASTM D-4052) cloud point (ASTM D-2500), pour point (ASTM D-97), and cold filter plugging point (IP 309/ASTM D-6371) are determined for the synthesized oil using ASTM D protocols. ASTM D protocols are obtained from ASTM, 100 Barr Harbor Drive, West Conshohocken, Pa., USA. The results of these tests are set forth in Table 4. As shown in Table 4, the synthesized oil composition exhibits numbers that are suitable for use as, for example without limitation, as a biodiesel oil.

TABLE 4

| TEST | METHOD | RESULTS |
|---|---|---|
| Density | ASTM D-4052 | 0.8791 g/mL |
| Cloud Point | ASTM D-2500 | −18 deg. C. |
| Pour Point | ASTM D-97 | −21 deg. C. |
| Cold Filter Plugging Point | IP. 309 (same as ASTM D-6371) | −21 deg. C. |

Levels of nitric oxide emissions are estimated by evaluating the unsaturation levels of a biologically-based fuel, by measuring the fuel density and indirectly calculating the estimated emissions levels, or by directly measuring. There are also standard protocols available for directly measuring levels of nitric oxide emissions. The synthesized oil is estimated to have lower nitric oxide emissions levels than methyl esters of fatty acids made from conventional soybean oil based on an evaluation of the overall level of unsaturation in the synthesized oil. Oils containing larger numbers of double bonds, i.e., having a higher degree of unsaturation, tend to produce higher nitric oxide emissions. The oil has a total of 123 double bonds, as compared to conventional soybean oil's total of 153 double bonds, as shown in Table 5.

TABLE 5

| SYNTHETIC OIL | |
|---|---|
| 73% oleic acid (18:1) × 1 double bond = | 73 |
| 22% linoleic acid (18:2) × 2 double bonds = | 44 |
| 2% linolenic acid (18:3) × 3 double bonds = | 6 |
| TOTAL double bonds | 123 |
| CONVENTIONAL SOYBEAN OIL | |
| 23% oleic acid (18:1) × 1 double bond = | 23 |
| 53% linoleic acid (18:2) × 2 double bonds = | 106 |
| 8% linolenic acid (18:3) × 3 double bonds = | 24 |
| TOTAL double bonds | 153 |

As reported by the National Renewable Energy Laboratory, Contract No. ACG-8-17106-02 Final Report, *The Effect Of Biodiesel Composition On Engine Emissions From A DDC Series 60 Diesel Engine,* (June 2000), nitric acid emissions of biodiesel compositions are predicted by the formula $y=46.959x-36.388$ where y is the oxide emissions in grams/brake horse power hours; and x is the density of biodiesel. The formula is based on a regression analysis of nitric acid emission data in a test involving 16 biodiesel fuels. The test makes use of a 1991 calibration, production series 60 model Detroit Diesel Corporation engine.

The density of the synthesized oil is determined by Southwest Research Institute using the method ASTM D4052. The result shown in Table 4 is used in the above equation to predict a nitric oxide emission value of 4.89 g/bhp-h. This result is compared to a control soybean product. The National Renewable Energy Laboratory report gives the density and nitric oxide emissions of a control soy based biodiesel (methyl soy ester IGT). The density of the control biodiesel is 0.8877 g/mL, giving a calculated nitric oxide emission of 5.30 g/bhp-h. This calculated emission value is similar to the experimental value for nitric oxide emission of 5.32 g/bhp-h. The synthesized oil composition exhibits improved numbers compared to the control and is suitable for use, for example without limitation, as a biodiesel oil.

Example 5

Optimum Fatty Acid Composition for Healthy Serum Lipid Levels

The cholesterol lowering properties of vegetable compositions are determined to identify fatty acid compositions that have a more favorable effect on serum lipid levels than conventional soybean oil (i.e., lower LDL-cholesterol and higher HDL-cholesterol). Published equations based on 27 clinical trials (Mensink, R. P. and Katan, M. B. *Arteriosclerosis and Thrombosis,* 12:911-919 (1992)) are used to compare the effects on serum lipid levels in humans of new oilseed compositions with that of normal soybean oil.

Table 6 below presents the results of the change in serum lipid levels where 30% of dietary energy from carbohydrate is substituted by lipids. The results show that soybean oil already has favorable effects on serum lipids when it replaces carbohydrates in the diet. Improvements on this composition are possible by lowering saturated fat levels and by obtaining a linoleic acid level between 10-30% of the total fatty acids, preferably about 15-25% of the total fatty acids. When the proportion of linoleic acid is less than 10% of the total fatty acids, the new composition raises LDL-cholesterol compared to control soybean oil, even though the saturated fat content is lowered to 5% of the total fatty acids. When the proportion of linoleic acid is increased, the ability of the composition to raise serum HDL levels is reduced. Therefore, the preferred linoleic acid composition is determined to be about 15-25% of the total fatty acids.

TABLE 6

| | Fatty acids | | | | | | Serum Lipids |
|---|---|---|---|---|---|---|---|
| | C16:0 | C18:0 | C18:1 | C18:2 | C18:3 | Other (C20:1) | |
| Soy control (%) | 11.000 | 4.000 | 23.400 | 53.200 | 7.800 | 0.600 | |
| Proportion of 30% fat E (%) | 3.300 | 1.200 | 7.020 | 15.960 | 2.340 | 0.180 | |
| LDL Calculation (mg/dl) | 4.224 | 1.536 | 1.685 | 8.778 | 1.287 | 0.043 | −6.033 |
| HDL Calc (mg/dl) | 1.551 | 0.564 | 2.387 | 4.469 | 0.655 | 0.061 | 9.687 |
| 3% 18:2, <6% sat (%) | 3.000 | 2.000 | 85.000 | 3.000 | 3.000 | 4.000 | |
| Proportion of 30% fat E (%) | 0.900 | 0.600 | 25.500 | 0.900 | 0.900 | 1.200 | |
| LDL Calculation (mg/dl) | 1.152 | 0.768 | 6.120 | 0.495 | 0.495 | 0.288 | −5.478 |
| vs. control (mg/dl) | | | | | | | 0.555 |
| HDL calculation (mg/dl) | 0.423 | 0.282 | 8.670 | 0.252 | 0.252 | 0.408 | 10.287 |
| vs. control (mg/dl) | | | | | | | 0.600 |
| 10% 18:2, <6% sat (%) | 3.000 | 2.000 | 72.000 | 10.000 | 3.000 | 10.000 | |
| Proportion of 30% fat E (%) | 0.900 | 0.600 | 21.600 | 3.000 | 0.900 | 3.000 | |
| LDL Calculation (mg/dl) | 1.152 | 0.768 | 5.184 | 1.650 | 0.495 | 0.720 | −6.129 |
| vs. control (mg/dl) | | | | | | | −0.096 |
| HDL calculation (mg/dl) | 0.423 | 0.282 | 7.344 | 0.840 | 0.252 | 1.020 | 10.161 |
| vs. control (mg/dl) | | | | | | | 0.474 |
| 20% 18:2, <6% sat (%) | 3.000 | 2.000 | 65.000 | 20.000 | 3.000 | 7.000 | |
| Proportion of 30% fat E (%) | 0.900 | 0.600 | 19.500 | 6.000 | 0.900 | 2.100 | |
| LDL Calculation (mg/dl) | 1.152 | 0.768 | 4.680 | 3.300 | 0.495 | 0.504 | −7.059 |
| vs. control (mg/dl) | | | | | | | −1.026 |
| HDL calculation (mg/dl) | 0.423 | 0.282 | 6.630 | 1.680 | 0.252 | 0.714 | 9.981 |
| vs. control (mg/dl) | | | | | | | 0.294 |
| 21% 18:2, <3.2% sat (%) | 2.000 | 1.000 | 72.000 | 21.000 | 1.000 | 3.000 | |
| Proportion of 30% fat E (%) | 0.600 | 0.300 | 21.600 | 6.300 | 0.300 | 0.900 | |
| LDL Calculation (mg/dl) | 0.768 | 0.384 | 5.184 | 3.465 | 0.165 | 0.216 | −7.878 |
| vs. control (mg/dl) | | | | | | | −1.845 |
| HDL calculation (mg/dl) | 0.282 | 0.141 | 7.344 | 1.764 | 0.084 | 0.306 | 9.921 |
| vs. control (mg/dl) | | | | | | | 0.234 |
| 30% 18:2, <6% sat (%) | 3.000 | 2.000 | 57.000 | 3.000 | 3.000 | 5.000 | |
| Proportion of 30% fat E (%) | 0.900 | 0.600 | 17.100 | 9.000 | 0.900 | 1.500 | |
| LDL Calculation (mg/dl) | 1.152 | 0.768 | 4.104 | 4.950 | 0.495 | 0.360 | −7.989 |
| vs. control (mg/dl) | | | | | | | −1.956 |
| HDL calculations (mg/dl) | 0.423 | 0.282 | 5.814 | 2.520 | 0.252 | 0.510 | 9.801 |
| vs. control (mg/dl) | | | | | | | 0.114 |

---

What is claimed is:

1. A soybean seed exhibiting an oil composition comprising 55 to 80% by weight oleic acid and 8% or less by weight saturated fatty acids, wherein said seed comprises a recombinant nucleic acid molecule comprising a first set of DNA sequence that is capable, when expressed in a host cell, of suppressing the endogenous expression of FAD2- 1A and FATB, wherein said sequence comprises
   (i) at least 50 contiguous nucleotides of an intron of FAD2-1A; and
   (ii) a sequence selected from the group consisting of at least 50 contiguous nucleotides of a nucleic acid sequence at least 95% identical to SEQ ID NO:36, at least 50 contiguous nucleotides of a nucleic acid sequence at least 95% identical to SEQ ID NO:37, and combinations thereof.

2. The soybean seed of claim 1, wherein said at least 50 contiguous nucleotides of an intron of FAD2-1A is at least 100 contiguous nucleotides of a FAD2-1A intron 1.

3. The soybean seed of claim 1, wherein said recombinant nucleic acid molecule further comprises a FATB transit sequence.

4. The soybean seed of claim 2, wherein said at least 100 contiguous nucleotides of a FAD2-1A intron 1 is at least 95% identical to 100 contiguous nucleotides of SEQ ID NO: 1.

5. The soybean seed of claim 1, further comprising a second set of DNA sequence that is capable, when expressed in a host cell, of increasing expression of a beta-ketoacyl-ACP synthase IV and/or a delta-9 desaturase.

6. The soybean seed of claim 1 comprising 65 to 80% oleic acid and 2 to 8% saturated fatty acids.

7. The soybean seed of claim 1 comprising 3 to 6% saturated fatty acids.

8. The soybean seed of claim 6 comprising 65 to 75% oleic acid.

9. The soybean seed of claim 1 comprising 60 to 70% oleic acid.

10. The soybean seed of claim 1, wherein said first set of DNA sequence comprises at least 100 contiguous nucleotides at least 95% to SEQ ID NO:36.

11. The soybean seed of claim 1, wherein said first set of DNA sequence comprises at least 100 contiguous nucleotides at least 95% to SEQ ID NO:37.

12. The soybean seed of claim 1, wherein said first set of DNA sequence comprises at least 100 contiguous nucleotides at least 95% to SEQ ID NO:36 and at least 100 contiguous nucleotides at least 95% to SEQ ID NO:37.

* * * * *

UNITED STATES PATENT AND TRADEMARK OFFICE
CERTIFICATE OF CORRECTION

PATENT NO. : 7,601,888 B2  Page 1 of 1
APPLICATION NO. : 10/393347
DATED : October 13, 2009
INVENTOR(S) : Fillatti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 932 days.

Signed and Sealed this

Fifth Day of October, 2010

David J. Kappos
*Director of the United States Patent and Trademark Office*